(12) United States Patent
Parker et al.

(10) Patent No.: US 10,590,168 B2
(45) Date of Patent: Mar. 17, 2020

(54) SUBSTRATES FOR FLT3 KINASE AND USES THEREOF

(71) Applicant: REGENTS OF THE UNIVERSITY OF MINNESOTA, Minneapolis, MN (US)

(72) Inventors: Laurie L. Parker, Minneapolis, MN (US); Minervo Perez, Minneapolis, MN (US)

(73) Assignee: REGENTS OF THE UNIVERSITY OF MINNESOTA, Minneapolis, MN (US)

(*) Notice: Subject to any disclaimer, the term of this patent is extended or adjusted under 35 U.S.C. 154(b) by 0 days.

(21) Appl. No.: 15/603,273

(22) Filed: May 23, 2017

(65) Prior Publication Data

US 2017/0334950 A1 Nov. 23, 2017

Related U.S. Application Data

(60) Provisional application No. 62/340,384, filed on May 23, 2016.

(51) Int. Cl.
| | |
|---|---|
| *C07K 7/06* | (2006.01) |
| *C12Q 1/48* | (2006.01) |
| *C07K 14/715* | (2006.01) |
| *C07K 14/82* | (2006.01) |
| *C12N 9/12* | (2006.01) |

(52) U.S. Cl.
CPC .............. *C07K 7/06* (2013.01); *C07K 14/715* (2013.01); *C07K 14/82* (2013.01); *C12Q 1/485* (2013.01); *C12N 9/1205* (2013.01); *G01N 2500/02* (2013.01); *G01N 2500/20* (2013.01)

(58) Field of Classification Search
None
See application file for complete search history.

(56) References Cited

U.S. PATENT DOCUMENTS

| | | | |
|---|---|---|---|
| 4,612,302 A | 9/1986 | Szabo et al. | |
| 4,684,620 A | 8/1987 | Hruby et al. | |
| 4,853,371 A | 8/1989 | Coy et al. | |
| 7,279,298 B2 * | 10/2007 | Yamaguchi ............... | A23J 3/34 435/15 |
| 2013/0231265 A1 | 9/2013 | Parker et al. | |
| 2014/0072516 A1 | 3/2014 | Parker et al. | |
| 2016/0097084 A1 | 4/2016 | Parker et al. | |
| 2016/0376632 A1 | 12/2016 | Parker et al. | |
| 2017/0009273 A1 | 1/2017 | Yang et al. | |

OTHER PUBLICATIONS

Wang, Danhui et al, "High throughput screening of peptide substrates for tyrosine kinases featuring precisio(tm) kinases and pepscreen(r) custom peptide library." Sigma Aldrich sales literature, available May 15, 2015.*

Mercken, Luc et al, "Primary structure of bovine thyroglobulin deduced from the sequence of its 8,431 base complementary dna." Nature (1985) 316 p. 647-651.*
GenBank entry CAA26584, thyroglobulin precursor, Bos Taurus, entered Apr. 2005.*
Perez, et al., "Identification of FMS-Like Tyrosine Kinase 3 (FLT3) Substrates Using KALIP", Poster 63, United States Human Proteome Organization (US-HUPO) Conference, San Diego, CA, 7 pages (Mar. 2017).
Akiba, et al., "Click conjugation of a binuclear terbium(III) complex for real-time detection of tyrosine phosphorylation", Anal Chem 87(7), 3834-3840 (2015).
Bendall, et al., "Single-cell mass cytometry of differential immune and drug responses across a human hematopoietic continuum", Science 332 (6030), 687-696 (2011).
Bohmer, et al., "A substrate peptide for the FLT3 receptor tyrosine kinase", Br J Haematol 144(1), 127-130 (2009).
Chozinski, et al., "Twinkle, twinkle little star: photoswitchable fluorophores for super-resolution imaging", FEBS Letters 588, 3603-3612 (2014).
Cui, et al., "Modular, Antibody-free Time-Resolved LRET Kinase Assay Enabled by Quantum Dots and Tb(3+)-sensitizing Peptides", Sci Rep 6, 28971, DOI: 10.1038/srep28971 (2016).
Dai, et al., "Visual snapshots of intracellular kinase activity at the onset of mitosis", Chem Biol 14(11), 1254-1260 (2007).
Deng, et al., "Global Analysis of Human Nonreceptor Tyrosine Kinase Specificity Using High-Density Peptide Microarrays", J Proteome Res 13(10), 4339-4346 (2014).
Ding, et al., "Förster resonance energy transfer-based biosensors for multiparameter ratiometric imaging of Ca2+ dynamics and caspase-3 activity in single cells", Anal Chem 83, 9687-9693 (2011).
Enterina, et al., "Emerging fluorescent protein technologies", Current Opinion in Chemical Biology 27, 10-17 (2015).
Galperin, et al., "Three-chromophore FRET microscopy to analyze multiprotein interactions in living cells", Nat Methods 1, 209-217 (2004).
Gao, et al., "FRET-based activity biosensors to probe compartmentalized signaling", Chembiochem 11(2), 147-151 (2010).
Ghadiali, et al., "Protein kinase-actuated resonance energy transfer in quantum dot-peptide conjugates", ACS Nano 4(8), 4915-4919 (2010).
Grant, et al., "Multiplexed FRET to image multiple signaling events in live cells", Biophysical Journal 95(10), L69-71 (2008).
Hildebrandt, et al., "Luminescent terbium complexes: Superior Förster resonance energy transfer donors for flexible and sensitive multiplexed biosensing", Coordination Chemistry Reviews vol. 273-274, 125-138 (2014).
Horton, et al., "Multiplexing terbium- and europium-based TR-FRET readouts to increase kinase assay capacity", J Biomol Screen 15, 1008-1015 (2010).
Hospital, et al., "FLT3 inhibitors: clinical potential in acute myeloid leukemia", Onco Targets Ther 10, 607-615 (2017).
Irish, et al., "B-cell signaling networks reveal a negative prognostic human lymphoma cell subset that emerges during tumor progression", Proc Natl Acad Sci 107(29), 12747-12754 (2010).
Irish, et al., "Mapping normal and cancer cell signalling networks: towards single-cell proteomics", Nat Rev Cancer 6(2), 146-155 (2006).

(Continued)

*Primary Examiner* — Fred H Reynolds
(74) *Attorney, Agent, or Firm* — Viksnins Harris Padys Malen LLP

(57) ABSTRACT

The invention provides kinase substrates and methods comprising their use.

24 Claims, 19 Drawing Sheets
Specification includes a Sequence Listing.

(56) References Cited

OTHER PUBLICATIONS

Kienzler, et al., "Novel three-color FRET tool box for advanced protein and DNA analysis", Bioconjug Chem 22, 1852-1863 (2011).
Kim, et al., "Monitoring a coordinated exchange process in a four-component biological interaction system: development of a time-resolved terbium-based one-donor/three-acceptor multicolor FRET system", J Am Chem Soc 132(13), 4685-4692 (2010).
Kim, et al., "Quantitative fragment analysis of FLT3-ITD efficiently identifying poor prognostic group with high mutant allele burden or long ITD length", Blood Cancer Journal 5, e336, 7 pages (2015).
Kubota, et al., "Sensitive multiplexed analysis of kinase activities and activity-based kinase identification", Nat Biotechnol 27 (10), 933-940 (2009).
Kunz, et al., "A high-throughput, multiplexed kinase assay using a benchtop orbitrap mass spectrometer to investigate the effect of kinase inhibitors on kinase signaling pathways", Analytical Chemistry 84(14), 6233-6239 (2012).
Kupcho, et al., "Simultaneous monitoring of discrete binding events using dual-acceptor terbium-based LRET", J Am Chem Soc 129, 13372-13373 (2007).
Kuppers, "Mechanisms of B-cell lymphoma pathogenesis", Nat Rev Cancer 5(4), 251-262 (2005).
Lagunas-Rangel, et al., "FLT3-ITD and its current role in acute myeloid leukaemia", Med Oncol 34(6), 114 (2017).
Lawrence, et al., "Seeing is believing: peptide-based fluorescent sensors of protein tyrosine kinase activity", Chembiochem 8(4), 373-378 (2007).
Leick, et al., "The Future of Targeting FLT3 Activation in AML", Curr Hematol Malig Rep 12(3), 153-167 (2017).
Leung, et al., "FLT3 inhibition: a moving and evolving target in acute myeloid leukaemia", Leukemia 27(2), 260-268 (2013).
Lipchik, et al., "A peptide-based biosensor assay to detect intracellular Syk kinase activation and inhibition", Biochemistry 51, 7515-7524 (2012).
Lipchik, et al., "KINATEST-ID: a pipeline to develop phosphorylation-dependent terbium sensitizing kinase assays", J Am Chem Soc 137, 2484-2494 (2015).
Lipchik, et al., "Multicolored, $Tb^{3+}$-Based Antibody-Free Detection of Multiple Tyrosine Kinase Activities", Anal Chem 87(15), 7555-7558 (2015).
Lowe, et al., "Multiplex sensing of protease and kinase enzyme activity via orthogonal coupling of quantum dot-peptide conjugates", ACS Nano 6(1), 851-857 (2012).
Lukovic, et al., "Recognition-domain focused chemosensors: versatile and efficient reporters of protein kinase activity", J Am Chem Soc 130(38), 12821-12827 (2008).
Mashinchian, "Impacts of quantum dots in molecular detection and bioimaging of cancer.", BioImpacts 4, 149-166 (2014).
Meredith, et al., "Measurement of kinase activation in single mammalian cells", Nat Biotechnol 18(3), 309-312 (2000).
Ni, et al., "Dynamic visualization of cellular signaling", Advanced in Biochemical Eng Botechnol 119, 79-97 (2010).
Olenych, et al., "The fluorescent protein color palette", Curr Protoc Cell Biol, Chapter 21, Unit 21.5 (2007).
Peyker, et al., "Imaging activation of two Ras isoforms simultaneously in a single cell", Chembiochem 6, 78-85 (2005).
Piljic, et al., "Simultaneous recording of multiple cellular events by FRET", ACS Chem Biol 3(3), 156-160 (2008).
Placzek, et al., "A peptide biosensor for detecting intracellular Abl kinase activity using matrix-assisted laser desorption/ionization time-of-flight mass spectrometry", Anal Biochem 397(1), 73-78 (2010).
Pozarowski, et al., "Analysis of cell cycle by flow cytometry", Methods Mol Biol 281, 301-311 (2004).
Proctor, et al., "Development of a peptidase-resistant substrate for single-cell measurement of protein kinase B activation", Anal Chem 84(16), 7195-7202 (2012).
Resch-Genger, et al., "Quantum dots versus organic dyes as fluorescent labels", Nature Methods 5(9), 763-775 (2008).
Shaner, et al., "Advances in fluorescent protein technology", J Cell Sci 120 (Pt 24), 4247-4260 (2007).
Sharma, et al., "Deep quench: an expanded dynamic range for protein kinase sensors", J Am Chem Soc 129(10), 2742-2743 (2007).
Shults, et al., "A multiplexed homogeneous fluorescence-based assay for protein kinase activity in cell lysates", Nature Methods 2(4), 277-283 (2005).
Smith, et al., "FLT3 D835 Mutations Confer Differential Resistance to Type II FLT3 Inhibitors", Leukemia 29(12), 2390-2392 (2015).
Soughayer, et al., "Characterization of TAT-mediated transport of detachable kinase substrates", Biochemistry 43(26), 8528-8540 (2004).
Stains, et al., "Interrogating signaling nodes involved in cellular transformations using kinase activity probes", Chem Biol 19(2), 210-217 (2012).
Stirewalt, "The role of FLT3 in haematopoietic malignancies", Nat Rev Cancer 3(9), 650-665 (2003).
Swords, et al., "Targeting the FMS-like tyrosine kinase 3 in acute myeloid leukemia", Leukemia 26(10), 2176-2185 (2012).
Tang, et al., "Detection of early Abl kinase activation after ionizing radiation by using a peptide biosensor", Chembiochem 13(5), 665-673 (2012).
Terai, et al., "Small-molecule fluorophores and fluorescent probes for bioimaging", Pflugers Arch 465, 347-359 (2013).
Tremblay, et al., "Phosphorylation state-responsive lanthanide peptide conjugates: a luminescence switch based on reversible complex reorganization", Org Lett 8(13), 2723-2726 (2006).
Umezawa, et al., "New trends in near-infrared fluorophores for bioimaging", Analytical Sciences 30, 327-349 (2014).
Vogel, et al., "Improving lanthanide-based resonance energy transfer detection by increasing donor-acceptor distances", J Biomol Screen 11, 439 (2006).
Wang, et al., "Multicolor monitoring of dysregulated protein kinases in chronic myelogenous leukemia", ACS Chem Biol 5, 887-895 (2010).
White, et al., "Functional activity of the OCT-1 protein is predictive of long-term outcome in patients with chronic-phase chronic myeloid leukemia treated with imatinib", J Clin Oncol 28(16), 2761-2767 (2010).
Wysocki, et al., "Advances in the chemistry of small molecule fluorescent probes", Current Opinion in chemical Biology 15, 752-759 (2011).
Yamamoto, et al., "Activating mutation of D835 within the activation loop of FLT3 in human hematologic malignancies", Blood 97(8), 2434-2439 (2001).
Yeh, et al., "Real time visualization of protein kinase activity in living cells", J Biol Chem 277(13), 11527-11532 (2002).
Yoshimoto, et al., "FLT3-ITD up-regulates MCL-1 to promote survival of stem cells in acute myeloid leukemia via FLT3-ITD-specific STAT5 activation", Blood 114(24), 5034-5043 (2009).
Zheng, et al., "Ultra-stable organic fluorophores for single-molecule research", Chem Soc Rev 43, 1044-1056 (2014).
Lipchik, et al., "Time-resolved luminescence detection of Syk kinase activity through terbium sensitization", Anal Chem 85, 2582-2588 (2013).

* cited by examiner

FIGURE 3

Input

• Positive sequences: Unique KALIP derived FLT3 substrates

•Negative sequences: Tyrosine motifs that were not phosphorylated by FLT3

•KALIP derived protein sequence composition

Positional Probability Matrix

• Probability Matrix Frequencies

•Observed: the frequency of an amino acid at a position respective to the tyrosine (-4...Y...4) within a FLT3 substrate

•Expected (background): the frequency of an amino acid from the protein sequence of a substrate

Virtual Peptide Library Generation

•Generator: generates a peptide library using the probability matrix scores

•Amino acid are considered abundant if they are two standard deviations from the mean

Screener: Scores the generated virtual peptide library against a panel of kinases

•Sequences that score positive for FLT3 will be used as potential artificial substrates

FIGURE 4

| Amino Acid | -4 | -3 | -2 | -1 | 0 | 1 | 2 | 3 | 4 |
|---|---|---|---|---|---|---|---|---|---|
| A | 0.07 | -0.02 | 0.69 | 1.20 | -2.87 | 0.45 | -0.48 | 0.68 | -0.05 |
| C | 1.15 | -0.34 | | 0.49 | -1.37 | 0.64 | 1.08 | -0.36 | 0.67 |
| D | 3.04 | 2.13 | 1.50 | 3.17 | -3.27 | -0.05 | 1.48 | -0.89 | -1.09 |
| E | 0.42 | 1.43 | 0.73 | -0.23 | -2.60 | 0.39 | -0.60 | -1.34 | -0.64 |
| F | -0.52 | -1.18 | -1.46 | -0.58 | -2.48 | 0.57 | 1.10 | 0.72 | 0.48 |
| G | 0.19 | 0.24 | 0.43 | -0.51 | -2.29 | 0.00 | -0.16 | 0.02 | 0.79 |
| H | -0.76 | 1.00 | 0.26 | 2.82 | -2.18 | 1.78 | 0.42 | 0.25 | -0.08 |
| I | -0.11 | -0.95 | | -0.19 | -2.72 | -0.39 | -0.68 | 0.75 | -0.05 |
| K | -0.67 | -0.50 | -1.30 | -2.01 | -2.30 | -0.90 | -1.48 | -0.89 | -1.41 |
| L | -0.53 | -0.91 | -1.54 | -1.05 | -3.36 | -1.20 | -0.60 | 0.72 | 0.01 |
| M | -0.53 | -0.86 | -1.03 | -1.04 | -2.14 | -0.73 | -1.20 | -0.72 | 0.08 |
| N | -0.30 | 0.07 | 1.06 | 3.56 | -2.66 | 0.64 | 2.32 | 0.15 | 1.08 |
| P | -0.39 | -0.21 | | -0.88 | -2.00 | -1.60 | 0.13 | 1.14 | 0.15 |
| Q | -0.92 | 0.12 | 0.18 | 0.87 | -2.51 | 1.69 | 1.10 | 0.18 | 0.09 |
| R | -0.19 | -0.48 | -1.06 | -1.90 | -2.17 | -1.41 | -1.18 | -0.72 | -0.64 |
| S | 0.25 | 1.37 | 1.64 | -0.23 | -2.51 | 0.82 | 0.97 | 0.32 | 0.27 |
| T | 0.46 | -0.25 | | 0.34 | -3.24 | 0.46 | 0.70 | 0.37 | 0.51 |
| V | -0.34 | -1.00 | 0.97 | 1.20 | -3.23 | 1.11 | -0.32 | 0.87 | 0.35 |
| W | -0.85 | -0.10 | | -0.38 | -1.36 | -0.38 | -0.62 | -0.87 | 0.63 |
| Y | 0.49 | -0.42 | 0.18 | 0.15 | 67.23 | 1.03 | 0.67 | -0.58 | 0.69 |

FIGURE 5A

| | -4 | -3 | -2 | -1 | 0 | 1 | 2 | 3 | 4 | |
|---|---|---|---|---|---|---|---|---|---|---|
| | D | D | D | D | Y | Q | N | P | N | |
| | | | S | H | | H | | | | |
| | | | N | N | | V | | | | |

Motif Table
Enter residues per position, -4 to +4, with >2 std. dev. from Substrate Informatics Sheet file "Standard Deviation - Table 1"

FIGURE 5B

Combinations:

| | | |
|---|---|---|
| DDDDYQNPN | DDSDYHNPN | DDNDYVNPN |
| DDDDYHNPN | DDSDYVNPN | DDNHYQNPN |
| DDDDYVNPN | DDSHYQNPN | DDNHYHNPN |
| DDDHYQNPN | DDSHYHNPN | DDNHYVNPN |
| DDDHYHNPN | DDSHYVNPN | DDNNYQNPN |
| DDDHYVNPN | DDSNYQNPN | DDNNYHNPN |
| DDDNYQNPN | DDSNYHNPN | DDNNYVNPN |
| DDDNYHNPN | DDSNYVNPN | B |
| DDDNYVNPN | DDNDYQNPN | |
| DDSDYQNPN | DDNDYHNPN | |

Peptide Identifications

FIGURE 9

| FLT3-WT 2H KALIP | | | | | | | | | |
|---|---|---|---|---|---|---|---|---|---|
| Amino Acid | -4 | -3 | -2 | -1 | 0 | 1 | 2 | 3 | 4 |
| A | 0.59 | 0.44 | 0.57 | -0.11 | -2.71 | 0.70 | 0.08 | -1.04 | -0.15 |
| C | 0.33 | -0.39 | 0.28 | 0.16 | -1.19 | 0.92 | 0.49 | 0.16 | 0.33 |
| D | *3.87* | *4.21* | *3.29* | *2.96* | -2.90 | -1.13 | 0.21 | -1.96 | -0.27 |
| E | 1.00 | *2.23* | 0.77 | 0.54 | -2.51 | -0.07 | -0.24 | -2.01 | -0.62 |
| F | -0.64 | -0.90 | -1.42 | -0.52 | -2.45 | *3.46* | 0.81 | 1.86 | 0.27 |
| G | 0.32 | 0.40 | 0.53 | -0.34 | -2.18 | -0.64 | -0.76 | -0.90 | 0.13 |
| H | -0.36 | -0.74 | -1.19 | *2.09* | -2.19 | 1.04 | 0.60 | -1.28 | -0.72 |
| I | -0.21 | -0.37 | -0.73 | 1.30 | -2.83 | 1.07 | 0.49 | 1.94 | -0.74 |
| K | -1.88 | -1.52 | -1.81 | -2.01 | -2.17 | -1.44 | -1.65 | -0.87 | -0.71 |
| L | -0.12 | -1.41 | -1.48 | -0.35 | -3.18 | -0.42 | 0.63 | *2.21* | 0.07 |
| M | -1.18 | -2.00 | -1.55 | -2.18 | -2.54 | -1.12 | -0.78 | -1.50 | -1.37 |
| N | 1.13 | 1.86 | 1.49 | *2.44* | -2.79 | -0.40 | *2.46* | -1.02 | 0.26 |
| P | -0.75 | -1.09 | 0.54 | -0.90 | -2.05 | -1.69 | -0.37 | 0.87 | 0.01 |
| Q | -0.18 | 0.68 | 1.01 | 0.40 | -2.33 | 0.65 | 1.24 | -0.43 | 1.36 |
| R | -1.96 | -1.97 | -2.03 | -1.99 | -2.03 | -0.90 | -1.47 | 0.47 | 0.24 |
| S | *2.24* | 1.51 | 1.73 | -0.58 | -2.50 | 0.14 | 1.12 | -0.54 | 0.98 |
| T | -0.04 | 1.17 | 0.84 | 1.75 | -3.26 | -0.34 | 0.54 | 0.82 | 1.34 |
| V | -0.60 | -1.03 | 0.61 | 1.25 | -3.49 | 1.57 | 0.03 | *3.70* | -0.07 |
| W | -1.15 | -1.15 | -1.15 | -0.84 | -1.15 | -0.85 | 0.27 | 0.48 | -0.60 |
| Y | -0.45 | -0.47 | -0.67 | 1.90 | *71.71* | *3.80* | 0.38 | 0.65 | -0.31 |

FIGURE 10

| FLT3 WT OVERNIGHT KALIP | | | | | | | | | |
|---|---|---|---|---|---|---|---|---|---|
| Amino Acid | -4 | -3 | -2 | -1 | 0 | 1 | 2 | 3 | 4 |
| A | 0.22 | 0.87 | 0.44 | 0.20 | -2.69 | 0.04 | -0.34 | -0.29 | -0.18 |
| C | 0.20 | -0.30 | -0.19 | -0.13 | -1.34 | 0.37 | 0.41 | 0.20 | 0.30 |
| D | 2.32 | 1.75 | 1.99 | 2.19 | -2.85 | -0.26 | 0.15 | -0.91 | -0.20 |
| E | 0.00 | 0.82 | 0.26 | 0.12 | -2.40 | -0.18 | 0.00 | -1.10 | -0.51 |
| F | -0.10 | -0.29 | -0.98 | -0.57 | -2.55 | 0.57 | 0.07 | 0.13 | -0.10 |
| G | 0.48 | 0.17 | 0.54 | 0.09 | -2.32 | 0.28 | -0.39 | -0.32 | 0.52 |
| H | -0.18 | 0.11 | -0.14 | 1.54 | -2.15 | 0.39 | -0.18 | -0.36 | -0.26 |
| I | 0.19 | -0.57 | -0.29 | 0.29 | -2.70 | 0.78 | -0.27 | 0.64 | -0.25 |
| K | -1.82 | -1.73 | -1.95 | -1.96 | -2.09 | -0.79 | -1.30 | -0.97 | -0.46 |
| L | 0.00 | -0.49 | -0.75 | -0.26 | -3.32 | -0.97 | -0.06 | 1.07 | 0.10 |
| M | -0.80 | -1.58 | -0.98 | -1.30 | -2.32 | -0.85 | -0.72 | -0.97 | -1.14 |
| N | 0.88 | 1.20 | 0.90 | 2.34 | -2.90 | -0.16 | 1.83 | -0.07 | 1.01 |
| P | 0.57 | -0.15 | 0.47 | -0.53 | -1.88 | -0.84 | 0.60 | 1.01 | 0.68 |
| Q | 0.15 | 0.35 | 0.65 | 0.98 | -2.37 | 0.39 | 0.87 | -0.03 | 0.26 |
| R | -2.04 | -2.12 | -2.19 | -2.22 | -2.22 | -0.60 | -1.04 | -0.01 | -0.17 |
| S | 1.01 | 1.39 | 1.25 | 0.10 | -2.55 | 0.39 | 0.53 | 0.32 | 0.09 |
| T | 0.48 | 0.34 | 1.10 | 0.37 | -3.28 | 0.59 | 0.81 | 1.22 | -0.10 |
| V | -0.37 | 0.20 | 0.65 | 0.56 | -3.37 | 0.74 | 0.46 | 0.98 | -0.15 |
| W | -0.80 | -0.63 | -0.99 | -0.58 | -1.18 | -0.61 | -0.01 | -0.51 | 0.19 |
| Y | 0.70 | 1.24 | 0.99 | 2.66 | 69.08 | 2.69 | 0.90 | 0.68 | 0.66 |

FIGURE 11

| FLT3-D835Y OVERNIGHT KALIP | | | | | | | | | |
|---|---|---|---|---|---|---|---|---|---|
| Amino Acid | -4 | -3 | -2 | -1 | 0 | 1 | 2 | 3 | 4 |
| A | 0.06 | 0.64 | 0.47 | 0.55 | -2.92 | -0.28 | -0.26 | -0.14 | -0.16 |
| C | 0.41 | -0.21 | -0.27 | -0.14 | -1.36 | 0.21 | 0.37 | 0.17 | 0.22 |
| D | 1.86 | 1.20 | 1.75 | *2.03* | -2.93 | 0.34 | 0.05 | -0.90 | -0.21 |
| E | 0.29 | 0.37 | 0.32 | -0.25 | -2.68 | 0.02 | 0.13 | -1.01 | -0.27 |
| F | -0.34 | -0.18 | -0.71 | -0.49 | -2.53 | -0.31 | 0.20 | 0.02 | 0.10 |
| G | 0.46 | 0.32 | 0.61 | 0.20 | -2.30 | 0.41 | -0.09 | -0.14 | 0.23 |
| H | 0.09 | 0.74 | -0.33 | 1.51 | -2.23 | 0.65 | 0.27 | 0.00 | -0.31 |
| I | 0.64 | -0.68 | -0.24 | 0.38 | -2.85 | -0.09 | 0.11 | 0.11 | -0.53 |
| K | -2.06 | -1.81 | -2.07 | -2.12 | -2.24 | -0.64 | -1.24 | -1.00 | -0.46 |
| L | -0.24 | -0.39 | -0.70 | -0.34 | -3.32 | -0.46 | -0.31 | 0.59 | 0.18 |
| M | -0.29 | -1.01 | -1.13 | -1.05 | -2.27 | -0.92 | -0.93 | -0.73 | -1.24 |
| N | 0.58 | 1.12 | 1.25 | 1.81 | -2.89 | -0.19 | 1.34 | -0.38 | 1.09 |
| P | 0.27 | -0.15 | 0.35 | -0.30 | -1.84 | -0.86 | 0.43 | 0.88 | 0.58 |
| Q | -0.15 | 0.29 | 0.42 | 0.89 | -2.47 | 0.06 | 0.82 | 0.15 | 0.01 |
| R | -1.97 | -1.99 | -2.08 | -2.14 | -2.14 | -0.41 | -1.02 | -0.22 | -0.02 |
| S | 0.79 | 1.45 | 0.57 | -0.02 | -2.61 | 0.18 | 0.26 | 0.40 | -0.03 |
| T | 0.51 | 0.06 | 0.86 | 0.13 | -3.19 | 0.22 | 0.41 | 1.18 | 0.44 |
| V | 0.13 | 0.37 | 1.23 | 0.64 | -3.46 | 0.53 | 0.01 | 0.53 | -0.70 |
| W | -0.47 | -0.39 | -0.90 | -0.65 | -1.21 | -0.67 | -0.39 | -0.49 | -0.07 |
| Y | 1.85 | *2.45* | *2.17* | *3.72* | *73.26* | *3.96* | *2.18* | 1.88 | 1.39 |

FIGURE 12

| FLT3-ITD OVERNIGHT KALIP | | | | | | | | | |
|---|---|---|---|---|---|---|---|---|---|
| Amino Acid | -4 | -3 | -2 | -1 | 0 | 1 | 2 | 3 | 4 |
| A | 0.19 | 0.01 | -0.15 | -0.50 | -2.93 | 1.65 | 0.20 | -1.08 | -0.35 |
| C | -0.29 | -0.49 | 1.08 | 0.05 | -1.18 | 0.77 | -0.16 | -0.13 | -0.31 |
| D | 5.22 | 3.50 | 4.35 | 4.04 | -2.76 | -2.03 | 0.47 | -2.13 | -0.85 |
| E | 1.28 | 3.56 | 0.60 | 0.31 | -2.48 | 0.28 | 1.35 | -1.74 | -0.26 |
| F | -0.61 | -1.29 | -1.51 | -1.22 | -2.44 | 2.40 | 1.17 | 1.92 | -0.29 |
| G | 0.30 | 0.00 | -0.86 | -0.39 | -2.14 | -0.64 | -1.06 | -0.86 | 0.29 |
| H | -1.13 | -0.92 | -1.18 | 1.53 | -2.26 | 0.86 | 0.04 | 0.10 | 0.33 |
| I | -0.87 | -1.54 | -1.16 | 1.68 | -2.80 | 1.80 | 0.37 | 1.99 | -0.70 |
| K | -2.08 | -1.77 | -1.85 | -2.14 | -2.22 | -1.35 | -1.80 | -1.10 | -0.71 |
| L | -0.67 | -1.13 | -1.08 | -0.11 | -2.81 | -0.46 | -0.34 | 2.39 | -0.53 |
| M | -1.18 | -1.36 | -2.04 | -1.80 | -2.04 | -1.57 | -1.04 | -1.27 | -1.76 |
| N | 0.88 | 2.57 | 1.34 | 1.92 | -2.65 | -1.14 | 2.11 | -1.49 | 1.18 |
| P | -0.18 | -1.14 | 0.76 | -0.83 | -1.88 | -1.68 | -0.14 | 1.49 | 0.46 |
| Q | -0.44 | 2.02 | 1.02 | 1.45 | -2.25 | 0.74 | 1.24 | -0.28 | 1.49 |
| R | -1.96 | -1.83 | -1.96 | -1.96 | -1.96 | -1.41 | -1.29 | -0.28 | 0.53 |
| S | 1.21 | 0.49 | 2.03 | -0.64 | -2.15 | -0.13 | 0.81 | -0.25 | 0.15 |
| T | 0.78 | 1.73 | 1.86 | 1.77 | -3.16 | -0.27 | 0.83 | 0.74 | 0.69 |
| V | -0.61 | -1.20 | 1.55 | 0.31 | -3.37 | 1.93 | 0.78 | 3.68 | 0.05 |
| W | -1.20 | -1.20 | -1.20 | -0.40 | -1.20 | -0.41 | -0.37 | 0.52 | 0.21 |
| Y | 1.31 | 0.24 | -1.39 | 2.72 | 66.18 | 5.65 | -0.43 | -0.16 | 0.75 |

FIGURE 13

| | | | | Motif Table | | | | | | |
|---|---|---|---|---|---|---|---|---|---|---|
| Enter residues per position, -4 to +4, with >2 std. dev. from Substrate Informatics Sheet file "Standard Deviation - Table 1" | | | | | | | | | | |
| | -4 | -3 | -2 | -1 | 0 | 1 | 2 | 3 | 4 | |
| | D | D | D | D | Y | I | N | V | N | |
| | | N | N | N | | V | | T | | |
| | | | S | H | | F | | P | | |
| | | | | I | | A | | | | |

FIGURE 14

| | | | | | | |
|---|---|---|---|---|---|---|
| DDDDYINVN | DDDIYANVN | DDNIYFNVN | DNDIYVNVN | DNNIYINVN | DSDHYANVN | DSNHYFNVN |
| DDDDYINTN | DDDIYANTN | DDNIYFNTN | DNDIYVNTN | DNNIYINTN | DSDHYANTN | DSNHYFNTN |
| DDDDYINPN | DDDIYANPN | DDNIYFNPN | DNDIYVNPN | DNNIYINPN | DSDHYANPN | DSNHYFNPN |
| DDDDYVNVN | DDNDYINVN | DDNIYANVN | DNDIYFNVN | DNNIYVNVN | DSDIYINVN | DSNHYANVN |
| DDDDYVNTN | DDNDYINTN | DDNIYANTN | DNDIYFNTN | DNNIYVNTN | DSDIYINTN | DSNHYANTN |
| DDDDYVNPN | DDNDYINPN | DDNIYANPN | DNDIYFNPN | DNNIYVNPN | DSDIYINPN | DSNHYANPN |
| DDDDYFNVN | DDNDYVNVN | DNDDYINVN | DNDIYANVN | DNNIYFNVN | DSDIYVNVN | DSNIYINVN |
| DDDDYFNTN | DDNDYVNTN | DNDDYINTN | DNDIYANTN | DNNIYFNTN | DSDIYVNTN | DSNIYINTN |
| DDDDYFNPN | DDNDYVNPN | DNDDYINPN | DNDIYANPN | DNNIYFNPN | DSDIYVNPN | DSNIYINPN |
| DDDDYANVN | DDNDYFNVN | DNDDYVNVN | DNNDYINVN | DNNIYANVN | DSDIYFNVN | DSNIYVNVN |
| DDDDYANTN | DDNDYFNTN | DNDDYVNTN | DNNDYINTN | DNNIYANTN | DSDIYFNTN | DSNIYVNTN |
| DDDDYANPN | DDNDYFNPN | DNDDYVNPN | DNNDYINPN | DNNIYANPN | DSDIYFNPN | DSNIYVNPN |
| DDDNYINVN | DDNDYANVN | DNDDYFNVN | DNNDYVNVN | DSDDYINVN | DSDIYANVN | DSNIYFNVN |
| DDDNYINTN | DDNDYANTN | DNDDYFNTN | DNNDYVNTN | DSDDYINTN | DSDIYANTN | DSNIYFNTN |
| DDDNYINPN | DDNDYANPN | DNDDYFNPN | DNNDYVNPN | DSDDYINPN | DSDIYANPN | DSNIYFNPN |
| DDDNYVNVN | DDNNYINVN | DNDDYANVN | DNNDYFNVN | DSDDYVNVN | DSNDYINVN | DSNIYANVN |
| DDDNYVNTN | DDNNYINTN | DNDDYANTN | DNNDYFNTN | DSDDYVNTN | DSNDYINTN | DSNIYANTN |
| DDDNYVNPN | DDNNYVNVN | DNDDYANPN | DNNDYFNPN | DSDDYVNPN | DSNDYINPN | DSNIYANPN |
| DDDNYFNVN | DDNNYVNTN | DNDNYINVN | DNNDYANVN | DSDDYFNVN | DSNDYVNVN | |
| DDDNYFNTN | DDNNYVNPN | DNDNYINTN | DNNDYANTN | DSDDYFNTN | DSNDYVNTN | |
| DDDNYFNPN | DDNNYFNVN | DNDNYINPN | DNNDYANPN | DSDDYFNPN | DSNDYVNPN | |
| DDDNYANVN | DDNNYFNTN | DNDNYVNVN | DNNNYINVN | DSDDYANVN | DSNDYFNVN | |
| DDDNYANTN | DDNNYFNPN | DNDNYVNTN | DNNNYINTN | DSDDYANTN | DSNDYFNTN | |
| DDDNYANPN | DDNNYANVN | DNDNYVNPN | DNNNYINPN | DSDDYANPN | DSNDYFNPN | |
| DDDHYINVN | DDNNYANPN | DNDNYFNVN | DNNNYVNVN | DSDNYINVN | DSNDYANVN | |

FIGURE 14 (CONTINUED)

| | | | | |
|---|---|---|---|---|
| DDDHYINTN | DDNNYANTN | DNDNYFNTN | DNNNYVNTN | DSDNYINTN | DSNDYANTN |
| DDDHYINPN | DDNNYANPN | DNDNYFNPN | DNNNYVNPN | DSDNYINPN | DSNDYANPN |
| DDDHYVNVN | DDNHYINVN | DNDNYANVN | DNNNYFNVN | DSDNYVNVN | DSNNYINVN |
| DDDHYVNTN | DDNHYINTN | DNDNYANTN | DNNNYFNTN | DSDNYVNTN | DSNNYINTN |
| DDDHYVNPN | DDNHYINPN | DNDNYANPN | DNNNYFNPN | DSDNYVNPN | DSNNYINPN |
| DDDHYFNVN | DDNHYVNVN | DNDHYINVN | DNNNYANVN | DSDNYFNVN | DSNNYVNVN |
| DDDHYFNTN | DDNHYVNTN | DNDHYINTN | DNNNYANTN | DSDNYFNTN | DSNNYVNTN |
| DDDHYFNPN | DDNHYVNPN | DNDHYINPN | DNNNYANPN | DSDNYFNPN | DSNNYVNPN |
| DDDHYANVN | DDNHYFNVN | DNDHYVNVN | DNNHYINVN | DSDNYANVN | DSNNYFNVN |
| DDDHYANTN | DDNHYFNTN | DNDHYVNTN | DNNHYINTN | DSDNYANTN | DSNNYFNTN |
| DDDHYANPN | DDNHYFNPN | DNDHYVNPN | DNNHYINPN | DSDNYANPN | DSNNYFNPN |
| DDDIYINVN | DDNHYANVN | DNDHYFNVN | DNNHYVNVN | DSDHYINVN | DSNNYANVN |
| DDDIYINTN | DDNHYANTN | DNDHYFNTN | DNNHYVNTN | DSDHYINTN | DSNNYANTN |
| DDDIYINPN | DDNHYANPN | DNDHYFNPN | DNNHYVNPN | DSDHYINPN | DSNNYANPN |
| DDDIYVNVN | DDNIYINVN | DNDHYANVN | DNNHYFNVN | DSDHYVNVN | DSNHYINVN |
| DDDIYVNTN | DDNIYINTN | DNDHYANTN | DNNHYFNTN | DSDHYVNTN | DSNHYINTN |
| DDDIYVNPN | DDNIYINPN | DNDHYANPN | DNNHYFNPN | DSDHYVNPN | DSNHYINPN |
| DDDIYFNVN | DDNIYVNVN | DNDIYINVN | DNNHYANVN | DSDHYFNVN | DSNHYVNVN |
| DDDIYFNTN | DDNIYVNTN | DNDIYINTN | DNNHYANTN | DSDHYFNTN | DSNHYVNTN |
| DDDIYFNPN | DDNIYVNPN | DNDIYINPN | DNNHYANPN | DSDHYFNPN | DSNHYVNPN |

FIGURE 15

| Sub. | Sequence | Positional Matrix Scores ||||| Kinase Activity |||
|---|---|---|---|---|---|---|---|---|
| | | WT-2HR | WT | D835Y | ITD | WT | D835Y | ITD |
| FL-Abltide | EAIYAAPFAKKBGGCGAPTYSPPPPGGRKKRRQRRLL | 45.3 | 29.6 | 28.7 | 55.6 | +++ | +++ | ++ |
| A | GGDEDSDNYFNFNEEGGBGG | 94.4 | 82.0 | 70.8 | 94.8 | + | ++++ | + |
| B | GGDEDSDIYFNPNEEGGBGG | 91.4 | 80.3 | 71.2 | 94.4 | ++ | +++++ | ++ |
| C | GGDEDSDNYFNPNEEGGBGG | 93.1 | 86.9 | 78.0 | 94.8 | - | ++++ | + |
| D | GGDEDNDNYCNPNEEGGBGG | 91.2 | 86.4 | 80.6 | 96.0 | - | + | - |
| E | GGDEDSDDYFNPNEEGGBGG | 93.6 | 86.7 | 78.7 | 96.3 | - | + | - |
| F | GGDEDSNDYFNTNEEGGBGG | 90.2 | 81.7 | 75.4 | 91.3 | - | + | - |
| G | GGDEDSDIYANPNEEGGBGG | 84.6 | 77.1 | 71.8 | 93.0 | - | + | - |
| H | GGDEDHNQYEQPNEEGGBGG | 45.3 | 63.3 | 70.4 | 70.2 | - | - | - |
| FLT3tide | FTDRLQQYISTRGGBGG | 1.2 | 4.5 | 3.1 | 0.0 | - | - | - |

FIGURE 16

| Enter Target Kinase: FLT3 | Abl | Arg | Btk | Csk | Fyn | Hck | JAK2 | Lck | Lyn | Pyk2 | Src | Syk | Yes | SCREEN SUM | With Non-specific Activity |
|---|---|---|---|---|---|---|---|---|---|---|---|---|---|---|---|
| Enter Sequences from Generator: | PMS | PMS | PMS | PMS | PMS | PMS | PMS | PMS | PMS | PMS | PMS | PMS | PMS | PMS | |
| DSDNYFNFN | 0.0007 | 0.4049 | 0.0008 | 0.0687 | 3.4917 | 4.9524 | 0.2742 | 0.0493 | 2.6529 | 2.8407 | 31.133 | 1.6545 | 1.4866 | 49.0104 | 1 |
| DSDIYFNPN | 0.0447 | 2.9998 | 3.8618 | 0.448 | 4.3552 | 17.0928 | 2.7427 | 48.9678 | 41.695 | 55.7462 | 73.9717 | 16.7021 | 40.5575 | 309.1853 | 4 |
| DSDNYFNPN | 0.0022 | 2.3113 | 0.0211 | 0.0108 | 0.3728 | 3.3511 | 38.3303 | 0.0448 | 2.919 | 6.8385 | 10.6967 | 19.6046 | 1.9477 | 83.0998 | 0 |
| DNDNYCNPN | 0.2043 | 6.5808 | 0.162 | 0.0379 | 0.5987 | 0.1885 | 1.8317 | 0.0017 | 74.9793 | 0.4148 | 9.8302 | 36.2837 | 1.8325 | 132.7576 | 0 |
| DSDDYFNPN | 0.0058 | 0.1244 | 0.356 | 0.0265 | 0.222 | 0.9703 | 84.5051 | 3.4547 | 7.5086 | 2.1965 | 47.4752 | 78.4169 | 5.0143 | 229.306 | 3 |
| DSNDYFNTN | 0.0007 | 0.001 | 0 | 0.0595 | 0.1724 | 0.0496 | 27.1619 | 0.0074 | 0.8572 | 0 | 6.0996 | 22.2354 | 0.2564 | 0.0007 | 0 |
| DSDIYANPN | 13.1516 | 24.3543 | 4.1322 | 0.362 | 72.1772 | 23.9487 | 0.0033 | 49.95 | 98.9104 | 49.9778 | 84.8853 | 94.0551 | 98.4299 | 590.3891 | 7 |
| DHNQYEQPN | 2.9654 | 0.4498 | 0.0437 | 6.9472 | 19.7202 | 0.288 | 0 | 0.0125 | 0.0891 | 0.0874 | 0.0404 | 5.3567 | 1.0241 | 36.7365 | 0 |

SEQUENCE LISTING

<160> NUMBER OF SEQ ID NOS: 377

<210> SEQ ID NO 1
<211> LENGTH: 9
<212> TYPE: PRT
<213> ORGANISM: Artificial Sequence -continued

```
<220> FEATURE:
<223> OTHER INFORMATION: Description of Artificial Sequence: Synthetic
      peptide

<400> SEQUENCE: 1

Asp Asp Asp Asp Tyr Ile Asn Val Asn
1               5

<210> SEQ ID NO 2
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Asp Asp Asp Asp Tyr Ile Asn Thr Asn
1               5

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Asp Asp Asp Asp Tyr Ile Asn Pro Asn
1               5

<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Asp Asp Asp Asp Tyr Val Asn Val Asn
1               5

<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Asp Asp Asp Asp Tyr Val Asn Thr Asn
1               5

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Asp Asp Asp Asp Tyr Val Asn Pro Asn
1               5
```

```
<210> SEQ ID NO 7
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Asp Asp Asp Asp Tyr Phe Asn Val Asn
1               5

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Asp Asp Asp Asp Tyr Phe Asn Thr Asn
1               5

<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Asp Asp Asp Asp Tyr Phe Asn Pro Asn
1               5

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Asp Asp Asp Asp Tyr Ala Asn Val Asn
1               5

<210> SEQ ID NO 11
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Asp Asp Asp Asp Tyr Ala Asn Thr Asn
1               5

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 12

Asp Asp Asp Asp Tyr Ala Asn Pro Asn
1               5

<210> SEQ ID NO 13
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Asp Asp Asp Asn Tyr Ile Asn Val Asn
1               5

<210> SEQ ID NO 14
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Asp Asp Asp Asn Tyr Ile Asn Thr Asn
1               5

<210> SEQ ID NO 15
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Asp Asp Asp Asn Tyr Ile Asn Pro Asn
1               5

<210> SEQ ID NO 16
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Asp Asp Asp Asn Tyr Val Asn Val Asn
1               5

<210> SEQ ID NO 17
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Asp Asp Asp Asn Tyr Val Asn Thr Asn
1               5

<210> SEQ ID NO 18
<211> LENGTH: 9
<212> TYPE: PRT

<213> ORGANISM: Artificial Sequence
<220> FEATURE:
<223> OTHER INFORMATION: Description of Artificial Sequence: Synthetic
      peptide

<400> SEQUENCE: 18

Asp Asp Asp Asn Tyr Val Asn Pro Asn
1               5

<210> SEQ ID NO 19
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Asp Asp Asp Asn Tyr Phe Asn Val Asn
1               5

<210> SEQ ID NO 20
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Asp Asp Asp Asn Tyr Phe Asn Thr Asn
1               5

<210> SEQ ID NO 21
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Asp Asp Asp Asn Tyr Phe Asn Pro Asn
1               5

<210> SEQ ID NO 22
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Asp Asp Asp Asn Tyr Ala Asn Val Asn
1               5

<210> SEQ ID NO 23
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Asp Asp Asp Asn Tyr Ala Asn Thr Asn
1               5

```
<210> SEQ ID NO 24
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Asp Asp Asp Asn Tyr Ala Asn Pro Asn
1               5

<210> SEQ ID NO 25
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Asp Asp Asp His Tyr Ile Asn Val Asn
1               5

<210> SEQ ID NO 26
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Asp Asp Asp His Tyr Ile Asn Thr Asn
1               5

<210> SEQ ID NO 27
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Asp Asp Asp His Tyr Ile Asn Pro Asn
1               5

<210> SEQ ID NO 28
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Asp Asp Asp His Tyr Val Asn Val Asn
1               5

<210> SEQ ID NO 29
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 29

Asp Asp Asp His Tyr Val Asn Thr Asn
1               5

<210> SEQ ID NO 30
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Asp Asp Asp His Tyr Val Asn Pro Asn
1               5

<210> SEQ ID NO 31
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Asp Asp Asp His Tyr Phe Asn Val Asn
1               5

<210> SEQ ID NO 32
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Asp Asp Asp His Tyr Phe Asn Thr Asn
1               5

<210> SEQ ID NO 33
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Asp Asp Asp His Tyr Phe Asn Pro Asn
1               5

<210> SEQ ID NO 34
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Asp Asp Asp His Tyr Ala Asn Val Asn
1               5

<210> SEQ ID NO 35
<211> LENGTH: 9

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Asp Asp Asp His Tyr Ala Asn Thr Asn
1               5

<210> SEQ ID NO 36
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Asp Asp Asp His Tyr Ala Asn Pro Asn
1               5

<210> SEQ ID NO 37
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Asp Asp Asp Ile Tyr Ile Asn Val Asn
1               5

<210> SEQ ID NO 38
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Asp Asp Asp Ile Tyr Ile Asn Thr Asn
1               5

<210> SEQ ID NO 39
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Asp Asp Asp Ile Tyr Ile Asn Pro Asn
1               5

<210> SEQ ID NO 40
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Asp Asp Asp Ile Tyr Val Asn Val Asn
```

```
<210> SEQ ID NO 41
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Asp Asp Asp Ile Tyr Val Asn Thr Asn
1               5

<210> SEQ ID NO 42
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Asp Asp Asp Ile Tyr Val Asn Pro Asn
1               5

<210> SEQ ID NO 43
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Asp Asp Asp Ile Tyr Phe Asn Val Asn
1               5

<210> SEQ ID NO 44
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Asp Asp Asp Ile Tyr Phe Asn Thr Asn
1               5

<210> SEQ ID NO 45
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Asp Asp Asp Ile Tyr Phe Asn Pro Asn
1               5

<210> SEQ ID NO 46
<211> LENGTH: 9
<212> TYPE: PRT
<213> ORGANISM: Artificial Sequence
<220> FEATURE:
<223> OTHER INFORMATION: Description of Artificial Sequence: Synthetic
```

```
              peptide

<400> SEQUENCE: 46

Asp Asp Asp Ile Tyr Ala Asn Val Asn
1               5

<210> SEQ ID NO 47
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Asp Asp Asp Ile Tyr Ala Asn Thr Asn
1               5

<210> SEQ ID NO 48
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Asp Asp Asp Ile Tyr Ala Asn Pro Asn
1               5

<210> SEQ ID NO 49
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Asp Asp Asn Asp Tyr Ile Asn Val Asn
1               5

<210> SEQ ID NO 50
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Asp Asp Asn Asp Tyr Ile Asn Thr Asn
1               5

<210> SEQ ID NO 51
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Asp Asp Asn Asp Tyr Ile Asn Pro Asn
1               5

<210> SEQ ID NO 52
```

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Asp Asp Asn Asp Tyr Val Asn Val Asn
1               5

<210> SEQ ID NO 53
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Asp Asp Asn Asp Tyr Val Asn Thr Asn
1               5

<210> SEQ ID NO 54
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Asp Asp Asn Asp Tyr Val Asn Pro Asn
1               5

<210> SEQ ID NO 55
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Asp Asp Asn Asp Tyr Phe Asn Val Asn
1               5

<210> SEQ ID NO 56
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Asp Asp Asn Asp Tyr Phe Asn Thr Asn
1               5

<210> SEQ ID NO 57
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57
```

Asp Asp Asn Asp Tyr Phe Asn Pro Asn
1               5

<210> SEQ ID NO 58
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Asp Asp Asn Asp Tyr Ala Asn Val Asn
1               5

<210> SEQ ID NO 59
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Asp Asp Asn Asp Tyr Ala Asn Thr Asn
1               5

<210> SEQ ID NO 60
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Asp Asp Asn Asp Tyr Ala Asn Pro Asn
1               5

<210> SEQ ID NO 61
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Asp Asp Asn Asn Tyr Ile Asn Val Asn
1               5

<210> SEQ ID NO 62
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Asp Asp Asn Asn Tyr Ile Asn Thr Asn
1               5

<210> SEQ ID NO 63
<211> LENGTH: 9
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 63

Asp Asp Asn Asn Tyr Ile Asn Pro Asn
1               5

<210> SEQ ID NO 64
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Asp Asp Asn Asn Tyr Val Asn Val Asn
1               5

<210> SEQ ID NO 65
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Asp Asp Asn Asn Tyr Val Asn Thr Asn
1               5

<210> SEQ ID NO 66
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Asp Asp Asn Asn Tyr Val Asn Pro Asn
1               5

<210> SEQ ID NO 67
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Asp Asp Asn Asn Tyr Phe Asn Val Asn
1               5

<210> SEQ ID NO 68
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Asp Asp Asn Asn Tyr Phe Asn Thr Asn
1               5
```

```
<210> SEQ ID NO 69
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Asp Asp Asn Asn Tyr Phe Asn Pro Asn
1               5

<210> SEQ ID NO 70
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Asp Asp Asn Asn Tyr Ala Asn Val Asn
1               5

<210> SEQ ID NO 71
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Asp Asp Asn Asn Tyr Ala Asn Thr Asn
1               5

<210> SEQ ID NO 72
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Asp Asp Asn Asn Tyr Ala Asn Pro Asn
1               5

<210> SEQ ID NO 73
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Asp Asp Asn His Tyr Ile Asn Val Asn
1               5

<210> SEQ ID NO 74
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74
```

Asp Asp Asn His Tyr Ile Asn Thr Asn
1               5

<210> SEQ ID NO 75
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Asp Asp Asn His Tyr Ile Asn Pro Asn
1               5

<210> SEQ ID NO 76
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Asp Asp Asn His Tyr Val Asn Val Asn
1               5

<210> SEQ ID NO 77
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Asp Asp Asn His Tyr Val Asn Thr Asn
1               5

<210> SEQ ID NO 78
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Asp Asp Asn His Tyr Val Asn Pro Asn
1               5

<210> SEQ ID NO 79
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Asp Asp Asn His Tyr Phe Asn Val Asn
1               5

<210> SEQ ID NO 80
<211> LENGTH: 9
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 80

Asp Asp Asn His Tyr Phe Asn Thr Asn
1               5

<210> SEQ ID NO 81
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Asp Asp Asn His Tyr Phe Asn Pro Asn
1               5

<210> SEQ ID NO 82
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Asp Asp Asn His Tyr Ala Asn Val Asn
1               5

<210> SEQ ID NO 83
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Asp Asp Asn His Tyr Ala Asn Thr Asn
1               5

<210> SEQ ID NO 84
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Asp Asp Asn His Tyr Ala Asn Pro Asn
1               5

<210> SEQ ID NO 85
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Asp Asp Asn Ile Tyr Ile Asn Val Asn
1               5
```

<210> SEQ ID NO 86
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Asp Asp Asn Ile Tyr Ile Asn Thr Asn
1               5

<210> SEQ ID NO 87
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Asp Asp Asn Ile Tyr Ile Asn Pro Asn
1               5

<210> SEQ ID NO 88
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Asp Asp Asn Ile Tyr Val Asn Val Asn
1               5

<210> SEQ ID NO 89
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Asp Asp Asn Ile Tyr Val Asn Thr Asn
1               5

<210> SEQ ID NO 90
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Asp Asp Asn Ile Tyr Val Asn Pro Asn
1               5

<210> SEQ ID NO 91
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 91

Asp Asp Asn Ile Tyr Phe Asn Val Asn
1               5

<210> SEQ ID NO 92
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Asp Asp Asn Ile Tyr Phe Asn Thr Asn
1               5

<210> SEQ ID NO 93
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Asp Asp Asn Ile Tyr Phe Asn Pro Asn
1               5

<210> SEQ ID NO 94
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Asp Asp Asn Ile Tyr Ala Asn Val Asn
1               5

<210> SEQ ID NO 95
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Asp Asp Asn Ile Tyr Ala Asn Thr Asn
1               5

<210> SEQ ID NO 96
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Asp Asp Asn Ile Tyr Ala Asn Pro Asn
1               5

<210> SEQ ID NO 97
<211> LENGTH: 9
<212> TYPE: PRT
```

<213> ORGANISM: Artificial Sequence
<220> FEATURE:
<223> OTHER INFORMATION: Description of Artificial Sequence: Synthetic peptide

<400> SEQUENCE: 97

Asp Asn Asp Asp Tyr Ile Asn Val Asn
1               5

<210> SEQ ID NO 98
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 98

Asp Asn Asp Asp Tyr Ile Asn Thr Asn
1               5

<210> SEQ ID NO 99
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 99

Asp Asn Asp Asp Tyr Ile Asn Pro Asn
1               5

<210> SEQ ID NO 100
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 100

Asp Asn Asp Asp Tyr Val Asn Val Asn
1               5

<210> SEQ ID NO 101
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 101

Asp Asn Asp Asp Tyr Val Asn Thr Asn
1               5

<210> SEQ ID NO 102
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 102

Asp Asn Asp Asp Tyr Val Asn Pro Asn
1               5

<210> SEQ ID NO 103
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Asp Asn Asp Asp Tyr Phe Asn Val Asn
1               5

<210> SEQ ID NO 104
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Asp Asn Asp Asp Tyr Phe Asn Thr Asn
1               5

<210> SEQ ID NO 105
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Asp Asn Asp Asp Tyr Phe Asn Pro Asn
1               5

<210> SEQ ID NO 106
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Asp Asn Asp Asp Tyr Ala Asn Val Asn
1               5

<210> SEQ ID NO 107
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Asp Asn Asp Asp Tyr Ala Asn Thr Asn
1               5

<210> SEQ ID NO 108
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Asp Asn Asp Asp Tyr Ala Asn Pro Asn
1               5

<210> SEQ ID NO 109
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Asp Asn Asp Asn Tyr Ile Asn Val Asn
1               5

<210> SEQ ID NO 110
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Asp Asn Asp Asn Tyr Ile Asn Thr Asn
1               5

<210> SEQ ID NO 111
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Asp Asn Asp Asn Tyr Ile Asn Pro Asn
1               5

<210> SEQ ID NO 112
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Asp Asn Asp Asn Tyr Val Asn Val Asn
1               5

<210> SEQ ID NO 113
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Asp Asn Asp Asn Tyr Val Asn Thr Asn
1               5

<210> SEQ ID NO 114
<211> LENGTH: 9

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Asp Asn Asp Asn Tyr Val Asn Pro Asn
1               5

<210> SEQ ID NO 115
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Asp Asn Asp Asn Tyr Phe Asn Val Asn
1               5

<210> SEQ ID NO 116
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Asp Asn Asp Asn Tyr Phe Asn Thr Asn
1               5

<210> SEQ ID NO 117
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Asp Asn Asp Asn Tyr Phe Asn Pro Asn
1               5

<210> SEQ ID NO 118
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Asp Asn Asp Asn Tyr Ala Asn Val Asn
1               5

<210> SEQ ID NO 119
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Asp Asn Asp Asn Tyr Ala Asn Thr Asn
```

```
1               5

<210> SEQ ID NO 120
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Asp Asn Asp Asn Tyr Ala Asn Pro Asn
1               5

<210> SEQ ID NO 121
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Asp Asn Asp His Tyr Ile Asn Val Asn
1               5

<210> SEQ ID NO 122
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Asp Asn Asp His Tyr Ile Asn Thr Asn
1               5

<210> SEQ ID NO 123
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Asp Asn Asp His Tyr Ile Asn Pro Asn
1               5

<210> SEQ ID NO 124
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Asp Asn Asp His Tyr Val Asn Val Asn
1               5

<210> SEQ ID NO 125
<211> LENGTH: 9
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 125

Asp Asn Asp His Tyr Val Asn Thr Asn
1               5

<210> SEQ ID NO 126
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Asp Asn Asp His Tyr Val Asn Pro Asn
1               5

<210> SEQ ID NO 127
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Asp Asn Asp His Tyr Phe Asn Val Asn
1               5

<210> SEQ ID NO 128
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Asp Asn Asp His Tyr Phe Asn Thr Asn
1               5

<210> SEQ ID NO 129
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Asp Asn Asp His Tyr Phe Asn Pro Asn
1               5

<210> SEQ ID NO 130
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Asp Asn Asp His Tyr Ala Asn Val Asn
1               5

<210> SEQ ID NO 131

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Asp Asn Asp His Tyr Ala Asn Thr Asn
1               5

<210> SEQ ID NO 132
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Asp Asn Asp His Tyr Ala Asn Pro Asn
1               5

<210> SEQ ID NO 133
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Asp Asn Asp Ile Tyr Ile Asn Val Asn
1               5

<210> SEQ ID NO 134
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Asp Asn Asp Ile Tyr Ile Asn Thr Asn
1               5

<210> SEQ ID NO 135
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Asp Asn Asp Ile Tyr Ile Asn Pro Asn
1               5

<210> SEQ ID NO 136
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136
```

Asp Asn Asp Ile Tyr Val Asn Val Asn
1               5

<210> SEQ ID NO 137
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Asp Asn Asp Ile Tyr Val Asn Thr Asn
1               5

<210> SEQ ID NO 138
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Asp Asn Asp Ile Tyr Val Asn Pro Asn
1               5

<210> SEQ ID NO 139
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Asp Asn Asp Ile Tyr Phe Asn Val Asn
1               5

<210> SEQ ID NO 140
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Asp Asn Asp Ile Tyr Phe Asn Thr Asn
1               5

<210> SEQ ID NO 141
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Asp Asn Asp Ile Tyr Phe Asn Pro Asn
1               5

<210> SEQ ID NO 142
<211> LENGTH: 9
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 142

Asp Asn Asp Ile Tyr Ala Asn Val Asn
1               5

<210> SEQ ID NO 143
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Asp Asn Asp Ile Tyr Ala Asn Thr Asn
1               5

<210> SEQ ID NO 144
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Asp Asn Asp Ile Tyr Ala Asn Pro Asn
1               5

<210> SEQ ID NO 145
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Asp Asn Asn Asp Tyr Ile Asn Val Asn
1               5

<210> SEQ ID NO 146
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Asp Asn Asn Asp Tyr Ile Asn Thr Asn
1               5

<210> SEQ ID NO 147
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Asp Asn Asn Asp Tyr Ile Asn Pro Asn
1               5

```
<210> SEQ ID NO 148
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Asp Asn Asn Asp Tyr Val Asn Val Asn
1               5

<210> SEQ ID NO 149
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Asp Asn Asn Asp Tyr Val Asn Thr Asn
1               5

<210> SEQ ID NO 150
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Asp Asn Asn Asp Tyr Val Asn Pro Asn
1               5

<210> SEQ ID NO 151
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Asp Asn Asn Asp Tyr Phe Asn Val Asn
1               5

<210> SEQ ID NO 152
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Asp Asn Asn Asp Tyr Phe Asn Thr Asn
1               5

<210> SEQ ID NO 153
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153
```

```
Asp Asn Asn Asp Tyr Phe Asn Pro Asn
1               5

<210> SEQ ID NO 154
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Asp Asn Asn Asp Tyr Ala Asn Val Asn
1               5

<210> SEQ ID NO 155
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Asp Asn Asn Asp Tyr Ala Asn Thr Asn
1               5

<210> SEQ ID NO 156
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Asp Asn Asn Asp Tyr Ala Asn Pro Asn
1               5

<210> SEQ ID NO 157
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

Asp Asn Asn Asn Tyr Ile Asn Val Asn
1               5

<210> SEQ ID NO 158
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Asp Asn Asn Asn Tyr Ile Asn Thr Asn
1               5

<210> SEQ ID NO 159
<211> LENGTH: 9
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 159

Asp Asn Asn Asn Tyr Ile Asn Pro Asn
1               5

<210> SEQ ID NO 160
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Asp Asn Asn Asn Tyr Val Asn Val Asn
1               5

<210> SEQ ID NO 161
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

Asp Asn Asn Asn Tyr Val Asn Thr Asn
1               5

<210> SEQ ID NO 162
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

Asp Asn Asn Asn Tyr Val Asn Pro Asn
1               5

<210> SEQ ID NO 163
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

Asp Asn Asn Asn Tyr Phe Asn Val Asn
1               5

<210> SEQ ID NO 164
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Asp Asn Asn Asn Tyr Phe Asn Thr Asn
1               5
```

```
<210> SEQ ID NO 165
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

Asp Asn Asn Asn Tyr Phe Asn Pro Asn
1               5

<210> SEQ ID NO 166
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

Asp Asn Asn Asn Tyr Ala Asn Val Asn
1               5

<210> SEQ ID NO 167
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 167

Asp Asn Asn Asn Tyr Ala Asn Thr Asn
1               5

<210> SEQ ID NO 168
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168

Asp Asn Asn Asn Tyr Ala Asn Pro Asn
1               5

<210> SEQ ID NO 169
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

Asp Asn Asn His Tyr Ile Asn Val Asn
1               5

<210> SEQ ID NO 170
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 170

Asp Asn Asn His Tyr Ile Asn Thr Asn
1               5

<210> SEQ ID NO 171
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171

Asp Asn Asn His Tyr Ile Asn Pro Asn
1               5

<210> SEQ ID NO 172
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

Asp Asn Asn His Tyr Val Asn Val Asn
1               5

<210> SEQ ID NO 173
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

Asp Asn Asn His Tyr Val Asn Thr Asn
1               5

<210> SEQ ID NO 174
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

Asp Asn Asn His Tyr Val Asn Pro Asn
1               5

<210> SEQ ID NO 175
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

Asp Asn Asn His Tyr Phe Asn Val Asn
1               5

<210> SEQ ID NO 176
<211> LENGTH: 9
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 176

Asp Asn Asn His Tyr Phe Asn Thr Asn
1               5

<210> SEQ ID NO 177
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 177

Asp Asn Asn His Tyr Phe Asn Pro Asn
1               5

<210> SEQ ID NO 178
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178

Asp Asn Asn His Tyr Ala Asn Val Asn
1               5

<210> SEQ ID NO 179
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

Asp Asn Asn His Tyr Ala Asn Thr Asn
1               5

<210> SEQ ID NO 180
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 180

Asp Asn Asn His Tyr Ala Asn Pro Asn
1               5

<210> SEQ ID NO 181
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 181

Asp Asn Asn Ile Tyr Ile Asn Val Asn
1               5
```

<210> SEQ ID NO 182
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

Asp Asn Asn Ile Tyr Ile Asn Thr Asn
1               5

<210> SEQ ID NO 183
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183

Asp Asn Asn Ile Tyr Ile Asn Pro Asn
1               5

<210> SEQ ID NO 184
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

Asp Asn Asn Ile Tyr Val Asn Val Asn
1               5

<210> SEQ ID NO 185
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 185

Asp Asn Asn Ile Tyr Val Asn Thr Asn
1               5

<210> SEQ ID NO 186
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 186

Asp Asn Asn Ile Tyr Val Asn Pro Asn
1               5

<210> SEQ ID NO 187
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide -continued

```
<400> SEQUENCE: 187

Asp Asn Asn Ile Tyr Phe Asn Val Asn
1               5

<210> SEQ ID NO 188
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 188

Asp Asn Asn Ile Tyr Phe Asn Thr Asn
1               5

<210> SEQ ID NO 189
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 189

Asp Asn Asn Ile Tyr Phe Asn Pro Asn
1               5

<210> SEQ ID NO 190
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 190

Asp Asn Asn Ile Tyr Ala Asn Val Asn
1               5

<210> SEQ ID NO 191
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 191

Asp Asn Asn Ile Tyr Ala Asn Thr Asn
1               5

<210> SEQ ID NO 192
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 192

Asp Asn Asn Ile Tyr Ala Asn Pro Asn
1               5

<210> SEQ ID NO 193
<211> LENGTH: 9
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 193

Asp Ser Asp Asp Tyr Ile Asn Val Asn
1               5

<210> SEQ ID NO 194
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 194

Asp Ser Asp Asp Tyr Ile Asn Thr Asn
1               5

<210> SEQ ID NO 195
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 195

Asp Ser Asp Asp Tyr Ile Asn Pro Asn
1               5

<210> SEQ ID NO 196
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 196

Asp Ser Asp Asp Tyr Val Asn Val Asn
1               5

<210> SEQ ID NO 197
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 197

Asp Ser Asp Asp Tyr Val Asn Thr Asn
1               5

<210> SEQ ID NO 198
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 198

Asp Ser Asp Asp Tyr Val Asn Pro Asn
```

```
<210> SEQ ID NO 199
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 199

Asp Ser Asp Asp Tyr Phe Asn Val Asn
1               5

<210> SEQ ID NO 200
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 200

Asp Ser Asp Asp Tyr Phe Asn Thr Asn
1               5

<210> SEQ ID NO 201
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 201

Asp Ser Asp Asp Tyr Phe Asn Pro Asn
1               5

<210> SEQ ID NO 202
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 202

Asp Ser Asp Asp Tyr Ala Asn Val Asn
1               5

<210> SEQ ID NO 203
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 203

Asp Ser Asp Asp Tyr Ala Asn Thr Asn
1               5

<210> SEQ ID NO 204
<211> LENGTH: 9
<212> TYPE: PRT
<213> ORGANISM: Artificial Sequence
<220> FEATURE:
<223> OTHER INFORMATION: Description of Artificial Sequence: Synthetic
```

```
                    peptide

<400> SEQUENCE: 204

Asp Ser Asp Asp Tyr Ala Asn Pro Asn
1               5

<210> SEQ ID NO 205
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 205

Asp Ser Asp Asn Tyr Ile Asn Val Asn
1               5

<210> SEQ ID NO 206
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 206

Asp Ser Asp Asn Tyr Ile Asn Thr Asn
1               5

<210> SEQ ID NO 207
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 207

Asp Ser Asp Asn Tyr Ile Asn Pro Asn
1               5

<210> SEQ ID NO 208
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 208

Asp Ser Asp Asn Tyr Val Asn Val Asn
1               5

<210> SEQ ID NO 209
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 209

Asp Ser Asp Asn Tyr Val Asn Thr Asn
1               5

<210> SEQ ID NO 210
```

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 210

Asp Ser Asp Asn Tyr Val Asn Pro Asn
1               5

<210> SEQ ID NO 211
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 211

Asp Ser Asp Asn Tyr Phe Asn Val Asn
1               5

<210> SEQ ID NO 212
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 212

Asp Ser Asp Asn Tyr Phe Asn Thr Asn
1               5

<210> SEQ ID NO 213
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 213

Asp Ser Asp Asn Tyr Phe Asn Pro Asn
1               5

<210> SEQ ID NO 214
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 214

Asp Ser Asp Asn Tyr Ala Asn Val Asn
1               5

<210> SEQ ID NO 215
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 215
```

```
Asp Ser Asp Asn Tyr Ala Asn Thr Asn
1               5
```

<210> SEQ ID NO 216
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 216

```
Asp Ser Asp Asn Tyr Ala Asn Pro Asn
1               5
```

<210> SEQ ID NO 217
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 217

```
Asp Ser Asp His Tyr Ile Asn Val Asn
1               5
```

<210> SEQ ID NO 218
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 218

```
Asp Ser Asp His Tyr Ile Asn Thr Asn
1               5
```

<210> SEQ ID NO 219
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 219

```
Asp Ser Asp His Tyr Ile Asn Pro Asn
1               5
```

<210> SEQ ID NO 220
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 220

```
Asp Ser Asp His Tyr Val Asn Val Asn
1               5
```

<210> SEQ ID NO 221
<211> LENGTH: 9
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 221

Asp Ser Asp His Tyr Val Asn Thr Asn
1               5

<210> SEQ ID NO 222
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 222

Asp Ser Asp His Tyr Val Asn Pro Asn
1               5

<210> SEQ ID NO 223
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 223

Asp Ser Asp His Tyr Phe Asn Val Asn
1               5

<210> SEQ ID NO 224
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 224

Asp Ser Asp His Tyr Phe Asn Thr Asn
1               5

<210> SEQ ID NO 225
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 225

Asp Ser Asp His Tyr Phe Asn Pro Asn
1               5

<210> SEQ ID NO 226
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 226

Asp Ser Asp His Tyr Ala Asn Val Asn
1               5
```

```
<210> SEQ ID NO 227
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 227

Asp Ser Asp His Tyr Ala Asn Thr Asn
1               5

<210> SEQ ID NO 228
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 228

Asp Ser Asp His Tyr Ala Asn Pro Asn
1               5

<210> SEQ ID NO 229
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 229

Asp Ser Asp Ile Tyr Ile Asn Val Asn
1               5

<210> SEQ ID NO 230
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 230

Asp Ser Asp Ile Tyr Ile Asn Thr Asn
1               5

<210> SEQ ID NO 231
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 231

Asp Ser Asp Ile Tyr Ile Asn Pro Asn
1               5

<210> SEQ ID NO 232
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 232
```

```
Asp Ser Asp Ile Tyr Val Asn Val Asn
1               5

<210> SEQ ID NO 233
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 233

Asp Ser Asp Ile Tyr Val Asn Thr Asn
1               5

<210> SEQ ID NO 234
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 234

Asp Ser Asp Ile Tyr Val Asn Pro Asn
1               5

<210> SEQ ID NO 235
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 235

Asp Ser Asp Ile Tyr Phe Asn Val Asn
1               5

<210> SEQ ID NO 236
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 236

Asp Ser Asp Ile Tyr Phe Asn Thr Asn
1               5

<210> SEQ ID NO 237
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 237

Asp Ser Asp Ile Tyr Phe Asn Pro Asn
1               5

<210> SEQ ID NO 238
<211> LENGTH: 9
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 238

Asp Ser Asp Ile Tyr Ala Asn Val Asn
1               5

<210> SEQ ID NO 239
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 239

Asp Ser Asp Ile Tyr Ala Asn Thr Asn
1               5

<210> SEQ ID NO 240
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 240

Asp Ser Asp Ile Tyr Ala Asn Pro Asn
1               5

<210> SEQ ID NO 241
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 241

Asp Ser Asn Asp Tyr Ile Asn Val Asn
1               5

<210> SEQ ID NO 242
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 242

Asp Ser Asn Asp Tyr Ile Asn Thr Asn
1               5

<210> SEQ ID NO 243
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 243

Asp Ser Asn Asp Tyr Ile Asn Pro Asn
1               5
```

```
<210> SEQ ID NO 244
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 244

Asp Ser Asn Asp Tyr Val Asn Val Asn
1               5

<210> SEQ ID NO 245
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 245

Asp Ser Asn Asp Tyr Val Asn Thr Asn
1               5

<210> SEQ ID NO 246
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 246

Asp Ser Asn Asp Tyr Val Asn Pro Asn
1               5

<210> SEQ ID NO 247
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 247

Asp Ser Asn Asp Tyr Phe Asn Val Asn
1               5

<210> SEQ ID NO 248
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 248

Asp Ser Asn Asp Tyr Phe Asn Thr Asn
1               5

<210> SEQ ID NO 249
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 249

Asp Ser Asn Asp Tyr Phe Asn Pro Asn
1               5

<210> SEQ ID NO 250
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 250

Asp Ser Asn Asp Tyr Ala Asn Val Asn
1               5

<210> SEQ ID NO 251
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 251

Asp Ser Asn Asp Tyr Ala Asn Thr Asn
1               5

<210> SEQ ID NO 252
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 252

Asp Ser Asn Asp Tyr Ala Asn Pro Asn
1               5

<210> SEQ ID NO 253
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 253

Asp Ser Asn Asn Tyr Ile Asn Val Asn
1               5

<210> SEQ ID NO 254
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 254

Asp Ser Asn Asn Tyr Ile Asn Thr Asn
1               5

<210> SEQ ID NO 255
<211> LENGTH: 9
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 255

Asp Ser Asn Asn Tyr Ile Asn Pro Asn
1               5

<210> SEQ ID NO 256
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 256

Asp Ser Asn Asn Tyr Val Asn Val Asn
1               5

<210> SEQ ID NO 257
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 257

Asp Ser Asn Asn Tyr Val Asn Thr Asn
1               5

<210> SEQ ID NO 258
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 258

Asp Ser Asn Asn Tyr Val Asn Pro Asn
1               5

<210> SEQ ID NO 259
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 259

Asp Ser Asn Asn Tyr Phe Asn Val Asn
1               5

<210> SEQ ID NO 260
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 260

Asp Ser Asn Asn Tyr Phe Asn Thr Asn
1               5
```

```
<210> SEQ ID NO 261
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 261

Asp Ser Asn Asn Tyr Phe Asn Pro Asn
1               5

<210> SEQ ID NO 262
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 262

Asp Ser Asn Asn Tyr Ala Asn Val Asn
1               5

<210> SEQ ID NO 263
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 263

Asp Ser Asn Asn Tyr Ala Asn Thr Asn
1               5

<210> SEQ ID NO 264
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 264

Asp Ser Asn Asn Tyr Ala Asn Pro Asn
1               5

<210> SEQ ID NO 265
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 265

Asp Ser Asn His Tyr Ile Asn Val Asn
1               5

<210> SEQ ID NO 266
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 266

Asp Ser Asn His Tyr Ile Asn Thr Asn
1               5

<210> SEQ ID NO 267
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 267

Asp Ser Asn His Tyr Ile Asn Pro Asn
1               5

<210> SEQ ID NO 268
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 268

Asp Ser Asn His Tyr Val Asn Val Asn
1               5

<210> SEQ ID NO 269
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 269

Asp Ser Asn His Tyr Val Asn Thr Asn
1               5

<210> SEQ ID NO 270
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 270

Asp Ser Asn His Tyr Val Asn Pro Asn
1               5

<210> SEQ ID NO 271
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 271

Asp Ser Asn His Tyr Phe Asn Val Asn
1               5

<210> SEQ ID NO 272
<211> LENGTH: 9
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 272

Asp Ser Asn His Tyr Phe Asn Thr Asn
1               5

<210> SEQ ID NO 273
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 273

Asp Ser Asn His Tyr Phe Asn Pro Asn
1               5

<210> SEQ ID NO 274
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 274

Asp Ser Asn His Tyr Ala Asn Val Asn
1               5

<210> SEQ ID NO 275
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 275

Asp Ser Asn His Tyr Ala Asn Thr Asn
1               5

<210> SEQ ID NO 276
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 276

Asp Ser Asn His Tyr Ala Asn Pro Asn
1               5

<210> SEQ ID NO 277
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 277

Asp Ser Asn Ile Tyr Ile Asn Val Asn
```

```
1               5
```

<210> SEQ ID NO 278
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 278

```
Asp Ser Asn Ile Tyr Ile Asn Thr Asn
1               5
```

<210> SEQ ID NO 279
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 279

```
Asp Ser Asn Ile Tyr Ile Asn Pro Asn
1               5
```

<210> SEQ ID NO 280
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 280

```
Asp Ser Asn Ile Tyr Val Asn Val Asn
1               5
```

<210> SEQ ID NO 281
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 281

```
Asp Ser Asn Ile Tyr Val Asn Thr Asn
1               5
```

<210> SEQ ID NO 282
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 282

```
Asp Ser Asn Ile Tyr Val Asn Pro Asn
1               5
```

<210> SEQ ID NO 283
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 283

Asp Ser Asn Ile Tyr Phe Asn Val Asn
1               5

<210> SEQ ID NO 284
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 284

Asp Ser Asn Ile Tyr Phe Asn Thr Asn
1               5

<210> SEQ ID NO 285
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 285

Asp Ser Asn Ile Tyr Phe Asn Pro Asn
1               5

<210> SEQ ID NO 286
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 286

Asp Ser Asn Ile Tyr Ala Asn Val Asn
1               5

<210> SEQ ID NO 287
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 287

Asp Ser Asn Ile Tyr Ala Asn Thr Asn
1               5

<210> SEQ ID NO 288
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 288

Asp Ser Asn Ile Tyr Ala Asn Pro Asn
1               5

<210> SEQ ID NO 289

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 289

Asp Asp Asp Asp Tyr Gln Asn Pro Asn
1               5

<210> SEQ ID NO 290
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 290

Asp Asp Asp Asp Tyr His Asn Pro Asn
1               5

<210> SEQ ID NO 291
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 291

Asp Asp Asp Tyr Val Asn Pro Asn
1               5

<210> SEQ ID NO 292
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 292

Asp Asp Asp His Tyr Gln Asn Pro Asn
1               5

<210> SEQ ID NO 293
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 293

Asp Asp Asp His Tyr His Asn Pro Asn
1               5

<210> SEQ ID NO 294
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 294
```

```
Asp Asp Asp Asn Tyr Gln Asn Pro Asn
1               5

<210> SEQ ID NO 295
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 295

Asp Asp Asp Asn Tyr His Asn Pro Asn
1               5

<210> SEQ ID NO 296
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 296

Asp Asp Ser Asp Tyr Gln Asn Pro Asn
1               5

<210> SEQ ID NO 297
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 297

Asp Asp Ser Asp Tyr His Asn Pro Asn
1               5

<210> SEQ ID NO 298
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 298

Asp Asp Ser His Tyr Gln Asn Pro Asn
1               5

<210> SEQ ID NO 299
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 299

Asp Asp Ser His Tyr His Asn Pro Asn
1               5

<210> SEQ ID NO 300
<211> LENGTH: 9
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 300

Asp Asp Ser His Val Val Asn Pro Asn
1               5

<210> SEQ ID NO 301
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 301

Asp Asp Ser Asn Tyr Gln Asn Pro Asn
1               5

<210> SEQ ID NO 302
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 302

Asp Asp Ser Asn Tyr His Asn Pro Asn
1               5

<210> SEQ ID NO 303
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 303

Asp Asp Ser Asn Tyr Val Asn Pro Asn
1               5

<210> SEQ ID NO 304
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 304

Asp Asp Asn Asp Tyr Gln Asn Pro Asn
1               5

<210> SEQ ID NO 305
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 305

Asp Asp Asn Asp Tyr His Asn Pro Asn
1               5
```

```
<210> SEQ ID NO 306
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 306

Asp Asp Asn His Tyr Gln Asn Pro Asn
1               5

<210> SEQ ID NO 307
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 307

Asp Asp Asn His Tyr His Asn Pro Asn
1               5

<210> SEQ ID NO 308
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 308

Asp Asp Asn Asn Tyr Gln Asn Pro Asn
1               5

<210> SEQ ID NO 309
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 309

Asp Asp Asn Asn Tyr His Asn Pro Asn
1               5

<210> SEQ ID NO 310
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Asp, Ser or Asn
<220> FEATURE:
<221> NAME/KEY: MOD_RES
<222> LOCATION: (4)..(4)
<223> OTHER INFORMATION: Asp, His, Ile or Asn
<220> FEATURE:
<221> NAME/KEY: MOD_RES
<222> LOCATION: (6)..(6)
<223> OTHER INFORMATION: Gln, His, Ile, Phe, Ala or Val
<220> FEATURE:
<221> NAME/KEY: MOD_RES
<222> LOCATION: (7)..(7)
<223> OTHER INFORMATION: Cys, Asp, Phe, His, Asn, Gln, Ser, Thr or Tyr
```

```
<220> FEATURE:
<221> NAME/KEY: MOD_RES
<222> LOCATION: (8)..(8)
<223> OTHER INFORMATION: Ala, Phe, Gly, His, Ile, Leu, Asn, Pro, Gln,
      Ser, Thr or Val
<220> FEATURE:
<221> NAME/KEY: MOD_RES
<222> LOCATION: (9)..(9)
<223> OTHER INFORMATION: Cys, Phe, Gly, Leu, Met, Asn, Pro, Gln, Ser,
      Thr, Val, Trp or Tyr

<400> SEQUENCE: 310

Asp Xaa Xaa Xaa Tyr Xaa Xaa Xaa Xaa
1               5

<210> SEQ ID NO 311
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Asp, Ser or Asn
<220> FEATURE:
<221> NAME/KEY: MOD_RES
<222> LOCATION: (4)..(4)
<223> OTHER INFORMATION: Asp, His or Asn
<220> FEATURE:
<221> NAME/KEY: MOD_RES
<222> LOCATION: (6)..(6)
<223> OTHER INFORMATION: Gln, His or Val
<220> FEATURE:
<221> NAME/KEY: MOD_RES
<222> LOCATION: (7)..(7)
<223> OTHER INFORMATION: Cys, Asp, Phe, His, Asn, Gln, Ser, Thr or Tyr
<220> FEATURE:
<221> NAME/KEY: MOD_RES
<222> LOCATION: (8)..(8)
<223> OTHER INFORMATION: Ala, Phe, Gly, His, Ile, Leu, Asn, Pro, Gln,
      Ser, Thr or Val
<220> FEATURE:
<221> NAME/KEY: MOD_RES
<222> LOCATION: (9)..(9)
<223> OTHER INFORMATION: Cys, Phe, Gly, Leu, Met, Asn, Pro, Gln, Ser,
      Thr, Val, Trp or Tyr

<400> SEQUENCE: 311

Asp Asp Xaa Xaa Tyr Xaa Xaa Xaa Xaa
1               5

<210> SEQ ID NO 312
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (8)..(8)
```

```
<223> OTHER INFORMATION: Any amino acid

<400> SEQUENCE: 312

Asp Xaa Asp Xaa Tyr Xaa Asn Xaa Asn
1               5

<210> SEQ ID NO 313
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 313

Glu Ala Ile Tyr Ala Ala Pro Phe Ala Lys
1               5                   10

<210> SEQ ID NO 314
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 314

Phe Thr Asp Arg Leu Gln Gln Tyr Ile Ser Thr Arg
1               5                   10

<210> SEQ ID NO 315
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (8)..(8)
<223> OTHER INFORMATION: Any amino acid

<400> SEQUENCE: 315

Asp Ser Asp Xaa Tyr Phe Asn Xaa Asn
1               5

<210> SEQ ID NO 316
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
```

```
<222> LOCATION: (8)..(8)
<223> OTHER INFORMATION: Any amino acid

<400> SEQUENCE: 316

Asp Xaa Asp Xaa Tyr Xaa Asn Xaa Asn
1               5

<210> SEQ ID NO 317
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 317

Asp Ser Asp Asn Tyr Phe Asn Phe Asn
1               5

<210> SEQ ID NO 318
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Asp, Ser or Asn
<220> FEATURE:
<221> NAME/KEY: MOD_RES
<222> LOCATION: (4)..(4)
<223> OTHER INFORMATION: Asp, His or Asn
<220> FEATURE:
<221> NAME/KEY: MOD_RES
<222> LOCATION: (6)..(6)
<223> OTHER INFORMATION: Gln, His or Val

<400> SEQUENCE: 318

Asp Asp Xaa Xaa Tyr Xaa Asn Pro Asn
1               5

<210> SEQ ID NO 319
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Ser or Asn
<220> FEATURE:
<221> NAME/KEY: MOD_RES
<222> LOCATION: (4)..(4)
<223> OTHER INFORMATION: Ile or Asn
<220> FEATURE:
<221> NAME/KEY: MOD_RES
<222> LOCATION: (8)..(8)
<223> OTHER INFORMATION: Phe, Pro or Thr

<400> SEQUENCE: 319

Asp Xaa Asp Xaa Tyr Phe Asn Xaa Asn
1               5

<210> SEQ ID NO 320
<211> LENGTH: 9
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Ile or Asn
<220> FEATURE:
<221> NAME/KEY: MOD_RES
<222> LOCATION: (8)..(8)
<223> OTHER INFORMATION: Phe or Pro

<400> SEQUENCE: 320

Asp Ser Asp Xaa Tyr Phe Asn Xaa Asn
1               5

<210> SEQ ID NO 321
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Asp, Ser or Asn
<220> FEATURE:
<221> NAME/KEY: MOD_RES
<222> LOCATION: (6)..(6)
<223> OTHER INFORMATION: Gln, His, Ile, Phe, Ala or Val
<220> FEATURE:
<221> NAME/KEY: MOD_RES
<222> LOCATION: (7)..(7)
<223> OTHER INFORMATION: Cys, Asp, Phe, His, Asn, Gln, Ser, Thr or Tyr
<220> FEATURE:
<221> NAME/KEY: MOD_RES
<222> LOCATION: (9)..(9)
<223> OTHER INFORMATION: Cys, Phe, Gly, Leu, Met, Asn, Pro, Gln, Ser,
      Thr, Val, Trp or Tyr

<400> SEQUENCE: 321

Asp Xaa Xaa Asn Tyr Xaa Xaa Pro Xaa
1               5

<210> SEQ ID NO 322
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Asp, Ser or Asn
<220> FEATURE:
<221> NAME/KEY: MOD_RES
<222> LOCATION: (6)..(6)
<223> OTHER INFORMATION: Gln, His, Ile, Phe, Ala or Val
<220> FEATURE:
<221> NAME/KEY: MOD_RES
<222> LOCATION: (7)..(7)
<223> OTHER INFORMATION: Cys, Asp, Phe, His, Asn, Gln, Ser, Thr or Tyr
<220> FEATURE:
<221> NAME/KEY: MOD_RES
<222> LOCATION: (8)..(8)
<223> OTHER INFORMATION: Ala, Phe, Gly, His, Ile, Leu, Asn, Gln, Ser,
      Thr or Val
<220> FEATURE:
<221> NAME/KEY: MOD_RES
<222> LOCATION: (9)..(9)
<223> OTHER INFORMATION: Cys, Phe, Gly, Leu, Met, Asn, Pro, Gln, Ser,
      Thr, Val, Trp or Tyr
```

```
<400> SEQUENCE: 322

Asp Xaa Xaa Asn Tyr Xaa Xaa Xaa Xaa
1               5

<210> SEQ ID NO 323
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Asp, Ser or Asn
<220> FEATURE:
<221> NAME/KEY: MOD_RES
<222> LOCATION: (4)..(4)
<223> OTHER INFORMATION: His, Ile or Asn
<220> FEATURE:
<221> NAME/KEY: MOD_RES
<222> LOCATION: (6)..(6)
<223> OTHER INFORMATION: Gln, His, Ile, Phe, Ala or Val
<220> FEATURE:
<221> NAME/KEY: MOD_RES
<222> LOCATION: (7)..(7)
<223> OTHER INFORMATION: Cys, Asp, Phe, His, Asn, Gln, Ser, Thr or Tyr
<220> FEATURE:
<221> NAME/KEY: MOD_RES
<222> LOCATION: (8)..(8)
<223> OTHER INFORMATION: Ala, Phe, Gly, His, Ile, Leu, Asn, Pro, Gln,
      Ser, Thr or Val
<220> FEATURE:
<221> NAME/KEY: MOD_RES
<222> LOCATION: (9)..(9)
<223> OTHER INFORMATION: Cys, Phe, Gly, Leu, Met, Asn, Pro, Gln, Ser,
      Thr, Val, Trp or Tyr

<400> SEQUENCE: 323

Asp Xaa Xaa Xaa Tyr Xaa Xaa Xaa Xaa
1               5

<210> SEQ ID NO 324
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Asp, Ser or Asn
<220> FEATURE:
<221> NAME/KEY: MOD_RES
<222> LOCATION: (4)..(4)
<223> OTHER INFORMATION: Asp, His, Ile or Asn
<220> FEATURE:
<221> NAME/KEY: MOD_RES
<222> LOCATION: (6)..(6)
<223> OTHER INFORMATION: Gln, His, Ile, Phe or Val
<220> FEATURE:
<221> NAME/KEY: MOD_RES
<222> LOCATION: (7)..(7)
<223> OTHER INFORMATION: Cys, Asp, Phe, His, Asn, Gln, Ser, Thr or Tyr
<220> FEATURE:
<221> NAME/KEY: MOD_RES
<222> LOCATION: (8)..(8)
<223> OTHER INFORMATION: Ala, Phe, Gly, His, Ile, Leu, Asn, Pro, Gln,
      Ser, Thr or Val
<220> FEATURE:
<221> NAME/KEY: MOD_RES
<222> LOCATION: (9)..(9)
<223> OTHER INFORMATION: Cys, Phe, Gly, Leu, Met, Asn, Pro, Gln, Ser,
      Thr, Val, Trp or Tyr
```

<400> SEQUENCE: 324

Asp Xaa Xaa Xaa Tyr Xaa Xaa Xaa Xaa
1               5

<210> SEQ ID NO 325
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Asp, Ser or Asn
<220> FEATURE:
<221> NAME/KEY: MOD_RES
<222> LOCATION: (4)..(4)
<223> OTHER INFORMATION: Asp, His or Asn
<220> FEATURE:
<221> NAME/KEY: MOD_RES
<222> LOCATION: (6)..(6)
<223> OTHER INFORMATION: Gln, His or Val

<400> SEQUENCE: 325

Asp Asp Xaa Xaa Tyr Xaa Asn Pro Asn
1               5

<210> SEQ ID NO 326
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 326

Asp Asp Asp Asp Tyr Gln Asn Pro Asn
1               5

<210> SEQ ID NO 327
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 327

Asp Asp Asp Asp Tyr His Asn Pro Asn
1               5

<210> SEQ ID NO 328
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 328

Asp Asp Asp Asp Tyr Val Asn Pro Asn
1               5

<210> SEQ ID NO 329
<211> LENGTH: 9
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 329

Asp Asp Asp His Tyr Gln Asn Pro Asn
1               5

<210> SEQ ID NO 330
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 330

Asp Asp Asp His Tyr His Asn Pro Asn
1               5

<210> SEQ ID NO 331
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 331

Asp Asp Asp His Tyr Val Asn Pro Asn
1               5

<210> SEQ ID NO 332
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 332

Asp Asp Asp Asn Tyr Gln Asn Pro Asn
1               5

<210> SEQ ID NO 333
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 333

Asp Asp Asp Asn Tyr His Asn Pro Asn
1               5

<210> SEQ ID NO 334
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 334

Asp Asp Asp Asn Tyr Val Asn Pro Asn
1               5
```

<210> SEQ ID NO 335
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 335

Asp Asp Ser Asp Tyr Gln Asn Pro Asn
1               5

<210> SEQ ID NO 336
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 336

Asp Asp Ser Asp Tyr His Asn Pro Asn
1               5

<210> SEQ ID NO 337
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 337

Asp Asp Ser Asp Tyr Val Asn Pro Asn
1               5

<210> SEQ ID NO 338
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 338

Asp Asp Ser His Tyr Gln Asn Pro Asn
1               5

<210> SEQ ID NO 339
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 339

Asp Asp Ser His Tyr His Asn Pro Asn
1               5

<210> SEQ ID NO 340
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 340

Asp Asp Ser His Tyr Val Asn Pro Asn
1               5

<210> SEQ ID NO 341
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 341

Asp Asp Ser Asn Tyr Gln Asn Pro Asn
1               5

<210> SEQ ID NO 342
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 342

Asp Asp Ser Asn Tyr His Asn Pro Asn
1               5

<210> SEQ ID NO 343
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 343

Asp Asp Ser Asn Tyr Val Asn Pro Asn
1               5

<210> SEQ ID NO 344
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 344

Asp Asp Asn Asp Tyr Gln Asn Pro Asn
1               5

<210> SEQ ID NO 345
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 345

Asp Asp Asn Asp Tyr His Asn Pro Asn
1               5

<210> SEQ ID NO 346
<211> LENGTH: 9
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 346

Asp Asp Asn Asp Tyr Val Asn Pro Asn
1               5

<210> SEQ ID NO 347
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 347

Asp Asp Asn His Tyr Gln Asn Pro Asn
1               5

<210> SEQ ID NO 348
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 348

Asp Asp Asn His Tyr His Asn Pro Asn
1               5

<210> SEQ ID NO 349
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 349

Asp Asp Asn His Tyr Val Asn Pro Asn
1               5

<210> SEQ ID NO 350
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 350

Asp Asp Asn Asn Tyr Gln Asn Pro Asn
1               5

<210> SEQ ID NO 351
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 351

Asp Asp Asn Asn Tyr His Asn Pro Asn
1               5
```

```
<210> SEQ ID NO 352
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 352

Asp Asp Asn Asn Tyr Val Asn Pro Asn
1               5

<210> SEQ ID NO 353
<211> LENGTH: 11
<212> TYPE: PRT
<213> ORGANISM: Unknown
<220> FEATURE:
<223> OTHER INFORMATION: Description of Unknown:
      AFAP sequence

<400> SEQUENCE: 353

Asn Glu Leu Val Asp Tyr Ile Thr Ile Ser Arg
1               5                   10

<210> SEQ ID NO 354
<211> LENGTH: 11
<212> TYPE: PRT
<213> ORGANISM: Homo sapiens

<400> SEQUENCE: 354

Asp Ser Asp Glu Asp Tyr Glu Lys Val Pro Leu
1               5                   10

<210> SEQ ID NO 355
<211> LENGTH: 11
<212> TYPE: PRT
<213> ORGANISM: Homo sapiens

<400> SEQUENCE: 355

Pro Leu Tyr Glu Glu Tyr Val Val Leu Lys Asn
1               5                   10

<210> SEQ ID NO 356
<211> LENGTH: 11
<212> TYPE: PRT
<213> ORGANISM: Homo sapiens

<400> SEQUENCE: 356

Asp Phe Asp Ser Glu Tyr Gln Glu Leu Trp Asp
1               5                   10

<210> SEQ ID NO 357
<211> LENGTH: 11
<212> TYPE: PRT
<213> ORGANISM: Homo sapiens

<400> SEQUENCE: 357

Met Asn Glu Phe Glu Tyr Leu Lys Leu Leu Gly
1               5                   10

<210> SEQ ID NO 358
<211> LENGTH: 9
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Asp, Asn or Ser
<220> FEATURE:
<221> NAME/KEY: MOD_RES
<222> LOCATION: (3)..(3)
<223> OTHER INFORMATION: Asp or Asn
<220> FEATURE:
<221> NAME/KEY: MOD_RES
<222> LOCATION: (4)..(4)
<223> OTHER INFORMATION: Asp, Asn, His or Ile
<220> FEATURE:
<221> NAME/KEY: MOD_RES
<222> LOCATION: (6)..(6)
<223> OTHER INFORMATION: Ile, Val, Phe or Ala
<220> FEATURE:
<221> NAME/KEY: MOD_RES
<222> LOCATION: (8)..(8)
<223> OTHER INFORMATION: Val, Thr or Pro

<400> SEQUENCE: 358

Asp Xaa Xaa Xaa Tyr Xaa Asn Xaa Asn
1               5

<210> SEQ ID NO 359
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 359

Glu Ala Ile Tyr Ala Ala Pro Phe Ala Lys Lys Lys Gly Gly Cys Gly
1               5                   10                  15

Ala Pro Thr Tyr Ser Pro Pro Pro Pro Gly Gly Arg Lys Lys Arg
            20                  25                  30

Arg Gln Arg Arg Leu Leu
        35

<210> SEQ ID NO 360
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 360

Gly Gly Asp Glu Asp Ser Asp Asn Tyr Phe Asn Phe Asn Glu Glu Gly
1               5                   10                  15

Gly Lys Gly Gly
            20

<210> SEQ ID NO 361
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 361

Gly Gly Asp Glu Asp Ser Asp Ile Tyr Phe Asn Pro Asn Glu Glu Gly
1               5                   10                  15
```

```
Gly Lys Gly Gly
            20

<210> SEQ ID NO 362
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 362

Gly Gly Asp Glu Asp Ser Asp Asn Tyr Phe Asn Pro Asn Glu Glu Gly
1               5                   10                  15

Gly Lys Gly Gly
            20

<210> SEQ ID NO 363
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 363

Gly Gly Asp Glu Asp Asn Asp Asn Tyr Cys Asn Pro Asn Glu Glu Gly
1               5                   10                  15

Gly Lys Gly Gly
            20

<210> SEQ ID NO 364
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 364

Gly Gly Asp Glu Asp Ser Asp Asp Tyr Phe Asn Pro Asn Glu Glu Gly
1               5                   10                  15

Gly Lys Gly Gly
            20

<210> SEQ ID NO 365
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 365

Gly Gly Asp Glu Asp Ser Asn Asp Tyr Phe Asn Thr Asn Glu Glu Gly
1               5                   10                  15

Gly Lys Gly Gly
            20

<210> SEQ ID NO 366
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 366

Gly Gly Asp Glu Asp Ser Asp Ile Tyr Ala Asn Pro Asn Glu Glu Gly
1               5                   10                  15

Gly Lys Gly Gly
            20

<210> SEQ ID NO 367
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 367

Gly Gly Asp Glu Asp His Asn Gln Tyr Glu Gln Pro Asn Glu Glu Gly
1               5                   10                  15

Gly Lys Gly Gly
            20

<210> SEQ ID NO 368
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 368

Phe Thr Asp Arg Leu Gln Gln Tyr Ile Ser Thr Arg Gly Gly Lys Gly
1               5                   10                  15

Gly

<210> SEQ ID NO 369
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 369

Asp Ser Asp Asn Tyr Phe Asn Phe Asn
1               5

<210> SEQ ID NO 370
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 370

Asp Ser Asp Ile Tyr Phe Asn Pro Asn
1               5

<210> SEQ ID NO 371
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

-continued

```
<400> SEQUENCE: 371

Asp Ser Asp Asn Tyr Phe Asn Pro Asn
1               5

<210> SEQ ID NO 372
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 372

Asp Asn Asp Asn Tyr Cys Asn Pro Asn
1               5

<210> SEQ ID NO 373
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 373

Asp Ser Asp Asp Tyr Phe Asn Pro Asn
1               5

<210> SEQ ID NO 374
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 374

Asp Ser Asn Asp Tyr Phe Asn Thr Asn
1               5

<210> SEQ ID NO 375
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 375

Asp Ser Asp Ile Tyr Ala Asn Pro Asn
1               5

<210> SEQ ID NO 376
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 376

Asp His Asn Gln Tyr Glu Gln Pro Asn
1               5

<210> SEQ ID NO 377
<211> LENGTH: 9
<212> TYPE: PRT
<213> ORGANISM: Artificial Sequence
<220> FEATURE:
<223> OTHER INFORMATION: Description of Artificial Sequence: Synthetic
```

```
            peptide
<220> FEATURE:
<221> NAME/KEY: MOD_RES
<222> LOCATION: (2)..(3)
<223> OTHER INFORMATION: Asp, Ser or Asn
<220> FEATURE:
<221> NAME/KEY: MOD_RES
<222> LOCATION: (4)..(4)
<223> OTHER INFORMATION: Asp, His or Ile
<220> FEATURE:
<221> NAME/KEY: MOD_RES
<222> LOCATION: (6)..(6)
<223> OTHER INFORMATION: Gln, His, Ile, Phe, Ala or Val
<220> FEATURE:
<221> NAME/KEY: MOD_RES
<222> LOCATION: (7)..(7)
<223> OTHER INFORMATION: Cys, Asp, Phe, His, Asn, Gln, Ser, Thr or Tyr
<220> FEATURE:
<221> NAME/KEY: MOD_RES
<222> LOCATION: (9)..(9)
<223> OTHER INFORMATION: Cys, Phe, Gly, Leu, Met, Asn, Pro, Gln, Ser,
      Thr, Val, Trp or Tyr

<400> SEQUENCE: 377

Asp Xaa Xaa Xaa Tyr Xaa Xaa Pro Xaa
1               5
```

SUBSTRATES FOR FLT3 KINASE AND USES THEREOF

PRIORITY

This application claims priority to U.S. Provisional Application No. 62/340,384, filed on May 23, 2016, which application is herein incorporated by reference.

SEQUENCE LISTING

The instant application contains a Sequence Listing which has been submitted electronically in ASCII format and is hereby incorporated by reference in its entirety. Said ASCII copy, created on Jun. 30, 2017, is named 09531_420US1_SL.txt and is 91,903 bytes in size.

GOVERNMENT FUNDING

This invention was made with government support under CA186505 awarded by National Institutes of Health. The government has certain rights in the invention.

BACKGROUND

Acute myeloid leukemia (AML) is an aggressive disease that is characterized by an abnormal level of immature myeloblasts in the blood and bone marrow. FLT3 is a receptor tyrosine kinase that plays an integral role in haematopoiesis, and alteration to this cohesive signaling machinery leads to haematopoietic malignancies including AML. In fact, FLT3 is implicated as a major factor in AML relapse (Leick, M. B. & Levis, M. J. Curr. Hematol. Malig. Rep. 1-15 (2017). doi:10.1007/s11899-017-0381-2).

Thirty percent of AML cases have been shown to have mutations to FLT3 causing a conformational change that leads the kinase to be constitutively active (Stirewalt, D. L. & Radich, J. P. Nat. Rev. Cancer 3, 650-65 (2003); and Pozarowski, P. & Darzynkiewicz, Z. Methods Mol. Biol. 281, 301-11 (2004)). Mutations to the juxtamembrane and the kinase domain are the most common types of mutations (Stirewalt, D. L. & Radich, J. P. Nat. Rev. Cancer 3, 650-65 (2003); Leung, A., et al., Nat. Rev. Leuk. 27, 260-268 (2013); and Yamamoto, Y. Blood 97, 2434-2439 (2001)). Internal tandem duplication (ITD) to the juxtamembrane domain or the first TKD occurs when a segment is duplicated (head to tail) leading to the loss of repressive regions of the RTK. Unlike WT FLT3, FLT3-ITD has also been implicated in the up-regulation of the pro-survival STAT5A signaling pathway (Yoshimoto, G. et al. Blood 114, 5034-5044 (2009)). A second common mutation is a point mutation of aspartic acid 835 to a tyrosine residue in the kinase domain (TKD), which also leads to a constitutively active kinase. The ITD and TKD mutants also can activate and dimerize with the wild type (WT) FLT3. The effects of these mutations on FLT3 signaling are still unclear, but one possibility is that mutant FLT3-TKD and FLT3-ITD activate alternative signaling pathways, or activate standard FLT3 pathways aberrantly, compared to the WT.

Early studies have shown that mutations to FLT3 are correlated with poor long-term prognosis (Swords, R., Freeman, C. & Giles, F. Leukemia 26, 2176-2185 (2012); Kim, Y. et al. Nature 5, e336-7 (2015); Hospital, M.-A. et al. Onco. Targets. Ther. 10, 607-615 (2017); and Lagunas-Rangel, F. A. & Chavez-Valencia, V. Oncol. 34, 114 (2017)). Patients with mutations to FLT3 initially achieve similar disease remission to those with the endogenous FLT3 but have an increased risk for relapse (Stirewalt, D. L. & Radich, J. P. Nat. Rev. Cancer 3, 650-65 (2003); Swords, R., Freeman, C. & Giles, F. Leukemia 26, 2176-2185 (2012); Lagunas-Rangel, F. A. & Chavez-Valencia, V. Oncol. 34, 114 (2017); and Smith, C. C., et al., Leukemia 1-3 (2015). doi:10.1038/1eu.2015.165). In vitro studies have shown that FLT3-ITD mutant expressing cell lines induce resistance to cytosine arabinoside, (Ara-C) which is a primary AML, therapeutic (Swords, R., Freeman, C. & Giles, F. Leukemia 26, 2176-2185 (2012)). These findings prompted the use of a combinatorial approach to AML therapies that included both Ara-C and FLT3 inhibitors but, unfortunately, use of FLT3 inhibitors leads to relapse by inducing new TKD mutations (Swords, R., Freeman, C. & Giles, F. Leukemia 26, 2176-2185 (2012); and Hospital, M.-A. et al. Onco. Targets. Ther. 10, 607-615 (2017).

Computational modeling suggests that internal tandem duplication of the juxtamembrane domain or point mutation to aspartic acid 835 (D835Y) both alter the protein structure, leading to decreased potency for some FLT3 inhibitors (Smith, C. C., et al., Leukemia 1-3 (2015). doi:10.1038/1eu.2015.165). Based on this clinical importance, discovery of alternative inhibitors and clinical monitoring of inhibitor efficacy are of interest to physicians treating AML patients with FLT3 overexpression and/or mutations. Assays that could be used in these capacities would therefore be valuable, however existing peptide substrates are either not specific (e.g. the "Abltide" substrate) or not efficiently phosphorylated (e.g. the substrate reported by Böhmer, F.-D. & Uecker, A. Br. J. Haematol. 144, 127-30 (2009), which was poorly phosphorylated in our experience). More optimal peptide substrates would benefit drug discovery and assay development efforts for FLT3 and its variants.

Currently there is a need for agents that are substrates for specific kinases (e.g. FLT3 kinase).

SUMMARY

Compounds that are substrates for FLT3 kinase have been identified. The compounds can be used in assays to determine if FLT3 kinase is active in a system. The compounds can also be used in assays to identify inhibitors of certain kinases (e.g., FLT3 kinase). The compounds can also be utilized in LRET assays similar to those described in United States Patent Application Publication Number US2016/0097084, the content of which is hereby incorporated herein in its entirety.

Accordingly, in one embodiment the invention provides a peptide comprising an amino acid sequence of formula I:

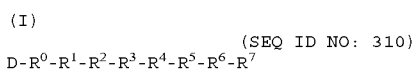

(I)
(SEQ ID NO: 310)
$D-R^0-R^1-R^2-R^3-R^4-R^5-R^6-R^7$ wherein:
$R^0$ is selected from the group consisting of: D, S and N;
$R^1$ is selected from the group consisting of: D, S, and N;
$R^2$ is selected from the group consisting of: D, H, I and N;
$R^3$ is Y;
$R^4$ is selected from the group consisting of: Q, H, I, F, A, and V;
$R^5$ is selected from the group consisting of: C, D, F, H, N, Q, S, T, and Y;
$R^6$ is selected from the group consisting of: A, F, G, H, I, L, N, P, Q, S, T, and V; and
$R^7$ is selected from the group consisting of: C, F, G, L, M, N, P, Q, S, T, V, W, and Y; or a salt thereof.

In one embodiment the invention provides a peptide comprising an amino acid sequence of formula (Ia):

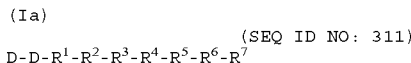
(Ia)
(SEQ ID NO: 311)

wherein:
R$^1$ is selected from the group consisting of: D, S, and N;
R$^2$ is selected from the group consisting of: D, H, and N;
R$^3$ is Y;
R$^4$ is selected from the group consisting of: Q, H, and V;
R$^5$ is selected from the group consisting of: C, D, F, H, N, Q, S, T, and Y;
R$^6$ is selected from the group consisting of: A, F, G, H, I, L, N, P, Q, S, T, and V; and
R$^7$ is selected from the group consisting of: C, F, G, L, M, N, P, Q, S, T, V, W, and Y; or a salt thereof.

In one embodiment the invention provides a peptide comprising an amino acid sequence of formula II:

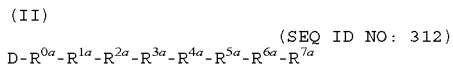
(II)
(SEQ ID NO: 312)

wherein:
R$^{0a}$ is any amino acid;
R$^{1a}$ is D;
R$^{2a}$ is any amino acid;
R$^{3a}$ is Y;
R$^{4a}$ is any amino acid;
R$^{5a}$ is N;
R$^{6a}$ is any amino acid; and
R$^{7a}$ is N;
or a salt thereof.

In one embodiment the invention provides a peptide consisting of an amino acid sequence of formula (I) or formula (II).

The invention also provides a method to identify an inhibitor of FLT3 kinase comprising:
determining whether a test compound disrupts the interaction of FLT3 with a peptide of the invention, wherein a disruption (e.g., competitive binding between the test compound and the described peptide) indicates that the test compound is an inhibitor of FLT3.

The invention also provides a method to determine if FLT3 kinase is active in a system comprising: determining whether a peptide of the invention has served as a substrate for FLT3 activity, wherein such a positive indication of activity indicates that FLT3 is active in the system.

The invention also provides a method to use a peptide of the invention in a LRET assay (e.g. an assay as described in United States Patent Application Publication Number US2016/0097084).

The invention also provides processes and intermediates disclosed herein that are useful for preparing a peptide of Formula (I) or Formula (II) or a salt thereof.

Certain embodiments, of the invention provide a peptide generated using a method described herein.

Certain embodiments of the invention provide a nucleic acid sequence encoding a peptide as described herein.

Certain embodiments of the invention provide an expression cassette comprising a nucleic acid as described herein operably linked to a promoter.

Certain embodiments of the invention provide a vector comprising an expression cassette as described herein.

Certain embodiments of the invention provide a cell comprising a vector as described herein.

The invention also provides a method for detecting the activity of a kinase comprising:
1) contacting the kinase with a peptide as described herein to provide a resulting mixture;
2) contacting the resulting mixture with a lanthanide metal, under conditions such that a luminescent signal from the lanthanide metal is generated; and
3) detecting the luminescent signal, wherein the luminescent signal correlates with the activity of the kinase.

The invention also provides a method to identify an inhibitor of a kinase comprising:
1) contacting a peptide as described in herein, the kinase, and a test compound to provide a resulting mixture;
2) contacting the resulting mixture with a lanthanide metal; and
3) detecting a luminescent signal from the lanthanide metal, wherein the luminescent signal from the lanthanide metal correlates with the ability of the test compound to inhibit to the kinase.

Compositions, Complexes and Kits

Certain embodiments of the invention provide a composition comprising one or more peptides as described herein and a lanthanide metal.

In certain embodiments, the lanthanide metal is selected from the group consisting of La, Ce, Pr, Nd, Pm, Sm, Eu, Gd, Tb, Dy, Ho, Er, Tm, Yb, and Lu. In certain embodiments, the lanthanide metal is Tb.

Certain embodiments of the invention provide a complex comprising one or more peptides as described herein and a lanthanide metal.

In certain embodiments, the lanthanide metal is selected from the group consisting of La, Ce, Pr, Nd, Pm, Sm, Eu, Gd, Tb, Dy, Ho, Er, Tm, Yb, and Lu. In certain embodiments, the lanthanide metal is Tb.

Certain embodiments of the invention provide a kit comprising:
1) a peptide as described herein;
2) a lanthanide metal; and
3) instructions for measuring kinase activity using the peptide and lanthanide metal.

Methods of Use

Certain embodiments of the invention provide a method for detecting the activity of a kinase comprising:
1) contacting the kinase with a complex comprising a peptide as described herein and a lanthanide metal, under conditions such that a luminescent signal from the lanthanide metal is generated; and
2) detecting the luminescent signal, wherein the luminescent signal correlates with the activity of the kinase.

In certain embodiments, the method further comprises comparing the luminescent signal to a reference luminescent signal, wherein a change in the luminescent signal as compared to the reference luminescent signal is indicative of kinase activity.

In certain embodiments, the method further comprises detecting a reference luminescent signal from a lanthanide metal complexed with a peptide as described herein, wherein the peptide is non-phosphorylated.

Certain embodiments of the invention provide a method to identify an inhibitor of a kinase comprising:
1) contacting a complex comprising a peptide as described herein and a lanthanide metal, with the kinase and a test compound; and 2) detecting a luminescent signal from the lanthanide metal, wherein the luminescent signal from the lanthanide metal correlates with the ability of the test compound to inhibit to the kinase.

In certain embodiments, the method further comprises comparing the luminescent signal to a reference luminescent signal, wherein a change in the luminescent signal as compared to the reference luminescent signal indicates the test compound is an inhibitor of the kinase.

In certain embodiments, the method further comprises:
3) contacting a complex comprising a peptide as described herein and a lanthanide metal, with the kinase; and
4) detecting a reference luminescent signal from the lanthanide metal, wherein the reference luminescent signal from the lanthanide metal correlates with the activity of the kinase.

In certain embodiments, the peptide and the test compound competitively bind to the kinase.

Certain embodiments of the invention provide a method to determine if a kinase is active in a system comprising: determining whether a peptide as described herein has served as a substrate for kinase activity, wherein such a positive indication of activity indicates that the kinase is active in the system.

BRIEF DESCRIPTION OF THE FIGURES

FIG. 2A illustrates the number of proteins identified for each treatment group.
FIG. 2B illustrates the numerical differences in unique phosphopeptides identified in each treatment group.
FIG. 3 illustrates KINATEST-ID Workflow.
FIG. 4 illustrates the FLT3's Positional Probability Matrix: Favorable amino acids include: D(−4), D(−3), D(−1), H(−1), N(−1), Y(0), AND N(2); unfavorable amino acids include F(−3), V(−3), F(−2), K-M(−2), R(−2), K-M(−1), R(−1), A-W(0), L(1), P(1), R(1), K(2), M(2), R(2), E(3), D(4), and K(4).

FIGS. 5A-5B illustrate the consensus FLT3 substrate motifs within the KALIP derived substrate dataset
FIG. 5A illustrates how the abundant amino acids were incorporated into the Generator tool's motif table
The amino acids were chosen from FLT3's Positional Probability Matrix
FIG. 5B lists the distinct amino acid sequences generated from the Motif Table in FIG. 5A (FIG. 5A discloses SEQ ID NO: 325 and FIG. 5B discloses SEQ ID NOS 326-352, respectively, in order of columns)
FIG. 6 discloses SEQ ID NOS 353-357, respectively, in order of appearance.
FIG. 9 illustrates the standard deviation values from the positional scoring matrix for FLT3-WT using a 2-hour kinase incubation time from the KALIP technique. An amino acid residue is considered favorable when its value is 2 standard deviations above the mean and is highlighted in gray. An amino acid is considered unfavorable when it is 2 standard deviations below the mean.
FIG. 10 illustrates the standard deviation values from the positional scoring matrix for FLT3-WT using an overnight kinase incubation time from the KALIP technique. An amino acid residue is considered favorable when its value is 2 standard deviations above the mean and is highlighted in gray. An amino acid is considered unfavorable when it is 2 standard deviations below the mean.
FIG. 11 illustrates the standard deviation values from the positional scoring matrix for FLT3-E835Y using an overnight kinase incubation time from the KALIP technique. An amino acid residue is considered favorable when its value is 2 standard deviations above the mean and is highlighted in gray. An amino acid is considered unfavorable when it is 2 standard deviations below the mean.
FIG. 12 illustrates the standard deviation values from the positional scoring matrix for FLT3-ITD using an overnight kinase incubation time from the KALIP technique. An amino acid residue is considered favorable when its value is 2 standard deviations above the mean and is highlighted in gray. An amino acid is considered unfavorable when it is 2 standard deviations below the mean.

FIG. 13 illustrates the amino acid residues that were considered favorable at their respective positions and were used to generate possible sequence permutations. FIG. 13 discloses SEQ ID NO: 358.

FIG. 14 illustrates the 288 different sequence permutations that were generated through the Generator module. Based on the in vitro kinase assay results, it has been shown that aspartic acid (D) is preferred at positions −4 and −2 with respect to the tyrosine. Proline (P) was shown to be preferred at position +3 for FLT3-D835Y and FLT3-ITD to phosphorylate the sequence, while FLT3-WT showed no preference. FIG. 14 discloses SEQ ID NOS 1-288, respectively, in order of columns.

FIG. 15 illustrates Sequences Result Summary details for the FLT3 Artificial Substrate (FAS) candidate sequences synthesized and assayed in vitro with recombinant FLT3 variants. Abltide (EAIYAAPFAK (SEQ ID NO: 313); the substrate has been incorporated with an SH3 recognition and cell penetrating sequence and termed FL-Abltide) is a previously known FLT3 peptide substrate and has been used as a reference substrate to monitor kinase activity. The previously reported Flt3 substrate peptide "Flt3tide" (FTDRLQQYISTR (SEQ ID NO: 314)) (Böhmer, F.-D. & Uecker, A. Br. J. Haematol. 144, 127-30 (2009)) is also included to illustrate enzyme conversion performance improvements for the new substrates relative to this sequence. The "−4 to +4" 9 amino acid substrate sequences derived from the KINATEST-ID pipeline are underlined, and were synthesized within the terbium binding motif shell (amino acids not underlined; sequence chosen using the Aligner module of KINATEST-ID) with a biotinylated lysine (B) as an enrichment tag. The "−4 to +4" portions of the FL-Abltide and Flt3tide substrates are underlined for comparison to the sequences derived from the KINATEST-ID pipeline. Using the top scoring sequence for the 2 hour KALIP kinase incubation as the reference sequence, the amino acid mutations for the remaining sequences are depicted in bold. The candidate sequences were scored against the wild type (WT; 2 hour and overnight kinase incubation), D835Y and ITD bioinformatics. The positional matrix score is a reference value to predict if a peptide sequence will be phosphorylated by its respective kinase. The kinase activity columns summarize the in vitro kinase assay results. If a sequence showed better phosphorylation than FL-Abltide (+++) it was denoted as (++++ or +++++). Sequences are also denoted showing low levels of phosphorylation (+) and no levels of phosphorylation (−). FIG. 15 discloses SEQ ID NOS 359-368, respectively, in order of appearance.

FIG. 16 illustrates the screener positional matrix score (PMS) for each candidate sequence against the original KINATEST-ID kinase panel. The PMS for each peptide is summed and then a prediction is generated. The "non-specific activity" suggestion is generated using data from the published PSMs from the original KINATEST-ID paper, which used positional scanning peptide libraries and previously reported endogenous kinases substrates from proteomic databases. For example, sequence 1 has a screener sum of 80.45 and is predicted not to be a good substrate for any of the "off-target" kinases in the panel, whereas sequence 7 has a score of 590.38 and is predicted to be a good substrate for Fyn, Lck, Lyn, Pyk2, Src, Syk and Yes kinases in addition to FLT3. FIG. 16 discloses SEQ ID NOS 369-376, respectively, in order of appearance.

DETAILED DESCRIPTION

Figure 1:
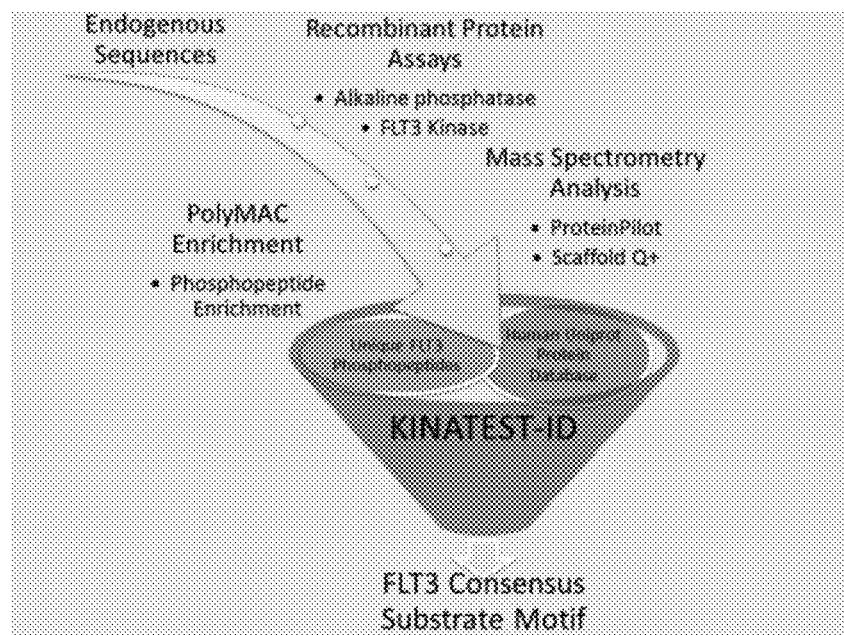
FIG. 1 illustrates a process for identifying proteins and sites that are phosphorylated by FLT3.
1 milligram of KG-1 lysate was subjected to trypsin digestion
1 hour incubation with alkaline phosphatase at 37 degrees Celsius
12 hour incubation with recombinant FLT3 kinase or water (negative control) at 37 degrees Celsius
Phosphopeptides were enriched with Polymer-based Metal-ion Affinity Capture (PolyMAC) enrichment kit
Tymora Analytical Operations PolyMAC-Ti Magnetic Phosphopeptide Enrichment Kit (SKU 700)
Mass Spectrometry Analysis
Samples were analyzed on a Thermo Fisher Orbitrap Fusion over a 2-30%
Figure 2A:
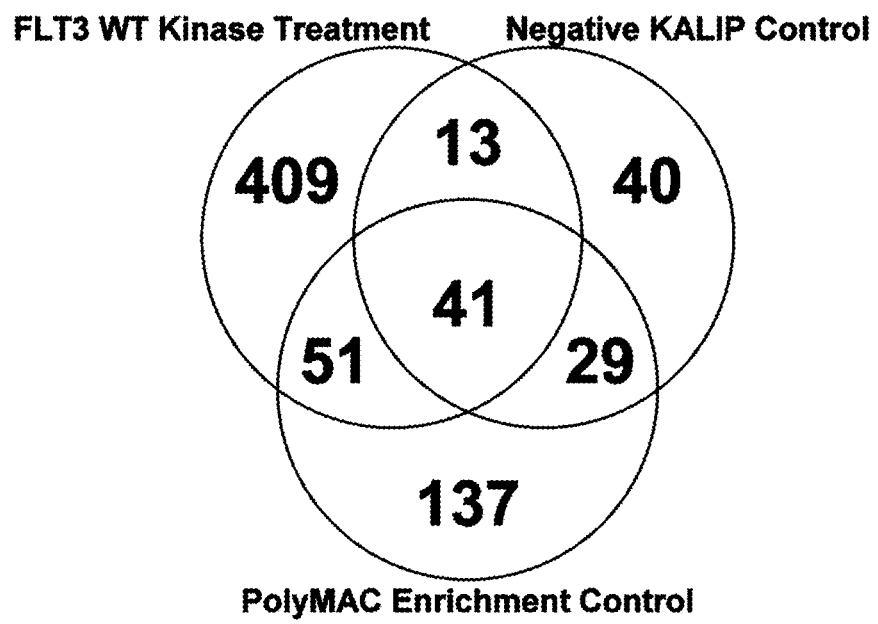
FIGS. 2A-2B illustrate the identification of proteins and phosphorylated peptides using the KALIP approach (www.ncbi.nlm.nih.gov/pubmed/26584932). Mass spectrometer raw files were searched on ProteinPilot 5 software against the human Uniprot database. The ProteinPilot results were then analyzed with Scaffold Q+ software to visualize, validate and interpret the identifications. In Scaffold Q+, the peptide false discovery rate was set at 1% while the protein threshold was set at 99%.
All treatments were carried out side by side
Untreated KG-1 cell lysate (no phosphatase or kinase assays) was used for the PolyMAC Enrichment Control to determine successful phosphopeptide enrichment.
A phosphorylation filter was applied within Scaffold Q+ to ensure proteins and peptides included in the list contained a phosphorylated residue
Figure 2B:
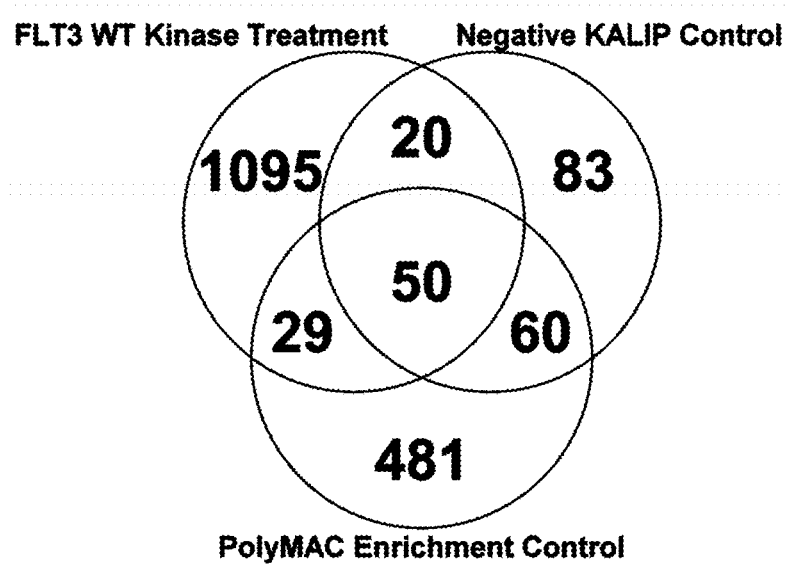

The peptide sequences identified and described herein can be prepared using standard techniques.

The data illustrates that the FLT3 treatment group contains a larger and unique number of identified phosphopeptides from an Orbitrap mass analyzer. Further studies can be carried out in order to attribute the increase in phosphopeptide identifications to FLT3 kinase activity. The data demonstrates that a kinase assay linked with phosphoproteomics (www.ncbi.nlm.nih.gov/-pubmed/26584932) can be used to generate and identify FLT3 substrates in a high throughput manner.

In the peptide sequences described herein standard single letter designators are used for the amino acids (e.g. A for alanine, D for aspartic acid, etc.)

Certain embodiments of the invention provide a peptide comprising an amino acid sequence having about 65% to about 100%, about 70% to about 100%, about 71% to about 100%, about 72% to about 100%, about 73% to about 100%, about 74% to about 100%, about 75% to about 100%, about 76% to about 100%, about 77% to about 100%, about 78% to about 100%, about 79% to about 100%, about 80% to about 100%, about 81% to about 100%, about 82% to about 100%, about 83% to about 100%, about 84% to about 100%, about 85% to about 100%, about 86% to about 100%, about 87% to about 100%, about 88% to about 100%, about 89% to about 100%, about 90% to about 100%, about 91% to about 100%, about 92% to about 100%, about 93% to about 100%, about 94% to about 100%, about 95% to about 100%, about 96% to about 100%, about 97% to about 100% or about 98% to about 100% sequence identity to an amino acid sequence of Formula (I) or Formula (II). In certain embodiments, the peptide comprises an amino acid sequence having about 90%, 91%, 92%, 93%, 94%, 95%, 96%, 97%, 98%, 99% or 100% sequence identity to an amino acid sequence of Formula (I) or Formula (II).

Certain embodiments of the invention provide a peptide consisting of an amino acid sequence having about 65% to about 100%, about 70% to about 100%, about 71% to about 100%, about 72% to about 100%, about 73% to about 100%, about 74% to about 100%, about 75% to about 100%, about 76% to about 100%, about 77% to about 100%, about 78% to about 100%, about 79% to about 100%, about 80% to about 100%, about 81% to about 100%, about 82% to about 100%, about 83% to about 100%, about 84% to about 100%, about 85% to about 100%, about 86% to about 100%, about 8'7% to about 100%, about 88% to about 100%, about 89% to about 100%, about 90% to about 100%, about 91% to about 100%, about 92% to about 100%, about 93% to about 100%, about 94% to about 100%, about 95% to about 100%, about 96% to about 100%, about 97% to about 100% or about 98% to about 100% sequence identity to an amino acid sequence of Formula (I) or Formula (II). In certain embodiments, the peptide consists of an amino acid sequence having about 90%, 91%, 92%, 93%, 94%, 95%, 96%, 97%, 98%, 99% or 100% sequence identity to an amino acid sequence of Formula (I) or Formula (II).

Certain embodiments of the invention provide a peptide comprising an amino acid sequence of formula II:

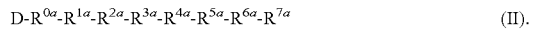

$$D-R^{0a}-R^{1a}-R^{2a}-R^{3a}-R^{4a}-R^{5a}-R^{6a}-R^{7a} \quad (II).$$

In one embodiment $R^{0a}$ is S or N.
In one embodiment $R^{0a}$ is not H.
In one embodiment $R^{2a}$ is N or I.
In one embodiment $R^{2a}$ is not D or Q.
In one embodiment $R^{4a}$ is F.
In one embodiment $R^{4a}$ is not A or C.
In one embodiment $R^{6a}$ is F, P or T.
In one embodiment $R^{0a}$ is S; $R^{1a}$ is D; $R^{2a}$ is any amino acid; $R^{3a}$ is Y; $R^{4a}$ is F; $R^{5a}$ is N; $R^{6a}$ is any amino acid; and $R^{7a}$ is N; or a salt thereof. In one embodiment $R^{2a}$ is N or I. In one embodiment $R^{6a}$ is F or P.

In one embodiment $R^{0a}$ is S or N; $R^{1a}$ is D; $R^{2a}$ is N or I; $R^{3a}$ is Y; $R^{4a}$ is F; $R^{5a}$ is N; $R^{6a}$ is F, P, T; and $R^{7a}$ is N; or a salt thereof.

In one embodiment the invention provides a peptide comprising an amino acid sequence of formula I or formula II wherein at least one amino acid is replaced with a non-natural amino acid or wherein at least one of the amino-terminus or the carboxy-terminus is modified.

Certain embodiments of the invention provide a peptide comprising an amino acid sequence selected from the group consisting of:

DDDDYQNPN, (SEQ ID NO: 289)

DDDDYHNPN, (SEQ ID NO: 290)

DDDYVNPN, (SEQ ID NO: 291)

DDDHYQNPN, (SEQ ID NO: 292)

DDDHYHNPN, (SEQ ID NO: 293)

DDDHYVNPN, (SEQ ID NO: 30)

DDDNYQNPN, (SEQ ID NO: 294)

DDDNYHNPN, (SEQ ID NO: 295)

DDDNYVNPN, (SEQ ID NO: 18)

DDSDYQNPN, (SEQ ID NO: 296)

DDSDYHNPN, (SEQ ID NO: 297)

DDSHYQNPN, (SEQ ID NO: 298)

DDSHYHNPN, (SEQ ID NO: 299)

DDSHVVNPN, (SEQ ID NO: 300)

DDSNYQNPN, (SEQ ID NO: 301)

DDSNYHNPN, (SEQ ID NO: 302)

DDSNYVNPN, (SEQ ID NO: 303)

DDNDYQNPN, (SEQ ID NO: 304)

DDNDYHNPN, (SEQ ID NO: 305)

DDNDYVNPN, (SEQ ID NO: 54)

DDNHYQNPN, (SEQ ID NO: 306)

-continued

DDNHYHNPN, (SEQ ID NO: 307)

DDNHYVNPN, (SEQ ID NO: 78)

DDNNYQNPN, (SEQ ID NO: 308)

DDNNYHNPN, (SEQ ID NO: 309)
and

DDNNYVNPN. (SEQ ID NO: 66)

Certain embodiments of the invention provide a peptide comprising an amino acid sequence selected from the group consisting of:

| | | | | | | |
|---|---|---|---|---|---|---|
| DDDDYINVN (SEQ ID NO: 1) | DDDIYANVN (SEQ ID NO: 46) | DDNIYFNVN (SEQ ID NO: 91) | DNDIYVNVN (SEQ ID NO: 136) | DNNIYINVN (SEQ ID NO: 181) | DSDHYANVN (SEQ ID NO: 226) | DSNHYFNVN (SEQ ID NO: 271) |
| DDDDYINTN (SEQ ID NO: 2) | DDDIYANTN (SEQ ID NO: 47) | DDNIYFNTN (SEQ ID NO: 92) | DNDIYVNTN (SEQ ID NO: 137) | DNNIYINTN (SEQ ID NO: 182) | DSDHYANTN (SEQ ID NO: 227) | DSNHYFNTN (SEQ ID NO: 272) |
| DDDDYINPN (SEQ ID NO: 3) | DDDIYANPN (SEQ ID NO: 48) | DDNIYFNPN (SEQ ID NO: 93) | DNDIYVNPN (SEQ ID NO: 138) | DNNIYINPN (SEQ ID NO: 183) | DSDHYANPN (SEQ ID NO: 228) | DSNHYFNPN (SEQ ID NO: 273) |
| DDDDYVNVN (SEQ ID NO: 4) | DDNDYINVN (SEQ ID NO: 49) | DDNIYANVN (SEQ ID NO: 94) | DNDIYFNVN (SEQ ID NO: 139) | DNNIYVNVN (SEQ ID NO: 184) | DSDIYINVN (SEQ ID NO: 229) | DSNHYANVN (SEQ ID NO: 274) |
| DDDDYVNTN (SEQ ID NO: 5) | DDNDYINTN (SEQ ID NO: 50) | DDNIYANTN (SEQ ID NO: 95) | DNDIYFNTN (SEQ ID NO: 140) | DNNIYVNTN (SEQ ID NO: 185) | DSDIYINTN (SEQ ID NO: 230) | DSNHYANTN (SEQ ID NO: 275) |
| DDDDYVNPN (SEQ ID NO: 6) | DDNDYINPN (SEQ ID NO: 51) | DDNIYANPN (SEQ ID NO: 96) | DNDIYFNPN (SEQ ID NO: 141) | DNNIYVNPN (SEQ ID NO: 186) | DSDIYINPN (SEQ ID NO: 231) | DSNHYANPN (SEQ ID NO: 276) |
| DDDDYFNVN (SEQ ID NO: 7) | DDNDYVNVN (SEQ ID NO: 52) | DNDDYINVN (SEQ ID NO: 97) | DNDIYANVN (SEQ ID NO: 142) | DNNIYFNVN (SEQ ID NO: 187) | DSDIYVNVN (SEQ ID NO: 232) | DSNIYINVN (SEQ ID NO: 277) |
| DDDDYFNTN (SEQ ID NO: 8) | DDNDYVNTN (SEQ ID NO: 53) | DNDDYINTN (SEQ ID NO: 98) | DNDIYANTN (SEQ ID NO: 143) | DNNIYFNTN (SEQ ID NO: 188) | DSDIYVNTN (SEQ ID NO: 233) | DSNIYINTN (SEQ ID NO: 278) |
| DDDDYFNPN (SEQ ID NO: 9) | DDNDYVNPN (SEQ ID NO: 54) | DNDDYINPN (SEQ ID NO: 99) | DNDIYANPN (SEQ ID NO: 144) | DNNIYFNPN (SEQ ID NO: 189) | DSDIYVNPN (SEQ ID NO: 234) | DSNIYINPN (SEQ ID NO: 279) |
| DDDDYANVN (SEQ ID NO: 10) | DDNDYFNVN (SEQ ID NO: 55) | DNDDYVNVN (SEQ ID NO: 100) | DNNDYINVN (SEQ ID NO: 145) | DNNIYANVN (SEQ ID NO: 190) | DSDIYFNVN (SEQ ID NO: 235) | DSNIYVNVN (SEQ ID NO: 280) |
| DDDDYANTN (SEQ ID NO: 11) | DDNDYFNTN (SEQ ID NO: 56) | DNDDYVNTN (SEQ ID NO: 101) | DNNDYINTN (SEQ ID NO: 146) | DNNIYANTN (SEQ ID NO: 191) | DSDIYFNTN (SEQ ID NO: 236) | DSNIYVNTN (SEQ ID NO: 281) |
| DDDDYANPN (SEQ ID NO: 12) | DDNDYFNPN (SEQ ID NO: 57) | DNDDYVNPN (SEQ ID NO: 102) | DNNDYINPN (SEQ ID NO: 147) | DNNIYANPN (SEQ ID NO: 192) | DSDIYFNPN (SEQ ID NO: 237) | DSNIYVNPN (SEQ ID NO: 282) |
| DDDNYINVN (SEQ ID NO: 13) | DDNDYANVN (SEQ ID NO: 58) | DNDDYFNVN (SEQ ID NO: 103) | DNNDYVNVN (SEQ ID NO: 148) | DSDDYINVN (SEQ ID NO: 193) | DSDIYANVN (SEQ ID NO: 238) | DSNIYFNVN (SEQ ID NO: 283) |
| DDDNYINTN (SEQ ID NO: 14) | DDNDYANTN (SEQ ID NO: 59) | DNDDYFNTN (SEQ ID NO: 104) | DNNDYVNTN (SEQ ID NO: 149) | DSDDYINTN (SEQ ID NO: 194) | DSDIYANTN (SEQ ID NO: 239) | DSNIYFNTN (SEQ ID NO: 284) |
| DDDNYINPN (SEQ ID NO: 15) | DDNDYANPN (SEQ ID NO: 60) | DNDDYFNPN (SEQ ID NO: 105) | DNNDYVNPN (SEQ ID NO: 150) | DSDDYINPN (SEQ ID NO: 195) | DSDIYANPN (SEQ ID NO: 240) | DSNIYFNPN (SEQ ID NO: 285) |
| DDDNYVNVN (SEQ ID NO: 16) | DDNNYINVN (SEQ ID NO: 61) | DNDDYANVN (SEQ ID NO: 106) | DNNDYFNVN (SEQ ID NO: 151) | DSDDYVNVN (SEQ ID NO: 196) | DSNDYINVN (SEQ ID NO: 241) | DSNIYANVN (SEQ ID NO: 286) |
| DDDNYVNTN (SEQ ID NO: 17) | DDNNYINTN (SEQ ID NO: 62) | DNDDYANTN (SEQ ID NO: 107) | DNNDYFNTN (SEQ ID NO: 152) | DSDDYVNTN (SEQ ID NO: 197) | DSNDYINTN (SEQ ID NO: 242) | DSNIYANTN (SEQ ID NO: 287) |

-continued

| | | | | | | |
|---|---|---|---|---|---|---|
| DDDNYVNPN (SEQ ID NO: 18) | DDNNYINPN (SEQ ID NO: 63) | DNDDYANPN (SEQ ID NO: 108) | DNNDYFNPN (SEQ ID NO: 153) | DSDDYVNPN (SEQ ID NO: 198) | DSNDYINPN (SEQ ID NO: 243) | and |
| DDDNYFNVN (SEQ ID NO: 19) | DDNNYVNVN (SEQ ID NO: 64) | DNDNYINVN (SEQ ID NO: 109) | DNNDYANVN (SEQ ID NO: 154) | DSDDYFNVN (SEQ ID NO: 199) | DSNDYVNVN (SEQ ID NO: 244) | DSNIYANPN (SEQ ID NO: 288). |
| DDDNYFNTN (SEQ ID NO: 20) | DDNNYVNTN (SEQ ID NO: 65) | DNDNYINTN (SEQ ID NO: 110) | DNNDYANTN (SEQ ID NO: 155) | DSDDYFNTN (SEQ ID NO: 200) | DSNDYVNTN (SEQ ID NO: 245) | |
| DDDNYFNPN (SEQ ID NO: 21) | DDNNYVNPN (SEQ ID NO: 66) | DNDNYINPN (SEQ ID NO: 111) | DNNDYANPN (SEQ ID NO: 156) | DSDDYFNPN (SEQ ID NO: 201) | DSNDYVNPN (SEQ ID NO: 246) | |
| DDDNYANVN (SEQ ID NO: 22) | DDNNYFNVN (SEQ ID NO: 67) | DNDNYVNVN (SEQ ID NO: 112) | DNNNYINVN (SEQ ID NO: 157) | DSDDYANVN (SEQ ID NO: 202) | DSNDYFNVN (SEQ ID NO: 247) | |
| DDDNYANTN (SEQ ID NO: 23) | DDNNYFNTN (SEQ ID NO: 68) | DNDNYVNTN (SEQ ID NO: 113) | DNNNYINTN (SEQ ID NO: 158) | DSDDYANTN (SEQ ID NO: 203) | DSNDYFNTN (SEQ ID NO: 248) | |
| DDDNYANPN (SEQ ID NO: 24) | DDNNYFNPN (SEQ ID NO: 69) | DNDNYVNPN (SEQ ID NO: 114) | DNNNYINPN (SEQ ID NO: 159) | DSDDYANPN (SEQ ID NO: 204) | DSNDYFNPN (SEQ ID NO: 249) | |
| DDDHYINVN (SEQ ID NO: 25) | DDNNYANVN (SEQ ID NO: 70) | DNDNYFNVN (SEQ ID NO: 115) | DNNNYVNVN (SEQ ID NO: 160) | DSDNYINVN (SEQ ID NO: 205) | DSNDYANVN (SEQ ID NO: 250) | |
| DDDHYINTN (SEQ ID NO: 26) | DDNNYANTN (SEQ ID NO: 71) | DNDNYFNTN (SEQ ID NO: 116) | DNNNYVNTN (SEQ ID NO: 161) | DSDNYINTN (SEQ ID NO: 206) | DSNDYANTN (SEQ ID NO: 251) | |
| DDDHYINPN (SEQ ID NO: 27) | DDNNYANPN (SEQ ID NO: 72) | DNDNYFNPN (SEQ ID NO: 117) | DNNNYVNPN (SEQ ID NO: 162) | DSDNYINPN (SEQ ID NO: 207) | DSNDYANPN (SEQ ID NO: 252) | |
| DDDHYVNVN (SEQ ID NO: 28) | DDNHYINVN (SEQ ID NO: 73) | DNDNYANVN (SEQ ID NO: 118) | DNNNYFNVN (SEQ ID NO: 163) | DSDNYVNVN (SEQ ID NO: 208) | DSNNYINVN (SEQ ID NO: 253) | |
| DDDHYVNTN (SEQ ID NO: 29) | DDNHYINTN (SEQ ID NO: 74) | DNDNYANTN (SEQ ID NO: 119) | DNNNYFNTN (SEQ ID NO: 164) | DSDNYVNTN (SEQ ID NO: 209) | DSNNYINTN (SEQ ID NO: 254) | |
| DDDHYVNPN (SEQ ID NO: 30) | DDNHYINPN (SEQ ID NO: 75) | DNDNYANPN (SEQ ID NO: 120) | DNNNYFNPN (SEQ ID NO: 165) | DSDNYVNPN (SEQ ID NO: 210) | DSNNYINPN (SEQ ID NO: 255) | |
| DDDHYFNVN (SEQ ID NO: 31) | DDNHYVNVN (SEQ ID NO: 76) | DNDHYINVN (SEQ ID NO: 121) | DNNNYANVN (SEQ ID NO: 166) | DSDNYFNVN (SEQ ID NO: 211) | DSNNYVNVN (SEQ ID NO: 256) | |
| DDDHYFNTN (SEQ ID NO: 32) | DDNHYVNTN (SEQ ID NO: 77) | DNDHYINTN (SEQ ID NO: 122) | DNNNYANTN (SEQ ID NO: 167) | DSDNYFNTN (SEQ ID NO: 212) | DSNNYVNTN (SEQ ID NO: 257) | |
| DDDHYFNPN (SEQ ID NO: 33) | DDNHYVNPN (SEQ ID NO: 78) | DNDHYINPN (SEQ ID NO: 123) | DNNNYANPN (SEQ ID NO: 168) | DSDNYFNPN (SEQ ID NO: 213) | DSNNYVNPN (SEQ ID NO: 258) | |
| DDDHYANVN (SEQ ID NO: 34) | DDNHYFNVN (SEQ ID NO: 79) | DNDHYVNVN (SEQ ID NO: 124) | DNNHYINVN (SEQ ID NO: 169) | DSDNYANVN (SEQ ID NO: 214) | DSNNYFNVN (SEQ ID NO: 259) | |
| DDDHYANTN (SEQ ID NO: 35) | DDNHYFNTN (SEQ ID NO: 80) | DNDHYVNTN (SEQ ID NO: 125) | DNNHYINTN (SEQ ID NO: 170) | DSDNYANTN (SEQ ID NO: 215) | DSNNYFNTN (SEQ ID NO: 260) | |
| DDDHYANPN (SEQ ID NO: 36) | DDNHYFNPN (SEQ ID NO: 81) | DNDHYVNPN (SEQ ID NO: 126) | DNNHYINPN (SEQ ID NO: 171) | DSDNYANPN (SEQ ID NO: 216) | DSNNYFNPN (SEQ ID NO: 261) | |
| DDDIYINVN (SEQ ID NO: 37) | DDNHYANVN (SEQ ID NO: 82) | DNDHYFNVN (SEQ ID NO: 127) | DNNHYVNVN (SEQ ID NO: 172) | DSDHYINVN (SEQ ID NO: 217) | DSNNYANVN (SEQ ID NO: 262) | |

| | | | | | |
|---|---|---|---|---|---|
| DDDIYINTN (SEQ ID NO: 38) | DDNHYANTN (SEQ ID NO: 83) | DNDHYFNTN (SEQ ID NO: 128) | DNNHYVNTN (SEQ ID NO: 173) | DSDHYINTN (SEQ ID NO: 218) | DSNNYANTN (SEQ ID NO: 263) |
| DDDIYINPN (SEQ ID NO: 39) | DDNHYANPN (SEQ ID NO: 84) | DNDHYFNPN (SEQ ID NO: 129) | DNNHYVNPN (SEQ ID NO: 174) | DSDHYINPN (SEQ ID NO: 219) | DSNNYANPN (SEQ ID NO: 264) |
| DDDIYVNVN (SEQ ID NO: 40) | DDNIYINVN (SEQ ID NO: 85) | DNDHYANVN (SEQ ID NO: 130) | DNNHYFNVN (SEQ ID NO: 175) | DSDHYVNVN (SEQ ID NO: 220) | DSNHYINVN (SEQ ID NO: 265) |
| DDDIYVNTN (SEQ ID NO: 41) | DDNIYINTN (SEQ ID NO: 86) | DNDHYANTN (SEQ ID NO: 131) | DNNHYFNTN (SEQ ID NO: 176) | DSDHYVNTN (SEQ ID NO: 221) | DSNHYINTN (SEQ ID NO: 266) |
| DDDIYVNPN (SEQ ID NO: 42) | DDNIYINPN (SEQ ID NO: 87) | DNDHYANPN (SEQ ID NO: 132) | DNNHYFNPN (SEQ ID NO: 177) | DSDHYVNPN (SEQ ID NO: 222) | DSNHYINPN (SEQ ID NO: 267) |
| DDDIYFNVN (SEQ ID NO: 43) | DDNIYVNVN (SEQ ID NO: 88) | DNDIYINVN (SEQ ID NO: 133) | DNNHYANVN (SEQ ID NO: 178) | DSDHYFNVN (SEQ ID NO: 223) | DSNHYVNVN (SEQ ID NO: 268) |
| DDDIYFNTN (SEQ ID NO: 44) | DDNIYVNTN (SEQ ID NO: 89) | DNDIYINTN (SEQ ID NO: 134) | DNNHYANTN (SEQ ID NO: 179) | DSDHYFNTN (SEQ ID NO: 224) | DSNHYVNTN (SEQ ID NO: 269) |
| DDDIYFNPN (SEQ ID NO: 45) | DDNIYVNPN (SEQ ID NO: 90) | DNDIYINPN (SEQ ID NO: 135) | DNNHYANPN (SEQ ID NO: 180) | DSDHYFNPN (SEQ ID NO: 225) | DSNHYVNPN (SEQ ID NO: 270) |

In one embodiment the peptide comprises DSDNYFNFN, DSDIYFNPN, or DSDNYFNPN.
In one embodiment the lanthanide metal is terbium.

In one embodiment the peptide comprises DSDNYFNFN (SEQ ID NO: 317), DSDIYFNPN (SEQ ID NO: 237), or DSDNYFNPN (SEQ ID NO: 213).

Certain Definitions

The term "complex" refers to molecules or ensembles that consist of a central atom or ion, which is usually metallic, and a surrounding array of bound molecules, ions or moieties of a molecule. The surrounding array of bound molecules, ions or moieties of a molecule are usually electron donors attracted to the central atom or ion. The surrounding array of bound molecules, ions or moieties of a molecule are usually neutral or negatively charged.

The term "nucleic acid" refers to deoxyribonucleotides or ribonucleotides and polymers thereof in either single- or double-stranded form, composed of monomers (nucleotides) containing a sugar, phosphate and a base which is either a purine or pyrimidine. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al. (1991) Nucl. Acids Res., 19:508; Ohtsuka et al. (1985) JBC, 260:2605; Rossolini et al. (1994) Mol. Cell. Probes, 8:91. A "nucleic acid fragment" is a fraction of a given nucleic acid molecule. Deoxyribonucleic acid (DNA) in the majority of organisms is the genetic material while ribonucleic acid (RNA) is involved in the transfer of information contained within DNA into proteins. The term "nucleotide sequence" refers to a polymer of DNA or RNA that can be single- or double-stranded, optionally containing synthetic, non-natural or altered nucleotide bases capable of incorporation into DNA or RNA polymers. The terms "nucleic acid," "nucleic acid molecule," "nucleic acid fragment," "nucleic acid sequence or segment," or "polynucleotide" may also be used interchangeably with gene, cDNA, DNA and RNA encoded by a gene.

By "portion" or "fragment," as it relates to a nucleic acid molecule, sequence or segment of the invention, when it is linked to other sequences for expression, is meant a sequence having at least 80 nucleotides, more preferably at least 150 nucleotides, and still more preferably at least 400 nucleotides. If not employed for expressing, a "portion" or "fragment" means at least 9, preferably 12, more preferably 15, even more preferably at least 20, consecutive nucleotides, e.g., probes and primers (oligonucleotides), corresponding to the nucleotide sequence of the nucleic acid molecules of the invention.

The term "amino acid," comprises the residues of the natural amino acids (e.g. Ala, Arg, Asn, Asp, Cys, Glu, Gln, Gly, His, Hyl, Hyp, Ile, Leu, Lys, Met, Phe, Pro, Ser, Thr, Trp, Tyr, and Val) in D or L form, as well as unnatural amino acids (e.g. phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine, ornithine, citruline, α-methyl-alanine, para-benzoylphenyl-alanine, phenylglycine, propargylglycine, sarcosine, and tert-butylglycine). The term also comprises natural and unnatural amino acids bearing a conventional amino protecting group (e.g. acetyl or benzyloxycarbonyl), as well as natural and unnatural amino acids protected at the carboxy terminus (e.g. as a ($C_1$-$C_6$) alkyl, phenyl or benzyl ester or amide; or as an α-methylbenzyl amide). Other suitable amino and carboxy protecting groups are known to those skilled in the art (See for example, T. W. Greene, *Protecting Groups In Organic Synthesis*; Wiley: New York, 1981, and references cited therein).

The terms "protein," "peptide" and "polypeptide" are used interchangeably herein. Polypeptide sequences specifically recited herein are written with the amino terminus on the left and the carboxy terminus on the right.

The invention encompasses isolated or substantially purified nucleic acid or protein compositions. In the context of the present invention, an "isolated" or "purified" DNA molecule or an "isolated" or "purified" polypeptide is a DNA molecule or polypeptide that exists apart from its native environment and is therefore not a product of nature. An isolated DNA molecule or polypeptide may exist in a purified form or may exist in a non-native environment such as, for example, a transgenic host cell. For example, an "isolated" or "purified" nucleic acid molecule or protein, or biologically active portion thereof, is substantially free of other cellular material, or culture medium when produced by recombinant techniques, or substantially free of chemical precursors or other chemicals when chemically synthesized. In one embodiment, an "isolated" nucleic acid is free of sequences that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. A protein that is substantially free of cellular material includes preparations of protein or polypeptide having less than about 30%, 20%, 10%, 5%, (by dry weight) of contaminating protein. When the protein of the invention, or biologically active portion thereof, is recombinantly produced, preferably culture medium represents less than about 30%, 20%, 10%, or 5% (by dry weight) of chemical precursors or non-protein-of-interest chemicals. Fragments and variants of the disclosed nucleotide sequences and proteins or partial-length proteins encoded thereby are also encompassed by the present invention. By "fragment" or "portion" is meant a full length or less than full length of the nucleotide sequence encoding, or the amino acid sequence of, a polypeptide or protein.

"Naturally occurring" is used to describe an object that can be found in nature as distinct from being artificially produced. For example, a protein or nucleotide sequence present in an organism (including a virus), which can be isolated from a source in nature and which has not been intentionally modified by man in the laboratory, is naturally occurring.

"Wild-type" refers to the normal gene, or organism found in nature without any known mutation.

A "variant" of a molecule is a sequence that is substantially similar to the sequence of the native molecule. For nucleotide sequences, variants include those sequences that, because of the degeneracy of the genetic code, encode the identical amino acid sequence of the native protein. Naturally occurring allelic variants such as these can be identified with the use of well-known molecular biology techniques, as, for example, with polymerase chain reaction (PCR) and hybridization techniques. Variant nucleotide sequences also include synthetically derived nucleotide sequences, such as those generated, for example, by using site-directed mutagenesis that encode the native protein, as well as those that encode a polypeptide having amino acid substitutions. Generally, nucleotide sequence variants of the invention will have at least 40, 50, 60, to 70%, e.g., preferably 71%, 72%, 73%, 74%, 75%, 76%, 77%, 78%, to 79%, generally at least 80%, e.g., 81%-84%, at least 85%, e.g., 86%, 87%, 88%, 89%, 90%, 91%, 92%, 93%, 94%, 95%, 96%, 97%, to 98%, sequence identity to the native (endogenous) nucleotide sequence.

"Conservatively modified variations" of a particular nucleic acid sequence refers to those nucleic acid sequences that encode identical or essentially identical amino acid sequences, or where the nucleic acid sequence does not encode an amino acid sequence, to essentially identical sequences. Because of the degeneracy of the genetic code, a large number of functionally identical nucleic acids encode any given polypeptide. For instance the codons CGT, CGC, CGA, CGG, AGA, and AGG all encode the amino acid arginine. Thus, at every position where an arginine is specified by a codon, the codon can be altered to any of the corresponding codons described without altering the encoded protein. Such nucleic acid variations are "silent variations" which are one species of "conservatively modified variations." Every nucleic acid sequence described herein which encodes a polypeptide also describes every possible silent variation, except where otherwise noted. One of skill will recognize that each codon in a nucleic acid (except ATG, which is ordinarily the only codon for methionine) can be modified to yield a functionally identical molecule by standard techniques. Accordingly, each "silent variation" of a nucleic acid which encodes a polypeptide is implicit in each described sequence.

"Recombinant DNA molecule" is a combination of DNA sequences that are joined together using recombinant DNA technology and procedures used to join together DNA sequences as described, for example, in Sambrook and Russell, Molecular Cloning: A Laboratory Manual, Cold Spring Harbor, N.Y.: Cold Spring Harbor Laboratory Press ($3^{rd}$ edition, 2001).

The terms "heterologous DNA sequence," "exogenous DNA segment" or "heterologous nucleic acid," each refer to a sequence that originates from a source foreign to the particular host cell or, if from the same source, is modified from its original form. Thus, a heterologous gene in a host cell includes a gene that is endogenous to the particular host cell but has been modified. The terms also include non-naturally occurring multiple copies of a naturally occurring DNA sequence. Thus, the terms refer to a DNA segment that is foreign or heterologous to the cell, or homologous to the cell but in a position within the host cell nucleic acid in which the element is not ordinarily found. Exogenous DNA segments are expressed to yield exogenous polypeptides.

A "homologous" DNA sequence is a DNA sequence that is naturally associated with a host cell into which it is introduced.

The term "gene" is used broadly to refer to any segment of nucleic acid associated with a biological function. Genes include coding sequences and/or the regulatory sequences required for their expression. For example, gene refers to a nucleic acid fragment that expresses mRNA, functional RNA, or a specific protein, including its regulatory sequences. Genes also include nonexpressed DNA segments that, for example, form recognition sequences for other proteins. Genes can be obtained from a variety of sources, including cloning from a source of interest or synthesizing from known or predicted sequence information, and may include sequences designed to have desired parameters. In addition, a "gene" or a "recombinant gene" refers to a nucleic acid molecule comprising an open reading frame and including at least one exon and (optionally) an intron sequence. The term "intron" refers to a DNA sequence present in a given gene which is not translated into protein and is generally found between exons.

A "vector" is defined to include, inter alia, any viral vector, plasmid, cosmid, phage or binary vector in double or single stranded linear or circular form which may or may not be self-transmissible or mobilizable, and which can transform prokaryotic or eukaryotic host either by integration into the cellular genome or exist extrachromosomally (e.g., autonomous replicating plasmid with an origin of replication).

"Cloning vectors" typically contain one or a small number of restriction endonuclease recognition sites at which foreign DNA sequences can be inserted in a determinable fashion without loss of essential biological function of the vector, as well as a marker gene that is suitable for use in the identification and selection of cells transformed with the cloning vector. Marker genes typically include genes that provide tetracycline resistance, hygromycin resistance or ampicillin resistance.

"Expression cassette" as used herein means a DNA sequence capable of directing expression of a particular nucleotide sequence in an appropriate host cell, comprising a promoter operably linked to the nucleotide sequence of interest which is operably linked to termination signals. It also typically comprises sequences required for proper translation of the nucleotide sequence. The coding region usually codes for a protein of interest but may also code for a functional RNA of interest, for example antisense RNA or a nontranslated RNA, in the sense or antisense direction. The expression cassette comprising the nucleotide sequence of interest may be chimeric, meaning that at least one of its components is heterologous with respect to at least one of its other components. The expression cassette may also be one that is naturally occurring but has been obtained in a recombinant form useful for heterologous expression. The expression of the nucleotide sequence in the expression cassette may be under the control of a constitutive promoter or of an inducible promoter that initiates transcription only when the host cell is exposed to some particular external stimulus. In the case of a multicellular organism, the promoter can also be specific to a particular tissue or organ or stage of development.

Such expression cassettes will comprise the transcriptional initiation region of the invention linked to a nucleotide sequence of interest. Such an expression cassette is provided with a plurality of restriction sites for insertion of the gene of interest to be under the transcriptional regulation of the regulatory regions. The expression cassette may additionally contain selectable marker genes.

The term "RNA transcript" refers to the product resulting from RNA polymerase catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA" (mRNA) refers to the RNA that is without introns and that can be translated into protein by the cell. "cDNA" refers to a single- or a double-stranded DNA that is complementary to and derived from mRNA.

"Regulatory sequences" and "suitable regulatory sequences" each refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences include enhancers, promoters, translation leader sequences, introns, and polyadenylation signal sequences. They include natural and synthetic sequences as well as sequences that may be a combination of synthetic and natural sequences. As is noted above, the term "suitable regulatory sequences" is not limited to promoters. However, some suitable regulatory sequences useful in the present invention will include, but are not limited to constitutive promoters, tissue-specific promoters, development-specific promoters, inducible promoters and viral promoters.

"Promoter" refers to a nucleotide sequence, usually upstream (5') to its coding sequence, which controls the expression of the coding sequence by providing the recognition for RNA polymerase and other factors required for proper transcription. "Promoter" includes a minimal promoter that is a short DNA sequence comprised of a TATA-box and other sequences that serve to specify the site of transcription initiation, to which regulatory elements are added for control of expression. "Promoter" also refers to a nucleotide sequence that includes a minimal promoter plus regulatory elements that is capable of controlling the expression of a coding sequence or functional RNA. This type of promoter sequence consists of proximal and more distal upstream elements, the latter elements often referred to as enhancers. Accordingly, an "enhancer" is a DNA sequence that can stimulate promoter activity and may be an innate element of the promoter or a heterologous element inserted to enhance the level or tissue specificity of a promoter. Promoters may be derived in their entirety from a native gene, or be composed of different elements derived from different promoters found in nature, or even be comprised of synthetic DNA segments. A promoter may also contain DNA sequences that are involved in the binding of protein factors that control the effectiveness of transcription initiation in response to physiological or developmental conditions.

"Expression" refers to the transcription and/or translation in a cell of an endogenous gene, transgene, as well as the transcription and stable accumulation of sense (mRNA) or functional RNA. In the case of antisense constructs, expression may refer to the transcription of the antisense DNA only. Expression may also refer to the production of protein.

"Homology" refers to the percent identity between two polynucleotides or two polypeptide sequences. Two DNA or polypeptide sequences are "homologous" to each other when the sequences exhibit at least about 75% to 85% (including 75%, 76%, 77%, 78%, 79%, 80%, 81%, 82%, 83%, 84%, and 85%), at least about 90%, or at least about 95% to 99% (including 95%, 96%, 97%, 98%, 99%) contiguous sequence identity over a defined length of the sequences.

The following terms are used to describe the sequence relationships between two or more sequences (e.g., nucleic acids, polynucleotides or polypeptides): (a) "reference sequence," (b) "comparison window," (c) "sequence identity," (d) "percentage of sequence identity," and (e) "substantial identity."

(a) As used herein, "reference sequence" is a defined sequence used as a basis for sequence comparison. A reference sequence may be a subset or the entirety of a specified sequence; for example, as a segment of a full length cDNA, gene sequence or peptide sequence, or the complete cDNA, gene sequence or peptide sequence.

(b) As used herein, "comparison window" makes reference to a contiguous and specified segment of a sequence, wherein the sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the sequence a gap penalty is typically introduced and is subtracted from the number of matches.

Methods of alignment of sequences for comparison are well known in the art. Thus, the determination of percent identity between any two sequences can be accomplished using a mathematical algorithm. Non-limiting examples of such mathematical algorithms are the algorithm of Myers and Miller (1988) CABIOS, 4:11; the local homology algorithm of Smith et al. (1981) Adv. Appl. Math. 2:482; the homology alignment algorithm of Needleman and Wunsch, (1970) JMB, 48:443; the search-for-similarity-method of Pearson and Lipman, (1988) Proc. Natl. Acad. Sci. USA, 85:2444; the algorithm of Karlin and Altschul, (1990) Proc. Natl. Acad. Sci. USA, 87:2264, modified as in Karlin and Altschul, (1993) Proc. Natl. Acad. Sci. USA, 90:5873.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described by Higgins et al. (1988) Gene 73:237; Higgins et al. (1989) CABIOS 5:151; Corpet et al. (1988) Nucl. Acids Res. 16:10881; Huang et al. (1992) CABIOS 8:155; and Pearson et al. (1994) Meth. Mol. Biol. 24:307. The ALIGN program is based on the algorithm of Myers and Miller, supra. The BLAST programs of Altschul et al. (1990) JMB, 215:403; Nucl. Acids Res., 25:3389 (1990), are based on the algorithm of Karlin and Altschul supra.

Software for performing BLAST analyses is publicly available through the National Center for Biotechnology Information (available on the world wide web at ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached.

In addition to calculating percent sequence identity, the BLAST algorithm also performs a statistical analysis of the similarity between two sequences. One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, more preferably less than about 0.01, and most preferably less than about 0.001.

To obtain gapped alignments for comparison purposes, Gapped BLAST (in BLAST 2.0) can be utilized as described in Altschul et al. (1997) Nucleic Acids Res. 25:3389. Alternatively, PSI-BLAST (in BLAST 2.0) can be used to perform an iterated search that detects distant relationships between molecules. See Altschul et al., supra. When utilizing BLAST, Gapped BLAST, PSI-BLAST, the default parameters of the respective programs (e.g., BLASTN for nucleotide sequences, BLASTX for proteins) can be used. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix. See the world wide web at ncbi.nlm.nih.gov. Alignment may also be performed manually by visual inspection.

For purposes of the present invention, comparison of sequences for determination of percent sequence identity to another sequence may be made using the BlastN program (version 1.4.7 or later) with its default parameters or any equivalent program. By "equivalent program" is intended any sequence comparison program that, for any two sequences in question, generates an alignment having identical nucleotide or amino acid residue matches and an identical percent sequence identity when compared to the corresponding alignment generated by the preferred program.

(c) As used herein, "sequence identity" or "identity" in the context of two nucleic acid or polypeptide sequences makes reference to a specified percentage of residues in the two sequences that are the same when aligned for maximum correspondence over a specified comparison window, as measured by sequence comparison algorithms or by visual inspection. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of sequences means that a polynucleotide comprises a sequence that has at least 70%, 71%, 72%, 73%, 74%, 75%, 76%, 77%, 78%, or 79%, at least 80%, 81%, 82%, 83%, 84%, 85%, 86%, 87%, 88%, or 89%, at least 90%, 91%, 92%, 93%, or 94%, and at least 95%, 96%, 97%, 98%, or 99% sequence identity, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 70%, at least 80%, 90%, at least 95%.

(e)(ii) The term "substantial identity" in the context of a peptide indicates that a peptide comprises a sequence with at least 70%, 71%, 72%, 73%, 74%, 75%, 76%, 77%, 78%, or 79%, 80%, 81%, 82%, 83%, 84%, 85%, 86%, 87%, 88%, or 89%, at least 90%, 91%, 92%, 93%, or 94%, or 95%, 96%, 97%, 98% or 99%, sequence identity to the reference sequence over a specified comparison window. Optimal alignment is conducted using the homology alignment algorithm of Needleman and Wunsch, J. Mol. Biol. 48:443 (1970). An indication that two peptide sequences are substantially identical is that one peptide is immunologically reactive with antibodies raised against the second peptide. Thus, a peptide is substantially identical to a second peptide, for example, where the two peptides differ only by a conservative substitution.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

By "variant" polypeptide is intended a polypeptide derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein. Such variants may results form, for example, genetic polymorphism or from human manipulation. Methods for such manipulations are generally known in the art.

Thus, the polypeptides of the invention may be altered in various ways including amino acid substitutions, deletions, truncations, and insertions. Methods for such manipulations are generally known in the art. For example, amino acid sequence variants of the polypeptides can be prepared by mutations in the DNA. Methods for mutagenesis and nucleotide sequence alterations are well known in the art. See, for example, Kunkel (1985) Proc. Natl. Acad. Sci. USA 82:488; Kunkel et al. (1987) Meth. Enzymol. 154:367; U.S. Pat. No. 4,873,192; Walker and Gaastra (1983) Techniques in Mol. Biol. (MacMillan Publishing Co., and the references cited therein. Guidance as to appropriate amino acid substitutions that do not affect biological activity of the protein of interest may be found in the model of Dayhoff et al., Atlas of Protein Sequence and Structure (Natl. Biomed. Res. Found. 1978). Conservative substitutions, such as exchanging one amino acid with another having similar properties, are preferred.

Thus, the genes and nucleotide sequences of the invention include both the naturally occurring sequences as well as mutant forms. Likewise, the polypeptides of the invention encompass naturally occurring proteins as well as variations and modified forms thereof. Such variants will continue to possess the desired activity. In certain embodiments, the deletions, insertions, and substitutions of the polypeptide sequence encompassed herein may not produce radical changes in the characteristics of the polypeptide. However, when it is difficult to predict the exact effect of the substitution, deletion, or insertion in advance of doing so, one skilled in the art will appreciate that the effect will be evaluated by routine screening assays.

Individual substitutions deletions or additions that alter, add or delete a single amino acid or a small percentage of amino acids (typically less than 5%, more typically less than 1%) in an encoded sequence are "conservatively modified variations," where the alterations result in the substitution of an amino acid with a chemically similar amino acid. Conservative substitution tables providing functionally similar amino acids are well known in the art. The following five groups each contain amino acids that are conservative substitutions for one another: Aliphatic: Glycine (G), Alanine (A), Valine (V), Leucine (L), Isoleucine (I); Aromatic: Phenylalanine (F), Tyrosine (Y), Tryptophan (W); Sulfur-containing: Methionine (M), Cysteine (C); Basic: Arginine (R), Lysine (K), Histidine (H); Acidic: Aspartic acid (D), Glutamic acid (E), Asparagine (N), Glutamine (Q). In addition, individual substitutions, deletions or additions which alter, add or delete a single amino acid or a small percentage of amino acids in an encoded sequence are also "conservatively modified variations."

"Operably-linked" refers to the association two chemical moieties so that the function of one is affected by the other, e.g., an arrangement of elements wherein the components so described are configured so as to perform their usual function. In certain embodiments, amino acid sequences are operably linked via a peptide bond.

The invention will now be illustrated by the following non-limiting Example.

Example 1

In order to develop an optimal peptide substrate for FLT3 kinase, a strategy called "Kinase Assay Linked with Phosphoproteomics (KALIP)" (www.ncbi.nlm.nih.gov/pubmed/26584932) was adapted to perform high throughput identification of peptide sequences that are phosphorylated by FLT3 and its variants. The identified substrate sequences were then used as input for the KINATEST-ID pipeline to determine FLT3's preferred peptide substrate motif. The motif was used to design potential peptide substrates for FLT3. A selection of these were tested to identify key sequence features that conferred phosphorylation by FLT3 and/or the two variants tested here.

The objective is to identify FLT3-specific peptide substrates in a high throughput manner, and to use that information to design novel FLT3 substrate peptides. The sequences that are efficiently phosphorylated can then be used in assays to determine if FLT3 kinase is active in a system, which, in turn, can be used to identify new FLT3 kinase inhibitors.

KINATEST-ID Implementation and adaptation for substrate development

Figure 6:
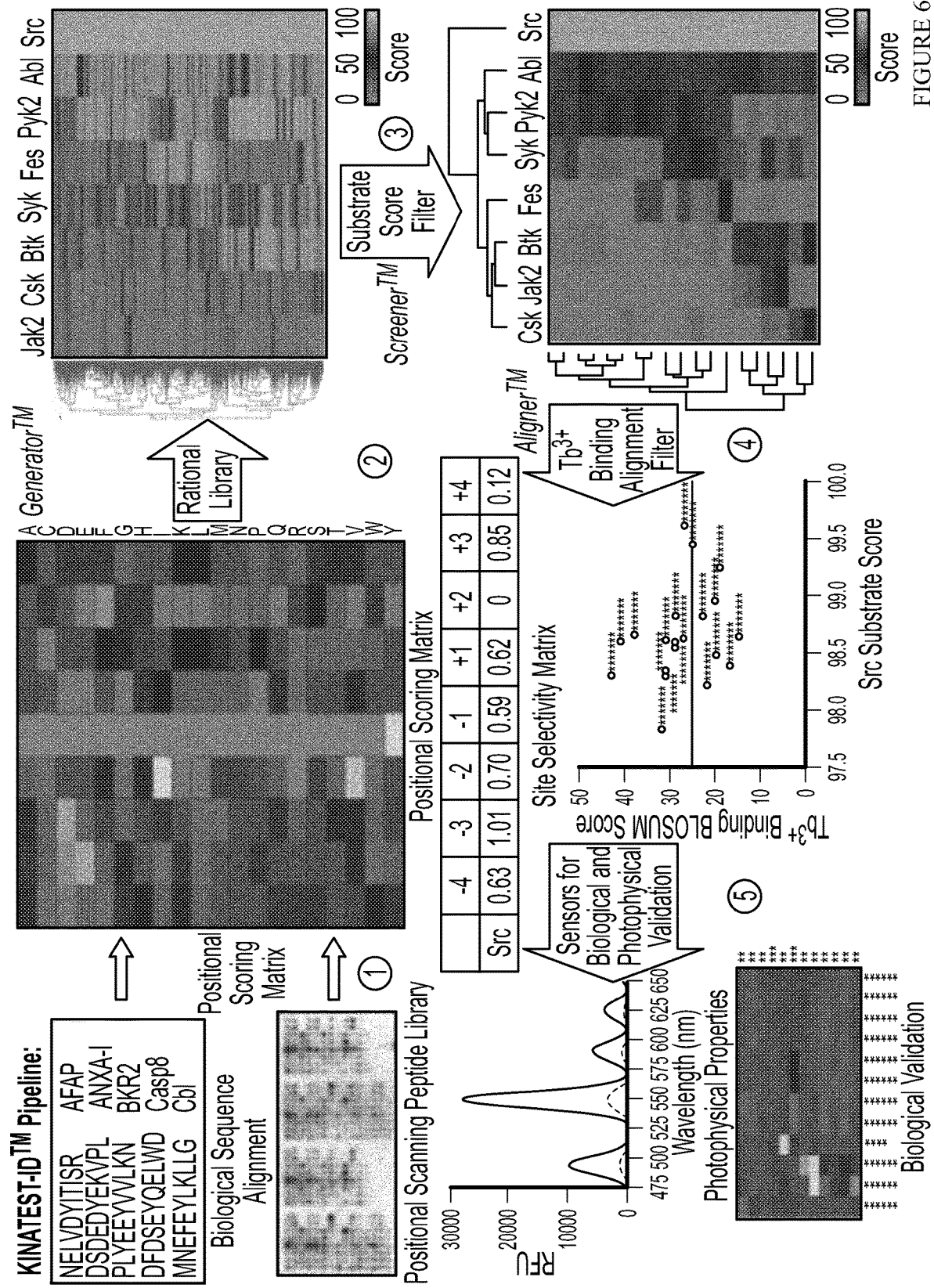
FIG. 6 illustrates the KINTEST-ID Pipeline, see Lipchik, A. M. et al. *J. Am. Chem. Soc.* 137, 2484-2494 (2015).

The KINATEST-ID Pipeline is a subset of modules that can identify potential sequences for a specific kinase or kinase family (see Lipchik, A. M. et al. *J. Am. Chem. Soc.* 137, 2484-2494 (2015)). FIG. 6 illustrates the original implementation of KINATEST-ID pipeline that consists of 5 modules: positional scoring matrix (PSM), Generator, Screener, Aligner and empirical validation of artificial substrates. The positional scoring matrix consists of the positional scanning peptide library and the positional probability matrix (PPM). The positional scanning library was provided by the Turk group; subsequently, phosphorylation was quantified based on phosphorylation intensity and normalized in order to incorporate them with the positional probability matrix (see Lipchik, A. M. et al. *J. Am. Chem. Soc.* 137, 2484-2494 (2015); and Deng, Y., et al., *J. Proteome Res.* 13, 4339-4346 (2014)).

Figure 7:
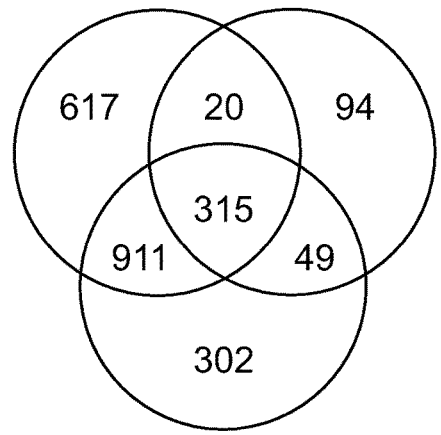
FIG. 7 illustrates the number and overlap of phosphopeptide identifications from 1) recombinant kinase assays with wild type FLT3 (FLT3-WT) or the D835Y or ITD mutants (FLT3-D835Y and FLT3-ITD), 2) phosphopeptide enrichment, 3) LC-MS/MS analysis and 4) proteomic database search against the human UniProt/Swissprot database using the ProteinPilot 5.0 search algorithm.

The PPM consists of two data sets: "substrate" and "substrate background" data sets. In the original KINATEST-ID design, the substrate data set contained validated endogenous peptide substrates motifs from the kinase of interest found in proteomic databases (Phosphositeplus.org, Human Protein Reference Database, etc.). In this implementation (FIG. 8), validated substrates were empirically identified by performing a kinase reaction with recombinant FLT3 or its mutant variants on a phosphate-stripped "library" of peptides generated by trypsin digestion of a whole protein extract from the KG-1 AML cell line. Briefly, the protein extract was treated with trypsin to digest proteins into peptides and desalted using a C18 cartridge. The resulting peptide mixture was treated with alkaline phosphatase to remove any existing phosphorylation, followed by treating overnight with recombinant kinase (FLT3-WT, FLT3 D835Y, or FLT3-ITD) or for 2 h (FLT3-WT) to re-phosphorylate any FLT3 and/or variant substrate sequences in the mixture. Reactions were performed in triplicate. Phosphopeptides were enriched using the poly-MAC enrichment kit (Tymora Analytical) and analyzed with LC-MS/MS on an Orbitrap Fusion (Thermo). Data were searched against the human UniProt/Swissprot proteome database using Protein Pilot 5.0 (SCIEX). Number and overlap of phosphopeptides identified from each kinase variant are summarized in FIG. 7.

Figure 8:
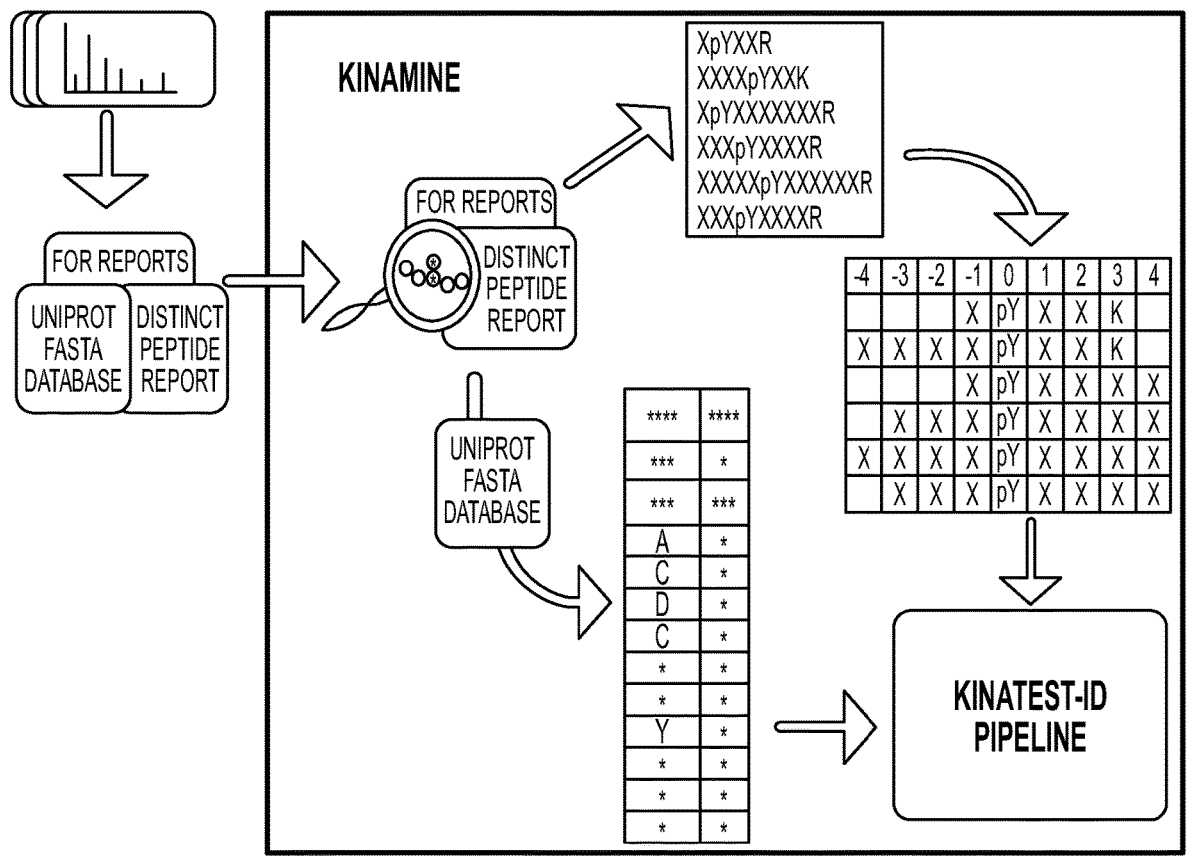
FIG. 8 illustrates protein ID search results generated as described in FIG. 7 were formatted for input into KINATEST-ID's positional scoring matrix calculator. Using the search results, the KINAMINE tool formatted the peptide sequences to the tyrosine residue that was shown to be phosphorylated for incorporation to the positional scoring matrix module of KINATEST-ID. The KINAMINE tool then used the Uniprot protein accession number from the FDR report to extract the amino acid composition of the protein that contained the sequence of interest. The protein amino acid composition was also imported into the positional scoring matrix.
Figure 17:
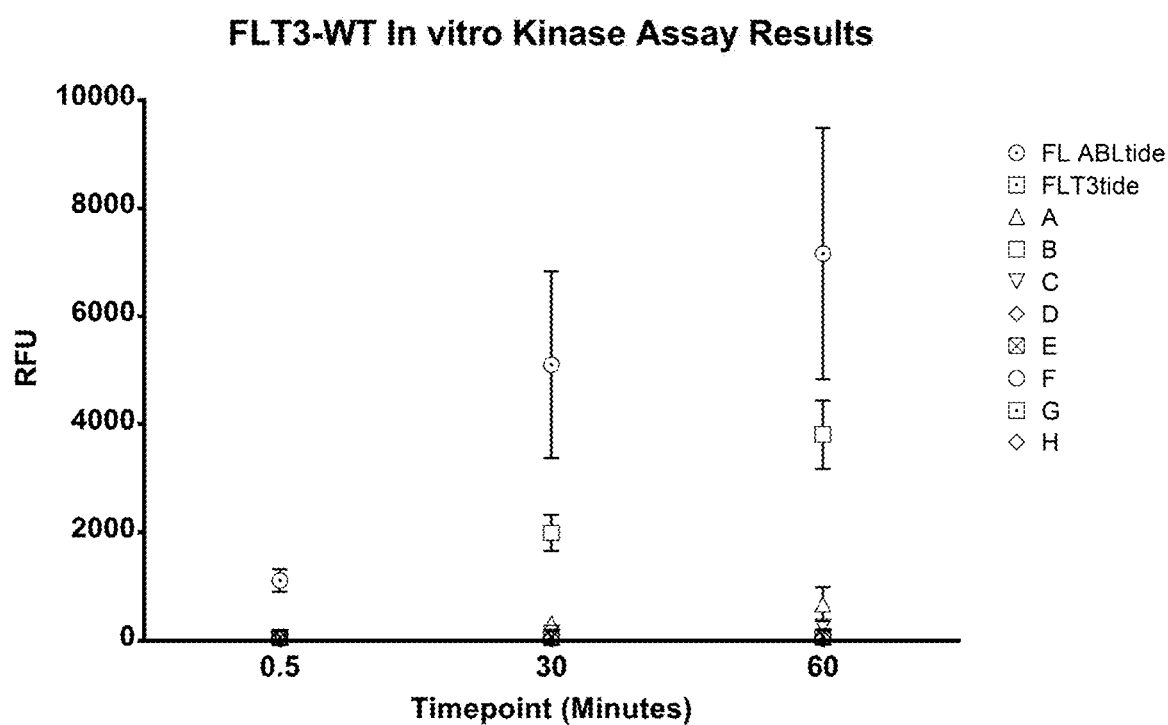
FIG. 17 illustrates FLT3 wild type's (WT) in vitro kinase assay results for the candidate sequences (A, B, C, D, E, F, G and H) from FIG. 15. "FL-Abltide" contains a sequence (EAIYAAPFAK (SEQ ID NO: 313)) that is a previously known FLT3 peptide substrate and has been used as a reference substrate to monitor kinase activity. "Flt3tide" (FTDRLQQYISTR (SEQ ID NO: 314)) is the previously reported Flt3 substrate from Böhmer, F.-D. & Uecker, A. Br. J. Haematol. 144, 127-30 (2009). Sequence A showed a similar level of phosphorylation compared to Abltide over a 60-minute incubation. The remaining sequences did not get phosphorylated by FLT3-WT. These results show that sequences phosphorylated by FLT3-WT optimally contain the DSDXYFNXN motif (SEQ ID NO: 315). This result also showed that a single mutation to certain amino acids at those respective residues could abolish phosphorylation. Additionally, FLT3-WT could phosphorylate sequences containing either an asparagine (N) or an isoleucine (I) residue at position −1, while the preferred residues at position 3 were phenylalanine (F) or proline (P).
Figure 18:
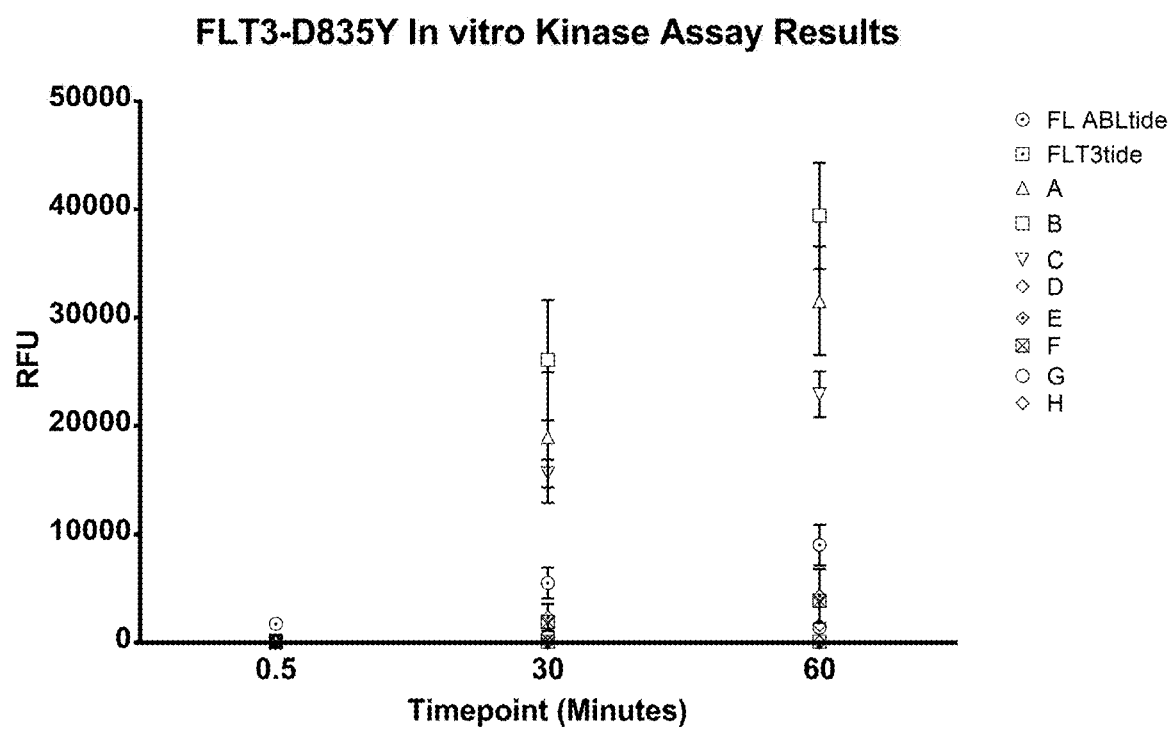
FIG. 18 illustrates FLT3-D835Y (D835Y) mutant's in vitro kinase assay results for the candidate sequences (A, B, C, D, E, F, G and H) from FIG. 15. "FL-Abltide" contains a sequence (EAIYAAPFAK (SEQ ID NO: 313)) that is a previously known FLT3 peptide substrate and has been used a reference substrate to monitor kinase activity. "Flt3tide" (FTDRLQQYISTR (SEQ ID NO: 314)) is the previously reported Flt3 substrate from Böhmer, F.-D. & Uecker, A. Br. J. Haematol. 144, 127-30 (2009). Candidate sequences A, B, C displayed higher levels of phosphorylation by FLT3-D835Y compared to FL-Abltide. Sequences E, F and G were also phosphorylated by FLT3-D835Y but at lower levels than FL-Abltide while sequence H showed no phosphorylation. These results indicate that the FLT3-D835Y mutant was shown to phosphorylate sequences that contained the DXDXYXNXN motif (SEQ ID NO: 316). The preferred residue at position −3 was shown to be either serine (S) or asparagine (N), while a sequence that contained a histidine (H) at that position showed no phosphorylation. Asparagine (N) and isoleucine (I) were shown to be the preferred residues at position-1. However, sequences that contained aspartic acid (D) at that position showed low levels of phosphorylation, while sequences that contained glutamine (Q) at that position showed no phosphorylation. Phenylalanine (F) was the preferred residue at position 1, while alanine (A) and cysteine (C) at position 1 showed low levels of phosphorylation. Sequences that contained phenylalanine (F), proline (P) and threonine (T) residues at position 3 were shown to be phosphorylated by FLT3-D835Y.
Figure 19:
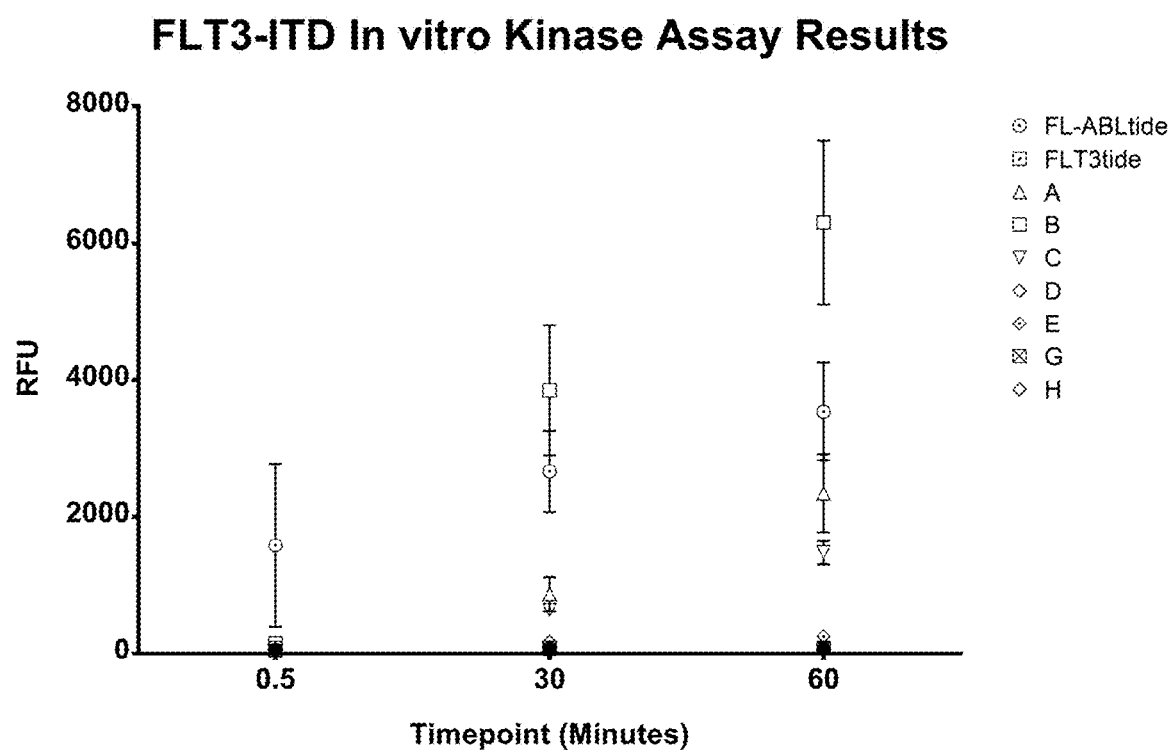
FIG. 19 illustrates FLT3-ITD (ITD) mutant's in vitro kinase assay results for the candidate sequences (A, B, C, D, E, F, G and H) from table 15. "FL-Abltide" contains a sequence (EAIYAAPFAK (SEQ ID NO: 313)) that is a previously known FLT3 peptide substrate and has been used a reference substrate to monitor kinase activity. "Flt3tide" (FTDRLQQYISTR (SEQ ID NO: 314)) is the previously reported Flt3 substrate from Böhmer, F.-D. & Uecker, A. Br. J. Haematol. 144, 127-30 (2009). Sequence A showed higher levels of phosphorylation than Abltide. Sequences B and C displayed lower levels of phosphorylation than FL-Abltide over a 60-minute incubation. Sequences E-H did not show phosphorylation by FLT3-ITD over a 60-minute incubation. According to these results, the consensus motif for the FLT3-ITD mutant is similar to FLT3-WT; however, sequence C showed that the combination of asparagine (N) at position-1 and proline (P) at position 3 abolished phosphorylation by FLT3-WT but not by FLT3-ITD.

In order to use the peptide identification results with the KINATEST-ID platform, the substrate motifs of interest were formatted using the KinaMINE, which centered the sequences to the tyrosine residue of interest so they would be compatible as input for the first module of the KINAT-EST-ID (FIG. 8). Since these sequences were generated using trypsin, which cleaves at the carboxyl side of an arginine or lysine amino acid residue, many sequences were not in the desired format to complete the motif of interest (XXXXYXXXX; -4, -3 ... 0 ... 3, 4), but nonetheless were aligned by the central tyrosine. A "substrate background" data set of "negative" sequences inferred to not be substrates was generated, containing the tyrosine centered peptide motifs that were present in the parent proteins for the phosphopeptides identified in the enrichment experiment (extracted from the sequences for those proteins in the UniProt database), but not observed as phosphopeptides themselves—suggesting they were present in the kinase reaction but not phosphorylated by the kinase of interest. Once the "substrate" and "substrate background" datasets were added to the Positional Scoring Matrix module, the standard deviation ($\sigma$) values for representation of a given amino acid at each position in the 9-amino acid, tyrosine-centered sequence were calculated and are shown in the tables below. An amino acid was assigned as significantly represented in the motif when it was observed at a frequency that was two standard deviations ($2\sigma$) above the mean for all amino acids observed at that position. The amino acids that were $2\sigma$ above the mean were determined favorable and were incorporated into the generator module that is illustrated in table 13. The Generator module then created all the permutations from the significant amino acids at their respective positions. Positions that did not have defined favorable amino acid residues were filled with residues that contained the largest possible $\sigma$ value. Using this approach, the generator module returned 288 possible sequence permutations that were then incorporated into the screener module. The Screener module screened potential artificial substrate sequences against the positional scoring matrices for a panel of kinases, to pre-filter based on suggested specificity.

Table 15 describes the sequences chosen for synthesis and testing as FLT3 and FLT3 mutant variant substrates. Table 16 illustrates the Screener module's results that suggest likelihood of specificity for FLT3. A set of sequences that scored well for FLT3, but were suggested by the KINATEST-ID panel as likely to be relatively poor substrates of other kinases (sequence A, C and H) was synthesized. A set of sequences was also synthesized that scored well for FLT3, but also for several other kinases in the panel (sequence B, D, E, F and G) FLT3 to have a higher likelihood of obtaining an efficient, even if potentially not as FLT3-specific, substrate. A summary of results from FLT3 kinase activity testing of these sequences are provided in columns 7-9 of Table 15.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A peptide comprising an amino acid sequence of formula I:

$$D-R^0-R^1-R^2-R^3-R^4-R^5-R^6-R^7 \quad (I)$$

wherein:
- $R^0$ is selected from the group consisting of: D, S and N;
- $R^1$ is selected from the group consisting of: D and N;
- $R^2$ is selected from the group consisting of: D, H, I and N;
- $R^3$ is Y;
- $R^4$ is selected from the group consisting of: I, F, A, and V;
- $R^5$ is N;
- $R^6$ is selected from the group consisting of: P, T, and V; and
- $R^7$ is N;

or a salt thereof.

2. A peptide comprising an amino acid sequence of formula I:

$$D-R^0-R^1-R^2-R^3-R^4-R^5-R^6-R^7 \quad (I)$$

wherein:
- $R^0$ is D;
- $R^1$ is selected from the group consisting of: D, S, and N;
- $R^2$ is selected from the group consisting of: D, H, and N;
- $R^3$ is Y;
- $R^4$ is selected from the group consisting of: Q, H, and V;
- $R^5$ is N
- $R^6$ is P; and
- $R^7$ is N;

or a salt thereof (SEQ ID NO: 318).

3. The peptide of claim 2 consisting of an amino acid sequence selected from the group consisting of:

DDDDYQNPN, (SEQ ID NO: 289)

DDDDYHNPN, (SEQ ID NO: 290)

DDDYVNPN, (SEQ ID NO: 291)

DDDHYQNPN, (SEQ ID NO: 292)

DDDHYHNPN, (SEQ ID NO: 293)

DDDHYVNPN, (SEQ ID NO: 30)

DDDNYQNPN, (SEQ ID NO: 294)

DDDNYHNPN, (SEQ ID NO: 295)

DDDNYVNPN, (SEQ ID NO: 18)

DDSDYQNPN, (SEQ ID NO: 296)

DDSDYHNPN, (SEQ ID NO: 297)

DDSHYQNPN, (SEQ ID NO: 298)

DDSHYHNPN, (SEQ ID NO: 299)

DDSHVVNPN, (SEQ ID NO: 300)

DDSNYQNPN, (SEQ ID NO: 301)

DDSNYHNPN, (SEQ ID NO: 302)

DDSNYVNPN, (SEQ ID NO: 303)

DDNDYQNPN, (SEQ ID NO: 304)

DDNDYHNPN, (SEQ ID NO: 305)

-continued

| | |
|---|---|
| DDNDYVNPN, | (SEQ ID NO: 54) |
| DDNHYQNPN, | (SEQ ID NO: 306) |
| DDNHYHNPN, | (SEQ ID NO: 307) |
| DDNHYVNPN, | (SEQ ID NO: 78) |
| DDNNYQNPN, | (SEQ ID NO: 308) |
| DDNNYHNPN, and | (SEQ ID NO: 309) |
| DDNNYVNPN. | (SEQ ID NO: 66) |

4. The peptide of claim 1, wherein:
$R^0$ is selected from the group consisting of: S and N;
$R^1$ is D;
$R^2$ is selected from the group consisting of: I and N;
$R^3$ is Y;
$R^4$ is F;
$R^5$ is N;
$R^6$ is selected from the group consisting of: P and T; and
$R^7$ is N;
or a salt thereof.

5. The peptide of claim 1, wherein:
$R^0$ is S;
$R^1$ is D;
$R^2$ is selected from the group consisting of: I and N;
$R^3$ is Y;
$R^4$ is F;
$R^5$ is N;
$R^6$ is P; and
$R^7$ is N;
or a salt thereof.

6. The peptide of claim 1, wherein:
$R^2$ is N; and
$R^6$ is P.

7. The peptide of claim 1, wherein when $R^2$ is N, $R^6$ is not P; or wherein when $R^6$ is P, $R^2$ is not N.

8. The peptide of claim 1, wherein $R^2$ is not D.

9. The peptide of claim 1, wherein $R^4$ is not A.

10. A peptide consisting of an amino acid sequence selected from the group consisting of:

| | | | | | | |
|---|---|---|---|---|---|---|
| DDDDYINVN (SEQ ID NO: 1) | DDDIYANVN (SEQ ID NO: 46) | DDNIYFNVN (SEQ ID NO: 91) | DNDIYVNVN (SEQ ID NO: 136) | DNNIYINVN (SEQ ID NO: 181) | DSDHYANVN (SEQ ID NO: 226) | DSNHYFNVN (SEQ ID NO: 271) |
| DDDDYINTN (SEQ ID NO: 2) | DDDIYANTN (SEQ ID NO: 47) | DDNIYFNTN (SEQ ID NO: 92) | DNDIYVNTN (SEQ ID NO: 137) | DNNIYINTN (SEQ ID NO: 182) | DSDHYANTN (SEQ ID NO: 227) | DSNHYFNTN (SEQ ID NO: 272) |
| DDDDYINPN (SEQ ID NO: 3) | DDDIYANPN (SEQ ID NO: 48) | DDNIYFNPN (SEQ ID NO: 93) | DNDIYVNPN (SEQ ID NO: 138) | DNNIYINPN (SEQ ID NO: 183) | DSDHYANPN (SEQ ID NO: 228) | DSNHYFNPN (SEQ ID NO: 273) |
| DDDDYVNVN (SEQ ID NO: 4) | DDNDYINVN (SEQ ID NO: 49) | DDNIYANVN (SEQ ID NO: 94) | DNDIYFNVN (SEQ ID NO: 139) | DNNIYVNVN (SEQ ID NO: 184) | DSDIYINVN (SEQ ID NO: 229) | DSNHYANVN (SEQ ID NO: 274) |
| DDDDYVNTN (SEQ ID NO: 5) | DDNDYINTN (SEQ ID NO: 50) | DDNIYANTN (SEQ ID NO: 95) | DNDIYFNTN (SEQ ID NO: 140) | DNNIYVNTN (SEQ ID NO: 185) | DSDIYINTN (SEQ ID NO: 230) | DSNHYANTN (SEQ ID NO: 275) |
| DDDDYVNPN (SEQ ID NO: 6) | DDNDYINPN (SEQ ID NO: 51) | DDNIYANPN (SEQ ID NO: 96) | DNDIYFNPN (SEQ ID NO: 141) | DNNIYVNPN (SEQ ID NO: 186) | DSDIYINPN (SEQ ID NO: 231) | DSNHYANPN (SEQ ID NO: 276) |
| DDDDYFNVN (SEQ ID NO: 7) | DDNDYVNVN (SEQ ID NO: 52) | DNDDYINVN (SEQ ID NO: 97) | DNDIYANVN (SEQ ID NO: 142) | DNNIYFNVN (SEQ ID NO: 187) | DSDIYVNVN (SEQ ID NO: 232) | DSNIYINVN (SEQ ID NO: 277) |
| DDDDYFNTN (SEQ ID NO: 8) | DDNDYVNTN (SEQ ID NO: 53) | DNDDYINTN (SEQ ID NO: 98) | DNDIYANTN (SEQ ID NO: 143) | DNNIYFNTN (SEQ ID NO: 188) | DSDIYVNTN (SEQ ID NO: 233) | DSNIYINTN (SEQ ID NO: 278) |
| DDDDYFNPN (SEQ ID NO: 9) | DDNDYVNPN (SEQ ID NO: 54) | DNDDYINPN (SEQ ID NO: 99) | DNDIYANPN (SEQ ID NO: 144) | DNNIYFNPN (SEQ ID NO: 189) | DSDIYVNPN (SEQ ID NO: 234) | DSNIYINPN (SEQ ID NO: 279) |
| DDDDYANVN (SEQ ID NO: 10) | DDNDYFNVN (SEQ ID NO: 55) | DNDDYVNVN (SEQ ID NO: 100) | DNNDYINVN (SEQ ID NO: 145) | DNNIYANVN (SEQ ID NO: 190) | DSDIYFNVN (SEQ ID NO: 235) | DSNIYVNVN (SEQ ID NO: 280) |

-continued

| | | | | | | |
|---|---|---|---|---|---|---|
| DDDDYA NTN (SEQ ID NO: 11) | DDNDYF NTN (SEQ ID NO: 56) | DNDDYV NTN (SEQ ID NO: 101) | DNNDYIN TN (SEQ ID NO: 146) | DNNIYAN TN (SEQ ID NO: 191) | DSDIYFN TN (SEQ ID NO: 236) | DSNIYVN TN (SEQ ID NO: 281) |
| DDDDYA NPN (SEQ ID NO: 12) | DDNDYF NPN (SEQ ID NO: 57) | DNDDYV NPN (SEQ ID NO: 102) | DNNDYIN PN (SEQ ID NO: 147) | DNNIYAN PN (SEQ ID NO: 192) | DSDIYFN PN (SEQ ID NO: 237) | DSNIYVN PN (SEQ ID NO: 282) |
| DDDNYIN VN (SEQ ID NO: 13) | DDNDYA NVN (SEQ ID NO: 58) | DNDDYF NVN (SEQ ID NO: 103) | DNNDYV NVN (SEQ ID NO: 148) | DSDDYIN VN (SEQ ID NO: 193) | DSDIYAN VN (SEQ ID NO: 238) | DSNIYFN VN (SEQ ID NO: 283) |
| DDDNYIN TN (SEQ ID NO: 14) | DDNDYA NTN (SEQ ID NO: 59) | DNDDYF NTN (SEQ ID NO: 104) | DNNDYV NTN (SEQ ID NO: 149) | DSDDYIN TN (SEQ ID NO: 194) | DSDIYAN TN (SEQ ID NO: 239) | DSNIYFN TN (SEQ ID NO: 284) |
| DDDNYIN PN (SEQ ID NO: 15) | DDNDYA NPN (SEQ ID NO: 60) | DNDDYF NPN (SEQ ID NO: 105) | DNNDYV NPN (SEQ ID NO: 150) | DSDDYIN PN (SEQ ID NO: 195) | DSDIYAN PN (SEQ ID NO: 240) | DSNIYFN PN (SEQ ID NO: 285) |
| DDDNYV NVN (SEQ ID NO: 16) | DDNNYIN VN (SEQ ID NO: 61) | DNDDYA NVN (SEQ ID NO: 106) | DNNDYF NVN (SEQ ID NO: 151) | DSDDYV NVN (SEQ ID NO: 196) | DSNDYIN VN (SEQ ID NO: 241) | DSNIYAN VN (SEQ ID NO: 286) |
| DDDNYV NTN (SEQ ID NO: 17) | DDNNYIN TN (SEQ ID NO: 62) | DNDDYA NTN (SEQ ID NO: 107) | DNNDYF NTN (SEQ ID NO: 152) | DSDDYV NTN (SEQ ID NO: 197) | DSNDYIN TN (SEQ ID NO: 242) | DSNIYAN TN (SEQ ID NO: 287) |
| DDDNYV NPN (SEQ ID NO: 18) | DDNNYIN PN (SEQ ID NO: 63) | DNDDYA NPN (SEQ ID NO: 108) | DNNDYF NPN (SEQ ID NO: 153) | DSDDYV NPN (SEQ ID NO: 198) | DSNDYIN PN (SEQ ID NO: 243) | and |
| DDDNYF NVN (SEQ ID NO: 19) | DDNNYV NVN (SEQ ID NO: 64) | DNDNYIN VN (SEQ ID NO: 109) | DNNDYA NVN (SEQ ID NO: 154) | DSDDYFN VN (SEQ ID NO: 199) | DSNDYV NVN (SEQ ID NO: 244) | DSNIYAN PN (SEQ ID NO: 288). |
| DDDNYF NTN (SEQ ID NO: 20) | DDNNYV NTN (SEQ ID NO: 65) | DNDNYIN TN (SEQ ID NO: 110) | DNNDYA NTN (SEQ ID NO: 155) | DSDDYFN TN (SEQ ID NO: 200) | DSNDYV NTN (SEQ ID NO: 245) | |
| DDDNYF NPN (SEQ ID NO: 21) | DDNNYV NPN (SEQ ID NO: 66) | DNDNYIN PN (SEQ ID NO: 111) | DNNDYA NPN (SEQ ID NO: 156) | DSDDYFN PN (SEQ ID NO: 201) | DSNDYV NPN (SEQ ID NO: 246) | |
| DDDNYA NVN (SEQ ID NO: 22) | DDNNYF NVN (SEQ ID NO: 67) | DNDNYV NVN (SEQ ID NO: 112) | DNNNYIN VN (SEQ ID NO: 157) | DSDDYA NVN (SEQ ID NO: 202) | DSNDYFN VN (SEQ ID NO: 247) | |
| DDDNYA NTN (SEQ ID NO: 23) | DDNNYF NTN (SEQ ID NO: 68) | DNDNYV NTN (SEQ ID NO: 113) | DNNNYIN TN (SEQ ID NO: 158) | DSDDYA NTN (SEQ ID NO: 203) | DSNDYFN TN (SEQ ID NO: 248) | |
| DDDNYA NPN (SEQ ID NO: 24) | DDNNYF NPN (SEQ ID NO: 69) | DNDNYV NPN (SEQ ID NO: 114) | DNNNYIN PN (SEQ ID NO: 159) | DSDDYA NPN (SEQ ID NO: 204) | DSNDYFN PN (SEQ ID NO: 249) | |
| DDDHYIN VN (SEQ ID NO: 25) | DDNNYA NVN (SEQ ID NO: 70) | DNDNYF NVN (SEQ ID NO: 115) | DNNNYV NVN (SEQ ID NO: 160) | DSDNYIN VN (SEQ ID NO: 205) | DSNDYA NVN (SEQ ID NO: 250) | |
| DDDHYIN TN (SEQ ID NO: 26) | DDNNYA NTN (SEQ ID NO: 71) | DNDNYF NTN (SEQ ID NO: 116) | DNNNYV NTN (SEQ ID NO: 161) | DSDNYIN TN (SEQ ID NO: 206) | DSNDYA NTN (SEQ ID NO: 251) | |

-continued

| | | | | | |
|---|---|---|---|---|---|
| DDDHYIN PN (SEQ ID NO: 27) | DDNNYA NPN (SEQ ID NO: 72) | DNDNYF NPN (SEQ ID NO: 117) | DNNNYV NPN (SEQ ID NO: 162) | DSDNYIN PN (SEQ ID NO: 207) | DSNDYA NPN (SEQ ID NO: 252) |
| DDDHYV NVN (SEQ ID NO: 28) | DDNHYIN VN (SEQ ID NO: 73) | DNDNYA NVN (SEQ ID NO: 118) | DNNNYF NVN (SEQ ID NO: 163) | DSDNYV NVN (SEQ ID NO: 208) | DSNNYIN VN (SEQ ID NO: 253) |
| DDDHYV NTN (SEQ ID NO: 29) | DDNHYIN TN (SEQ ID NO: 74) | DNDNYA NTN (SEQ ID NO: 119) | DNNNYF NTN (SEQ ID NO: 164) | DSDNYV NTN (SEQ ID NO: 209) | DSNNYIN TN (SEQ ID NO: 254) |
| DDDHYV NPN (SEQ ID NO: 30) | DDNHYIN PN (SEQ ID NO: 75) | DNDNYA NPN (SEQ ID NO: 120) | DNNNYF NPN (SEQ ID NO: 165) | DSDNYV NPN (SEQ ID NO: 210) | DSNNYIN PN (SEQ ID NO: 255) |
| DDDHYF NVN (SEQ ID NO: 31) | DDNHYV NVN (SEQ ID NO: 76) | DNDHYIN VN (SEQ ID NO: 121) | DNNNYA NVN (SEQ ID NO: 166) | DSDNYFN VN (SEQ ID NO: 211) | DSNNYV NVN (SEQ ID NO: 256) |
| DDDHYF NTN (SEQ ID NO: 32) | DDNHYV NTN (SEQ ID NO: 77) | DNDHYIN TN (SEQ ID NO: 122) | DNNNYA NTN (SEQ ID NO: 167) | DSDNYFN TN (SEQ ID NO: 212) | DSNNYV NTN (SEQ ID NO: 257) |
| DDDHYF NPN (SEQ ID NO: 33) | DDNHYV NPN (SEQ ID NO: 78) | DNDHYIN PN (SEQ ID NO: 123) | DNNNYA NPN (SEQ ID NO: 168) | DSDNYFN PN (SEQ ID NO: 213) | DSNNYV NPN (SEQ ID NO: 258) |
| DDDHYA NVN (SEQ ID NO: 34) | DDNHYF NVN (SEQ ID NO: 79) | DNDHYV NVN (SEQ ID NO: 124) | DNNHYIN VN (SEQ ID NO: 169) | DSDNYA NVN (SEQ ID NO: 214) | DSNNYFN VN (SEQ ID NO: 259) |
| DDDHYA NTN (SEQ ID NO: 35) | DDNHYF NTN (SEQ ID NO: 80) | DNDHYV NTN (SEQ ID NO: 125) | DNNHYIN TN (SEQ ID NO: 170) | DSDNYA NTN (SEQ ID NO: 215) | DSNNYFN TN (SEQ ID NO: 260) |
| DDDHYA NPN (SEQ ID NO: 36) | DDNHYF NPN (SEQ ID NO: 81) | DNDHYV NPN (SEQ ID NO: 126) | DNNHYIN PN (SEQ ID NO: 171) | DSDNYA NPN (SEQ ID NO: 216) | DSNNYFN PN (SEQ ID NO: 261) |
| DDDIYIN VN (SEQ ID NO: 37) | DDNHYA NVN (SEQ ID NO: 82) | DNDHYF NVN (SEQ ID NO: 127) | DNNHYV NVN (SEQ ID NO: 172) | DSDHYIN VN (SEQ ID NO: 217) | DSNNYA NVN (SEQ ID NO: 262) |
| DDDIYIN TN (SEQ ID NO: 38) | DDNHYA NTN (SEQ ID NO: 83) | DNDHYF NTN (SEQ ID NO: 128) | DNNHYV NTN (SEQ ID NO: 173) | DSDHYIN TN (SEQ ID NO: 218) | DSNNYA NTN (SEQ ID NO: 263) |
| DDDIYIN PN (SEQ ID NO: 39) | DDNHYA NPN (SEQ ID NO: 84) | DNDHYF NPN (SEQ ID NO: 129) | DNNHYV NPN (SEQ ID NO: 174) | DSDHYIN PN (SEQ ID NO: 219) | DSNNYA NPN (SEQ ID NO: 264) |
| DDDIYVN VN (SEQ ID NO: 40) | DDNIYIN VN (SEQ ID NO: 85) | DNDHYA NVN (SEQ ID NO: 130) | DNNHYF NVN (SEQ ID NO: 175) | DSDHYV NVN (SEQ ID NO: 220) | DSNHYIN VN (SEQ ID NO: 265) |
| DDDIYVN TN (SEQ ID NO: 41) | DDNIYIN TN (SEQ ID NO: 86) | DNDHYA NTN (SEQ ID NO: 131) | DNNHYF NTN (SEQ ID NO: 176) | DSDHYV NTN (SEQ ID NO: 221) | DSNHYIN TN (SEQ ID NO: 266) |
| DDDIYVN PN (SEQ ID NO: 42) | DDNIYIN PN (SEQ ID NO: 87) | DNDHYA NPN (SEQ ID NO: 132) | DNNHYF NPN (SEQ ID NO: 177) | DSDHYV NPN (SEQ ID NO: 222) | DSNHYIN PN (SEQ ID NO: 267) |

| | | | | | |
|---|---|---|---|---|---|
| DDDIYFN VN (SEQ ID NO: 43) | DDNIYVN VN (SEQ ID NO: 88) | DNDIYIN VN (SEQ ID NO: 133) | DNNHYA NVN (SEQ ID NO: 178) | DSDHYFN VN (SEQ ID NO: 223) | DSNHYV NVN (SEQ ID NO: 268) |
| DDDIYFN TN (SEQ ID NO: 44) | DDNIYVN TN (SEQ ID NO: 89) | DNDIYIN TN (SEQ ID NO: 134) | DNNHYA NTN (SEQ ID NO: 179) | DSDHYFN TN (SEQ ID NO: 224) | DSNHYV NTN (SEQ ID NO: 269) |
| DDDIYFN PN (SEQ ID NO: 45) | DDNIYVN PN (SEQ ID NO: 90) | DNDIYIN PN (SEQ ID NO: 135) | DNNHYA NPN (SEQ ID NO: 180) | DSDHYFN PN (SEQ ID NO: 225) | DSNHYV NPN (SEQ ID NO: 270). |

11. The peptide of claim 3, which is DDNHYHNPN (SEQ ID NO: 307).

12. A composition comprising one or more peptides as described in claim 1 and a lanthanide metal.

13. The peptide of claim 10, which is DSDIYFNPN (SEQ ID NO: 237) or DSDNYFNFN (SEQ ID NO:317).

14. The peptide of claim 10, which is DSDIYFNPN (SEQ ID NO: 237).

15. The peptide of claim 2, comprising an amino acid sequence selected from the group consisting of:

DDDDYQNPN, (SEQ ID NO: 289)
DDDDYHNPN, (SEQ ID NO: 290)
DDDYVNPN, (SEQ ID NO: 291)
DDDHYQNPN, (SEQ ID NO: 292)
DDDHYHNPN, (SEQ ID NO: 293)
DDDHYVNPN, (SEQ ID NO: 30)
DDDNYQNPN, (SEQ ID NO: 294)
DDDNYHNPN, (SEQ ID NO: 295)
DDDNYVNPN, (SEQ ID NO: 18)
DDSDYQNPN, (SEQ ID NO: 296)
DDSDYHNPN, (SEQ ID NO: 297)
DDSHYQNPN, (SEQ ID NO: 298)
DDSHYHNPN, (SEQ ID NO: 299)
DDSHVVNPN, (SEQ ID NO: 300)
DDSNYQNPN, (SEQ ID NO: 301)
DDSNYHNPN, (SEQ ID NO: 302)
DDSNYVNPN, (SEQ ID NO: 303)
DDNDYQNPN, (SEQ ID NO: 304)
DDNDYHNPN, (SEQ ID NO: 305)
DDNDYVNPN, (SEQ ID NO: 54)
DDNHYQNPN, (SEQ ID NO: 306)
DDNHYHNPN, (SEQ ID NO: 307)
DDNHYVNPN, (SEQ ID NO: 78)
DDNNYQNPN, (SEQ ID NO: 308)
DDNNYHNPN, and (SEQ ID NO: 309)
DDNNYVNPN. (SEQ ID NO: 66)

16. A peptide comprising an amino acid sequence selected from the group consisting of:

| | | | | | | |
|---|---|---|---|---|---|---|
| DDDDYIN VN (SEQ ID NO: 1) | DDDIYAN VN (SEQ ID NO: 46) | DDNIYFN VN (SEQ ID NO: 91) | DNDIYVN VN (SEQ ID NO: 136) | DNNIYIN VN (SEQ ID NO: 181) | DSDHYA NVN (SEQ ID NO: 226) | DSNHYFN VN (SEQ ID NO: 271) |
| DDDDYIN TN (SEQ ID NO: 2) | DDDIYAN TN (SEQ ID NO: 47) | DDNIYFN TN (SEQ ID NO: 92) | DNDIYVN TN (SEQ ID NO: 137) | DNNIYIN TN (SEQ ID NO: 182) | DSDHYA NTN (SEQ ID NO: 227) | DSNHYFN TN (SEQ ID NO: 272) |

-continued

| | | | | | | |
|---|---|---|---|---|---|---|
| DDDDYIN PN (SEQ ID NO: 3) | DDDIYAN PN (SEQ ID NO: 48) | DDNIYFN PN (SEQ ID NO: 93) | DNDIYVN PN (SEQ ID NO: 138) | DNNIYIN PN (SEQ ID NO: 183) | DSDHYA NPN (SEQ ID NO: 228) | DSNHYFN PN (SEQ ID NO: 273) |
| DDDDYV NVN (SEQ ID NO: 4) | DDNDYIN VN (SEQ ID NO: 49) | DDNIYAN VN (SEQ ID NO: 94) | DNDIYFN VN (SEQ ID NO: 139) | DNNIYVN VN (SEQ ID NO: 184) | DSDIYIN VN (SEQ ID NO: 229) | DSNHYA NVN (SEQ ID NO: 274) |
| DDDDYV NTN (SEQ ID NO: 5) | DDNDYIN TN (SEQ ID NO: 50) | DDNIYAN TN (SEQ ID NO: 95) | DNDIYFN TN (SEQ ID NO: 140) | DNNIYVN TN (SEQ ID NO: 185) | DSDIYINT N (SEQ ID NO: 230) | DSNHYA NTN (SEQ ID NO: 275) |
| DDDDYV NPN (SEQ ID NO: 6) | DDNDYIN PN (SEQ ID NO: 51) | DDNIYAN PN (SEQ ID NO: 96) | DNDIYFN PN (SEQ ID NO: 141) | DNNIYVN PN (SEQ ID NO: 186) | DSDIYINP N (SEQ ID NO: 231) | DSNHYA NPN (SEQ ID NO: 276) |
| DDDDYF NVN (SEQ ID NO: 7) | DDNDYV NVN (SEQ ID NO: 52) | DNDDYIN VN (SEQ ID NO: 97) | DNDIYAN VN (SEQ ID NO: 142) | DNNIYFN VN (SEQ ID NO: 187) | DSDIYVN VN (SEQ ID NO: 232) | DSNIYIN VN (SEQ ID NO: 277) |
| DDDDYF NTN (SEQ ID NO: 8) | DDNDYV NTN (SEQ ID NO: 53) | DNDDYIN TN (SEQ ID NO: 98) | DNDIYAN TN (SEQ ID NO: 143) | DNNIYFN TN (SEQ ID NO: 188) | DSDIYVN TN (SEQ ID NO: 233) | DSNIYINT N (SEQ ID NO: 278) |
| DDDDYF NPN (SEQ ID NO: 9) | DDNDYV NPN (SEQ ID NO: 54) | DNDDYIN PN (SEQ ID NO: 99) | DNDIYAN PN (SEQ ID NO: 144) | DNNIYFN PN (SEQ ID NO: 189) | DSDIYVN PN (SEQ ID NO: 234) | DSNIYINP N (SEQ ID NO: 279) |
| DDDDYA NVN (SEQ ID NO: 10) | DDNDYF NVN (SEQ ID NO: 55) | DNDDYV NVN (SEQ ID NO: 100) | DNNDYIN VN (SEQ ID NO: 145) | DNNIYAN VN (SEQ ID NO: 190) | DSDIYFN VN (SEQ ID NO: 235) | DSNIYVN VN (SEQ ID NO: 280) |
| DDDDYA NTN (SEQ ID NO: 11) | DDNDYF NTN (SEQ ID NO: 56) | DNDDYV NTN (SEQ ID NO: 101) | DNNDYIN TN (SEQ ID NO: 146) | DNNIYAN TN (SEQ ID NO: 191) | DSDIYFN TN (SEQ ID NO: 236) | DSNIYVN TN (SEQ ID NO: 281) |
| DDDDYA NPN (SEQ ID NO: 12) | DDNDYF NPN (SEQ ID NO: 57) | DNDDYV NPN (SEQ ID NO: 102) | DNNDYIN PN (SEQ ID NO: 147) | DNNIYAN PN (SEQ ID NO: 192) | DSDIYFN PN (SEQ ID NO: 237) | DSNIYVN PN (SEQ ID NO: 282) |
| DDDNYIN VN (SEQ ID NO: 13) | DDNDYA NVN (SEQ ID NO: 58) | DNDDYF NVN (SEQ ID NO: 103) | DNNDYV NVN (SEQ ID NO: 148) | DSDDYIN VN (SEQ ID NO: 193) | DSDIYAN VN (SEQ ID NO: 238) | DSNIYFN VN (SEQ ID NO: 283) |
| DDDNYIN TN (SEQ ID NO: 14) | DDNDYA NTN (SEQ ID NO: 59) | DNDDYF NTN (SEQ ID NO: 104) | DNNDYV NTN (SEQ ID NO: 149) | DSDDYIN TN (SEQ ID NO: 194) | DSDIYAN TN (SEQ ID NO: 239) | DSNIYFN TN (SEQ ID NO: 284) |
| DDDNYIN PN (SEQ ID NO: 15) | DDNDYA NPN (SEQ ID NO: 60) | DNDDYF NPN (SEQ ID NO: 105) | DNNDYV NPN (SEQ ID NO: 150) | DSDDYIN PN (SEQ ID NO: 195) | DSDIYAN PN (SEQ ID NO: 240) | DSNIYFN PN (SEQ ID NO: 285) |
| DDDNYV NVN (SEQ ID NO: 16) | DDNNYIN VN (SEQ ID NO: 61) | DNDDYA NVN (SEQ ID NO: 106) | DNNDYF NVN (SEQ ID NO: 151) | DSDDYV NVN (SEQ ID NO: 196) | DSNDYIN VN (SEQ ID NO: 241) | DSNIYAN VN (SEQ ID NO: 286) |
| DDDNYV NTN (SEQ ID NO: 17) | DDNNYIN TN (SEQ ID NO: 62) | DNDDYA NTN (SEQ ID NO: 107) | DNNDYF NTN (SEQ ID NO: 152) | DSDDYV NTN (SEQ ID NO: 197) | DSNDYIN TN (SEQ ID NO: 242) | DSNIYAN TN (SEQ ID NO: 287) |
| DDDNYV NPN (SEQ ID NO: 18) | DDNNYIN PN (SEQ ID NO: 63) | DNDDYA NPN (SEQ ID NO: 108) | DNNDYF NPN (SEQ ID NO: 153) | DSDDYV NPN (SEQ ID NO: 198) | DSNDYIN PN (SEQ ID NO: 243) | and |

-continued

| | | | | | | |
|---|---|---|---|---|---|---|
| DDDNYF NVN (SEQ ID NO: 19) | DDNNYV NVN (SEQ ID NO: 64) | DNDNYIN VN (SEQ ID NO: 109) | DNNDYA NVN (SEQ ID NO: 154) | DSDDYFN VN (SEQ ID NO: 199) | DSNDYV NVN (SEQ ID NO: 244) | DSNIYAN PN (SEQ ID NO: 288). |
| DDDNYF NTN (SEQ ID NO: 20) | DDNNYV NTN (SEQ ID NO: 65) | DNDNYIN TN (SEQ ID NO: 110) | DNNDYA NTN (SEQ ID NO: 155) | DSDDYFN TN (SEQ ID NO: 200) | DSNDYV NTN (SEQ ID NO: 245) | |
| DDDNYF NPN (SEQ ID NO: 21) | DDNNYV NPN (SEQ ID NO: 66) | DNDNYIN PN (SEQ ID NO: 111) | DNNDYA NPN (SEQ ID NO: 156) | DSDDYFN PN (SEQ ID NO: 201) | DSNDYV NPN (SEQ ID NO: 246) | |
| DDDNYA NVN (SEQ ID NO: 22) | DDNNYF NVN (SEQ ID NO: 67) | DNDNYV NVN (SEQ ID NO: 112) | DNNNYIN VN (SEQ ID NO: 157) | DSDDYA NVN (SEQ ID NO: 202) | DSNDYFN VN (SEQ ID NO: 247) | |
| DDDNYA NTN (SEQ ID NO: 23) | DDNNYF NTN (SEQ ID NO: 68) | DNDNYV NTN (SEQ ID NO: 113) | DNNNYIN TN (SEQ ID NO: 158) | DSDDYA NTN (SEQ ID NO: 203) | DSNDYFN TN (SEQ ID NO: 248) | |
| DDDNYA NPN (SEQ ID NO: 24) | DDNNYF NPN (SEQ ID NO: 69) | DNDNYV NPN (SEQ ID NO: 114) | DNNNYIN PN (SEQ ID NO: 159) | DSDDYA NPN (SEQ ID NO: 204) | DSNDYFN PN (SEQ ID NO: 249) | |
| DDDHYIN VN (SEQ ID NO: 25) | DDNNYA NVN (SEQ ID NO: 70) | DNDNYF NVN (SEQ ID NO: 115) | DNNNYV NVN (SEQ ID NO: 160) | DSDNYIN VN (SEQ ID NO: 205) | DSNDYA NVN (SEQ ID NO: 250) | |
| DDDHYIN TN (SEQ ID NO: 26) | DDNNYA NTN (SEQ ID NO: 71) | DNDNYF NTN (SEQ ID NO: 116) | DNNNYV NTN (SEQ ID NO: 161) | DSDNYIN TN (SEQ ID NO: 206) | DSNDYA NTN (SEQ ID NO: 251) | |
| DDDHYIN PN (SEQ ID NO: 27) | DDNNYA NPN (SEQ ID NO: 72) | DNDNYF NPN (SEQ ID NO: 117) | DNNNYV NPN (SEQ ID NO: 162) | DSDNYIN PN (SEQ ID NO: 207) | DSNDYA NPN (SEQ ID NO: 252) | |
| DDDHYV NVN (SEQ ID NO: 28) | DDNHYIN VN (SEQ ID NO: 73) | DNDNYA NVN (SEQ ID NO: 118) | DNNNYF NVN (SEQ ID NO: 163) | DSDNYV NVN (SEQ ID NO: 208) | DSNNYIN VN (SEQ ID NO: 253) | |
| DDDHYV NTN (SEQ ID NO: 29) | DDNHYIN TN (SEQ ID NO: 74) | DNDNYA NTN (SEQ ID NO: 119) | DNNNYF NTN (SEQ ID NO: 164) | DSDNYV NTN (SEQ ID NO: 209) | DSNNYIN TN (SEQ ID NO: 254) | |
| DDDHYV NPN (SEQ ID NO: 30) | DDNHYIN PN (SEQ ID NO: 75) | DNDNYA NPN (SEQ ID NO: 120) | DNNNYF NPN (SEQ ID NO: 165) | DSDNYV NPN (SEQ ID NO: 210) | DSNNYIN PN (SEQ ID NO: 255) | |
| DDDHYF NVN (SEQ ID NO: 31) | DDNHYV NVN (SEQ ID NO: 76) | DNDHYIN VN (SEQ ID NO: 121) | DNNNYA NVN (SEQ ID NO: 166) | DSDNYFN VN (SEQ ID NO: 211) | DSNNYV NVN (SEQ ID NO: 256) | |
| DDDHYF NTN (SEQ ID NO: 32) | DDNHYV NTN (SEQ ID NO: 77) | DNDHYIN TN (SEQ ID NO: 122) | DNNNYA NTN (SEQ ID NO: 167) | DSDNYFN TN (SEQ ID NO: 212) | DSNNYV NTN (SEQ ID NO: 257) | |
| DDDHYF NPN (SEQ ID NO: 33) | DDNHYV NPN (SEQ ID NO: 78) | DNDHYIN PN (SEQ ID NO: 123) | DNNNYA NPN (SEQ ID NO: 168) | DSDNYFN PN (SEQ ID NO: 213) | DSNNYV NPN (SEQ ID NO: 258) | |
| DDDHYA NVN (SEQ ID NO: 34) | DDNHYF NVN (SEQ ID NO: 79) | DNDHYV NVN (SEQ ID NO: 124) | DNNHYIN VN (SEQ ID NO: 169) | DSDNYA NVN (SEQ ID NO: 214) | DSNNYFN VN (SEQ ID NO: 259) | |

-continued

| | | | | | |
|---|---|---|---|---|---|
| DDDHYANTN (SEQ ID NO: 35) | DDNHYFNTN (SEQ ID NO: 80) | DNDHYVNTN (SEQ ID NO: 125) | DNNHYINTN (SEQ ID NO: 170) | DSDNYANTN (SEQ ID NO: 215) | DSNNYFNTN (SEQ ID NO: 260) |
| DDDHYANPN (SEQ ID NO: 36) | DDNHYFNPN (SEQ ID NO: 81) | DNDHYVNPN (SEQ ID NO: 126) | DNNHYINPN (SEQ ID NO: 171) | DSDNYANPN (SEQ ID NO: 216) | DSNNYFNPN (SEQ ID NO: 261) |
| DDDIYINVN (SEQ ID NO: 37) | DDNHYANVN (SEQ ID NO: 82) | DNDHYFNVN (SEQ ID NO: 127) | DNNHYVNVN (SEQ ID NO: 172) | DSDHYINVN (SEQ ID NO: 217) | DSNNYANVN (SEQ ID NO: 262) |
| DDDIYINTN (SEQ ID NO: 38) | DDNHYANTN (SEQ ID NO: 83) | DNDHYFNTN (SEQ ID NO: 128) | DNNHYVNTN (SEQ ID NO: 173) | DSDHYINTN (SEQ ID NO: 218) | DSNNYANTN (SEQ ID NO: 263) |
| DDDIYINPN (SEQ ID NO: 39) | DDNHYANPN (SEQ ID NO: 84) | DNDHYFNPN (SEQ ID NO: 129) | DNNHYVNPN (SEQ ID NO: 174) | DSDHYINPN (SEQ ID NO: 219) | DSNNYANPN (SEQ ID NO: 264) |
| DDDIYVNVN (SEQ ID NO: 40) | DDNIYINVN (SEQ ID NO: 85) | DNDHYANVN (SEQ ID NO: 130) | DNNHYFNVN (SEQ ID NO: 175) | DSDHYVNVN (SEQ ID NO: 220) | DSNHYINVN (SEQ ID NO: 265) |
| DDDIYVNTN (SEQ ID NO: 41) | DDNIYINTN (SEQ ID NO: 86) | DNDHYANTN (SEQ ID NO: 131) | DNNHYFNTN (SEQ ID NO: 176) | DSDHYVNTN (SEQ ID NO: 221) | DSNHYINTN (SEQ ID NO: 266) |
| DDDIYVNPN (SEQ ID NO: 42) | DDNIYINPN (SEQ ID NO: 87) | DNDHYANPN (SEQ ID NO: 132) | DNNHYFNPN (SEQ ID NO: 177) | DSDHYVNPN (SEQ ID NO: 222) | DSNHYINPN (SEQ ID NO: 267) |
| DDDIYFNVN (SEQ ID NO: 43) | DDNIYVNVN (SEQ ID NO: 88) | DNDIYINVN (SEQ ID NO: 133) | DNNHYANVN (SEQ ID NO: 178) | DSDHYFNVN (SEQ ID NO: 223) | DSNHYVNVN (SEQ ID NO: 268) |
| DDDIYFNTN (SEQ ID NO: 44) | DDNIYVNTN (SEQ ID NO: 89) | DNDIYINTN (SEQ ID NO: 134) | DNNHYANTN (SEQ ID NO: 179) | DSDHYFNTN (SEQ ID NO: 224) | DSNHYVNTN (SEQ ID NO: 269) |
| DDDIYFNPN (SEQ ID NO: 45) | DDNIYVNPN (SEQ ID NO: 90) | DNDIYINPN (SEQ ID NO: 135) | DNNHYANPN (SEQ ID NO: 180) | DSDHYFNPN (SEQ ID NO: 225) | DSNHYVNPN (SEQ ID NO: 270). |

17. A method to identify an inhibitor of FLT3 kinase comprising: determining whether a test compound disrupts the interaction of FLT3 with a peptide as described in claim 1, wherein a disruption indicates that the test compound is an inhibitor of FLT3.

18. A method to determine if FLT3 kinase is active in a system comprising: determining whether a peptide as described in claim 1 has served as a substrate for FLT3 activity, wherein such a positive indication of activity indicates that FLT3 is active in the system.

19. A method for detecting the activity of a kinase comprising:
   1) contacting the kinase with a peptide as described in claim 1 to provide a resulting mixture;
   2) contacting the resulting mixture with a lanthanide metal, under conditions such that a luminescent signal from the lanthanide metal is generated; and
   3) detecting the luminescent signal, wherein the luminescent signal correlates with the activity of the kinase.

20. The method of claim 19, further comprising comparing the luminescent signal to a reference luminescent signal, wherein a change in the luminescent signal as compared to the reference luminescent signal is indicative of kinase activity.

21. A method to identify an inhibitor of a kinase comprising:
   1) contacting a peptide as described in claim 1, the kinase, and a test compound to provide a resulting mixture;
   2) contacting the resulting mixture with a lanthanide metal; and
   3) detecting a luminescent signal from the lanthanide metal, wherein the luminescent signal from the lanthanide metal correlates with the ability of the test compound to inhibit to the kinase.

22. The method of claim 21, further comprising comparing the luminescent signal to a reference luminescent signal, wherein a change in the luminescent signal as compared to the reference luminescent signal indicates the test compound is an inhibitor of the kinase.

23. The method of claim 21, wherein the peptide as described in claim 1 and the test compound competitively bind to the kinase.

24. The method of claim 21, wherein the luminescent signal is detected by luminescence spectroscopy or by time-resolved luminescence spectroscopy.

* * * * *

UNITED STATES PATENT AND TRADEMARK OFFICE
CERTIFICATE OF CORRECTION

PATENT NO. : 10,590,168 B2
APPLICATION NO. : 15/603273
DATED : March 17, 2020
INVENTOR(S) : Laurie L. Parker and Minervo Perez Page 1 of 1

It is certified that error appears in the above-identified patent and that said Letters Patent is hereby corrected as shown below:

In the Claims

Column 167, Lines 65 and 66, Claim 3, please delete "DDDYVNPN, (SEQ ID NO: 291)";

Column 168, Lines 53 and 54, Claim 3, please delete "DDSHVVNPN, (SEQ ID NO: 300)";

Column 171, Row 8, Column 7, Claim 10, please insert -- DSDNYFNFN (SEQ ID NO: 317) -- prior to the word "and";

Column 175, Lines 34 and 35, Claim 15, please delete "DDDYVNPN, SEQ ID NO: 291)";

Column 176, Lines 23 and 24, Claim 15, please delete "DDSHVVNPN, (SEQ ID NO: 300)"; and Column 177, Row 16, Column 7, Claim 16, please insert -- DSDNYFNFN (SEQ ID NO: 317) -- prior to the word "and", therefor.

Signed and Sealed this
Fifteenth Day of June, 2021

Drew Hirshfeld
*Performing the Functions and Duties of the
Under Secretary of Commerce for Intellectual Property and
Director of the United States Patent and Trademark Office*